United States Patent
Wang et al.

(10) Patent No.: US 9,683,226 B2
(45) Date of Patent: Jun. 20, 2017

(54) MUTANTS OF ACTIVATION-INDUCED CYTIDINE DEAMINASE (AID) AND METHODS OF USE

(75) Inventors: Meng Wang, Norwich (GB); Zizhen Yang, London (GB); Cristina Rada, Cambridge (GB); Michael Neuberger, Cambridge (GB)

(73) Assignee: Medical Research Council, Wiltshire (GB)

( * ) Notice: Subject to any disclaimer, the term of this patent is extended or adjusted under 35 U.S.C. 154(b) by 1127 days.

(21) Appl. No.: 13/262,187

(22) PCT Filed: Apr. 5, 2010

(86) PCT No.: PCT/IB2010/000958
§ 371 (c)(1),
(2), (4) Date: Feb. 29, 2012

(87) PCT Pub. No.: WO2010/113039
PCT Pub. Date: Oct. 7, 2010

(65) Prior Publication Data
US 2012/0151613 A1    Jun. 14, 2012

Related U.S. Application Data

(60) Provisional application No. 61/166,349, filed on Apr. 3, 2009.

(51) Int. Cl.
*C12N 9/78* (2006.01)
*C12N 15/00* (2006.01)
(Continued)

(52) U.S. Cl.
CPC ............... *C12N 9/78* (2013.01); *C07K 16/00* (2013.01); *C12Y 305/04005* (2013.01); *C07K 2319/23* (2013.01); *C12N 2799/027* (2013.01)

(58) Field of Classification Search
CPC ........................ C12N 9/78; C12Y 205/04005
See application file for complete search history.

(56) References Cited

U.S. PATENT DOCUMENTS 4,518,584 A   5/1985   Mark et al.
4,737,462 A   4/1988   Mark et al.
(Continued)

FOREIGN PATENT DOCUMENTS

EP   1 930 430 A1   6/2008
RU   2 126 405 C1   2/1999
(Continued)

OTHER PUBLICATIONS

Di Palma, F., et al., 2009, "The Genome Sequence of *Anolis carolinensis* (Green Anole Lizard)", Submitted (Dec. 2009) to the EMBL/GenBank/DDBJ databases: Accession No. G1KTX0_ANOCA.*

(Continued)

*Primary Examiner* — Nashaat Nashed
*Assistant Examiner* — William W Moore
(74) *Attorney, Agent, or Firm* — Leydig, Voit & Mayer, Ltd

(57) ABSTRACT

The invention provides functional mutants of activation-induced cytidine deaminase (AID) protein that have increased activity as compared to a wild-type AID protein. The invention also provides nucleic acids encoding the functional AID mutants, and vectors and cells comprising the nucleic acids. The invention further provides methods of using the functional mutant AID proteins.

21 Claims, 12 Drawing Sheets

(51) Int. Cl.
C12N 15/85 (2006.01)
C07K 16/00 (2006.01)

(56) References Cited

U.S. PATENT DOCUMENTS

| | | | |
|---|---|---|---|
| 4,937,190 A | 6/1990 | Palmenberg et al. | |
| 4,959,317 A | 9/1990 | Sauer | |
| 5,070,012 A | 12/1991 | Nolan et al. | |
| 5,122,464 A | 6/1992 | Wilson et al. | |
| 5,221,623 A | 6/1993 | Legocki et al. | |
| 5,464,758 A | 11/1995 | Gossen et al. | |
| 5,650,289 A | 7/1997 | Wood | |
| 5,654,182 A | 8/1997 | Wahl et al. | |
| 5,674,713 A | 10/1997 | McElroy et al. | |
| 5,677,177 A | 10/1997 | Wahl et al. | |
| 5,683,888 A | 11/1997 | Campbell | |
| 5,741,657 A | 4/1998 | Tsien et al. | |
| 5,770,359 A | 6/1998 | Wilson et al. | |
| 5,770,428 A | 6/1998 | Boris-Lawrie | |
| 5,814,618 A | 9/1998 | Bujard et al. | |
| 5,843,746 A | 12/1998 | Tatsumi et al. | |
| 5,885,827 A | 3/1999 | Wabl et al. | |
| 5,955,604 A | 9/1999 | Tsien et al. | |
| 6,815,194 B2* | 11/2004 | Honjo et al. | 435/227 |
| 7,083,966 B2* | 8/2006 | Honjo et al. | 435/227 |
| 7,112,715 B2 | 9/2006 | Chambon et al. | |
| 7,314,621 B2* | 1/2008 | Honjo et al. | 424/139.1 |
| 7,745,391 B2* | 6/2010 | Mintz et al. | 514/19.3 |
| 7,803,582 B2* | 9/2010 | Xu | 435/91.4 |
| 8,095,350 B2* | 1/2012 | Chen et al. | 703/11 |
| 8,603,950 B2* | 12/2013 | Bowers et al. | 506/26 |
| 2006/0019262 A1* | 1/2006 | Petersen-Mahrt et al. | 435/6 |
| 2006/0246568 A1* | 11/2006 | Honjo et al. | 435/227 |
| 2008/0227123 A1 | 9/2008 | Ohmori et al. | |
| 2008/0293068 A1 | 11/2008 | Tsien et al. | |
| 2009/0075378 A1* | 3/2009 | Horlick et al. | 435/375 |
| 2009/0093024 A1* | 4/2009 | Bowers et al. | 435/69.6 |
| 2009/0226922 A1* | 9/2009 | Grawunder et al. | 435/6 |
| 2009/0269831 A1* | 10/2009 | Harris et al. | 435/227 |
| 2010/0160174 A1* | 6/2010 | Smith et al. | 506/9 |
| 2011/0138491 A1* | 6/2011 | Reik et al. | 800/18 |

FOREIGN PATENT DOCUMENTS

| | | |
|---|---|---|
| WO | WO 92/08796 A1 | 5/1992 |
| WO | WO 93/03027 A1 | 2/1993 |
| WO | WO 94/28143 A1 | 12/1994 |
| WO | WO 2008/103474 A1 | 8/2008 |
| WO | WO 2008/103475 A1 | 8/2008 |

OTHER PUBLICATIONS

Durandy, A., et al., 2006, "Activation-induced cytidine deaminase: Structure-function relationship as based on the study of mutants", Human Mutation, vol. 27, No. 12, pp. 1185-1191.*
UniProtKB/Swiss-Prot database Accession No. ABEC3_MOUSE, Apr. 13, 2004 in alignment with SEQ ID No. 1 of the application, 5 pages.*
UniProtKB/Swiss-Prot database Accession No. C7AG72_HORSE, Sep. 22, 2009 in alignment with SEQ ID No. 1 of the application, 2 pages.*
Abremski et al., *Cell*, 32: 1301-1311 (1983).
Arakawa et al., *PLoS Biol.*, 2: E179 (2004).
Arakawa et al., *Nucleic Acids Res.*, 36(1): e1 (2008).
Barreto et al., *Mol. Cell*, 12: 501-508 (2003).
Batista et al., *Immunity*, 8(6): 751-759 (1998).
Batista et al., *EMBO J.*, 19(4): 513-520 (2000).
Bauer et al., *Gene*, 37: 73-81 (1985).
Bebenek et al., *Methods Enzymol.*, 262: 217-232 (1995).
Berger et al., *Gene*, 66: 1-10 (1998).
Boder et al., *Nat. Biotechnol.*, 15: 553-557 (1997).
Bransteitter et al., *J. Biol. Chem.*, 279: 51612-51621 (2004).
Brash et al., *Molec. Cell. Biol.*, 7: 2031-2034 (1987).
Buerstedde et al., *EMBO J.*, 9: 921-927 (1990).
Capecchi, *Nat. Rev. Genet.*, 6(6): 507-512 (2005).
Chen et al., *Nature*, 452: 116-119 (2008).
Colberre-Garapin et al., *J. Mol. Biol.*, 150: 1-14 (1981).
Conese et al., *Gene Therapy*, 11: 1735-1742 (2004).
Conticello et al., *Mol. Biol. Evol.*, 22: 367-377 (2005).
Conticello et al., *Nat. Struct. Mol. Biol.*, 14: 7-9 (2007).
Conticello et al., *Mol. Cell*, 31: 474-484 (2008).
Corbel et al., *Curr. Opin. Biotechnol.*, 13(5): 448-452 (2002).
Craik, *Biotechniques*, 3(1): 12-19 (Jan. 1995).
Crooks et al., *Genome Research*, 14: 1188-1190 (2004).
Cumbers et al., *Nat. Biotechnol.*, 20(11): 1129-1134 (2002).
Cupples et al., *Proc. Natl. Acad. Sci. USA*, 86: 5345-5349 (1989).
Di Noia et al., *Nature*, 419: 43-48 (2002).
Di Noia, *J. Exp. Med.*, 204: 3209-3219 (2007).
European Patent Office, International Search Report in International Patent Application PCT/IB2010/000958 (Sep. 10, 2010).
European Patent Office, Written Opinion in International Patent Application PCT/IB2010/000958 (Sep. 10, 2010).
Feng et al., *Methods Mol. Med.*, 99: 255-267 (2004).
Fuhrmann-Benzakein et al., *Nuc. Acid. Res.*, 28: e99 (2000).
Ghiasi et al., *Virology*, 185: 187-194 (1991).
Glickman et al., *J. Biomolecular Screening*, 7(1): 3-10 (2002).
Gorman et al., *Mol. Cell. Biol.*, 2: 1044-1051 (1982).
Gunneriusson et al., *J. Bacteriol.*, 78: 1341-1346 (1996).
Guzman et al., *J. Bacteriol.*, 177: 4121-4130 (1995).
Harris et al., *Mol. Cell.*, 10: 1247-1253 (2002).
Heinzel et al., *J. Virol.*, 62(10): 3738-3746 (1988).
Hoffmann et al., *Biotechnol. Annu. Rev.*, 10: 1-30 (2004).
Holden et al., *Nature*, 456: 121-124 (2008).
Indra et al., *Nuc. Acid. Res.*, 27: 4324-4327 (1999).
Jack et al., *Proc. Natl. Acad. Sci. USA*, 85: 1581-1585 (1988).
Janz et al., *Proc. Natl. Acad. Sci. USA*, 90: 7361-7365 (1993).
Jarmuz et al., *Genomics*, 79: 285-296 (2002).
Johnston, *Nature*, 346: 776-777 (1990).
Jones et al., *Nature*, 321: 522-525 (1986).
Jovanic et al., *PLoS ONE*, 23;3(1): e1480 (2008).
Kain, *Methods Mol. Biol.*, 63: 49-60 (1997).
Kent et al., *Science*, 237: 901-903 (1987).
Kitts et al., *Biotechniques*, 14: 810-817 (1993).
Köhler et al., *Eur. J. Immunol.*, 5: 511-519 (1976).
Kramer et al., *Methods Mol. Biol.*, 308: 123-144 (2005).
Larkin et al., *Bioinformatics*, 23: 2947-2948 (2007).
Larue et al., *J. Virol.*, 83: 494-497 (2009).
Lonberg, *Nat. Biotechnol.*, 23(9): 1117-1125 (2005).
Lonberg, *Handb. Exp. Pharmacol.*, 181: 69-97 (2008).
Lucklow, *Curr. Opin. Biotechnol.*, 4: 564-572 (1993).
Lucklow et al., *J. Virol.*, 67: 4566-4579 (1993).
Lowy et al., *Cell*, 22: 817-823 (1980).
Maniatis et al., *Cell Biology: A Comprehensive Treatise, vol. 3, Gene Sequence Expression*, Academic Press, NY, pp. 563-608 (1980).
Martin et al., *Proc. Natl. Acad. Sci. USA.*, 99(19): 12304-12308 (2002).
Martin et al., *Nature*, 415(6873): 802-806 (2002).
Mastrobattista et al., *Chem. Biol.*, 12(12): 1291-1300 (2005).
Mazor et al., *Nat. Biotechnol.*, 25(5): 563-565 (2007).
McBride et al., *Proc. Natl. Acad. Sci. USA*, 103(23): 8798-803 (2006).
McBride et al., *J. Exp. Med.*, 205: 2585-2594 (2008).
Mulligan et al., *Proc. Natl. Acad. Sci. USA*, 78: 2072-2076 (1981).
Muramatsu et al., *Cell*, 102(5): 553-563 (2000).
Nghiem et al., *Proc. Natl. Acad. Sci. USA*, 85: 2709-2713 (1988).
No et al., *Proc. Natl. Acad. Sci.*, 93: 3346-3351 (1996).
Nussinov, *J. Mol. Biol.*, 149: 125-131 (1981).
O'Hare et al., *Proc. Natl. Acad. Sci. USA*, 78: 1527-1531 (1981).
Olsen et al., *Methods Mol. Biol.*, 230: 329-349 (2003).
Parsa et al., *Mol. Immunol.*, 44(4): 567-75 (2007).
Paul, *Fundamental Immunology, 3rd Edition*, Raven Press, New York, pp. 353-363 (1993).
Petersen-Mahrt et al., *Nature*, 418 (6893): 99-103 (2002).
Pham et al., *Nature*, 424: 103-107 (2003).

(56) References Cited

OTHER PUBLICATIONS

Pham et al., *J. Biol. Chem.*, 283 (25): 17428-17439 (2008).
Plückthun, *BioTechnology*, 9: 545-551 (1991).
Presta, *Curr. Op. Struct. Biol.*, 2: 593-596 (1992).
Ramiro et al., *Nature*, 440: 105-109 (2006).
Reichmann et al., *Nature*, 332: 323-329 (1988).
Revy et al, *Cell*, 102(5): 565-575 (2000).
Ruckerl et al., Mol. Immunol., 41: 1135-1143 (2004).
Ruckerl et al., *Mol. Immunol.*, 43(10): 1645-1652 (2006).
Ruiz et al., *J. Bacteriol.*, 175: 4985-4989 (1993).
Salazar et al., *Methods. Mol. Biol.*, 230: 85-97 (2003).
Sale et al., *Nature*, 412: 921-926 (2001).
Sandy et al., *Biotechniques*, 39: 215-224 (2005).
Santerre et al., *Gene*, 30: 147-156 (1984).
Saribasak et al., *J. Immunol.*, 176: 365-371 (2006).
Schindehutte et al., *Stem Cells*, 23(1): 10-15 (2005).
Seo et al., *Nat. Biotechnol.*, 23(6): 731-735 (2005).
Seo et al., *Nat. Protoc.*, 1(3): 1502-1506 (2006).
Seo et al., *Biotechnol. Genet.*, Eng. Rev., 24: 179-193 (2007).
Sioud et al., *Curr. Drug Targets*, 6: 647-653 (2005).
Sitaraman et al., *J. Biotechnol.*, 110(3): 257-263 (2004).
Szybalska et al., *Proc. Natl. Acad. Sci. USA*, 48: 2026-2034 (1962).
Ta et al., *Nat. Immunol.*, 4(9): 843-848 (2003).
Teng et al., *Immunity*, 28: 621-629 (2008).
Tsien, *Annu. Rev. Biochem.*, 67: 509-544 (1998).
Todo et al., *J. Biosci. Bioeng.*, 102(5): 478-481 (2006).
Turner, *Trends Biotechnol.*, 21(11): 474-478 (2003).
Walder et al., *Gene*, 42: 133-139 (1986).
Wang et al., *Prot. Eng. Des. Sel.*, 17(9): 569-664 (2004).
Wang et al., *Proc. Natl. Acad. Sci. USA.*, 101(48): 16745-16749 (2004).
Wang et al., *Nat. Struc. Mol. Biol.*, 16: 769-776 (2009).
Wigler et al., *Cell*, 11: 223-232 (1977).
Wigler et al., *Proc. Natl. Acad. Sci. USA*, 77: 3567-3570 (1980).
Winter et al., *Annu. Rev. Immunol.*, 12: 433-455 (1994).
Yebenes et al., *J. Exp. Med.*, 205: 2199-2206 (2008).
Yoshikawa et al., *Science*, 296 (5575): 2033-2036 (2002).
Zhang et al., *Int. Immunol.*, 13: 1175-1184 (2001).
Zhao et al., *Curr. Opin. Biotechnol.*, 13(2): 104-110 (2002).
Chinese Patent Office, Office Action in Chinese Patent Application No. 201080023311.X (Dec. 17, 2012).
Chinese Patent Office, Office Action in Chinese Patent Application No. 201080023311.X (Nov. 27, 2013).
Chinese Patent Office, Office Action in Chinese Patent Application No. 201080023311.X (Jun. 17, 2014).
European Patent Office, Communication pursuant to Article 94(3) EPC in European Patent Application No. 10 723 293.6 (Dec. 21, 2012).
Japanese Patent Office, Notice of Reason for Refusal in Japanese Patent Application No. 502830/2012 (Aug. 5, 2014).
Russian Patent Office, Office Action in Russian Patent Application No. 2011144569 (Feb. 1, 2012).
Russian Patent Office, Office Action in Russian Patent Application No. 2011144569 (Apr. 7, 2014).
Russian Patent Office, Decision of Grant of Patent of Invention in Russian Patent Application No. 2011144569 (Aug. 8, 2014).
Shivarov et al., "Dissociation of in vitro DNA deamination activity and physiological functions of AID mutants," *PNAS*, 105(41): 15866-15871 (Oct. 14, 2008).

* cited by examiner

FIG. 2

FIG. 3
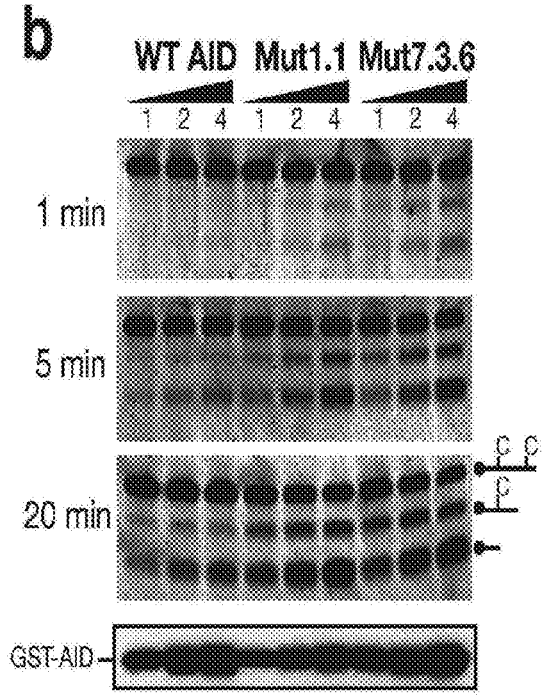
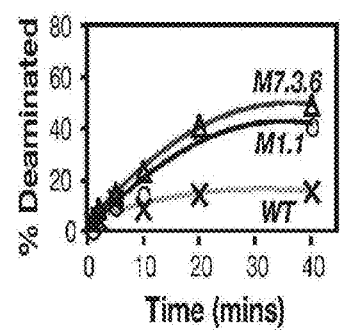
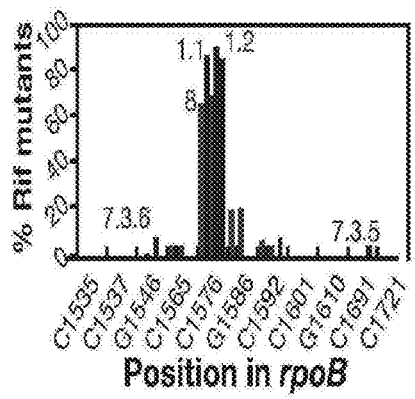

FIG. 4
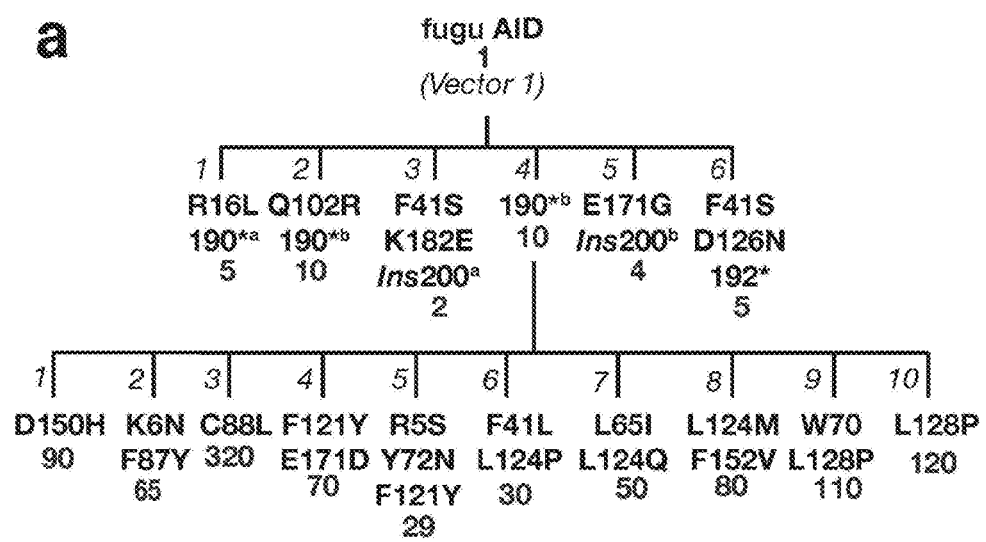
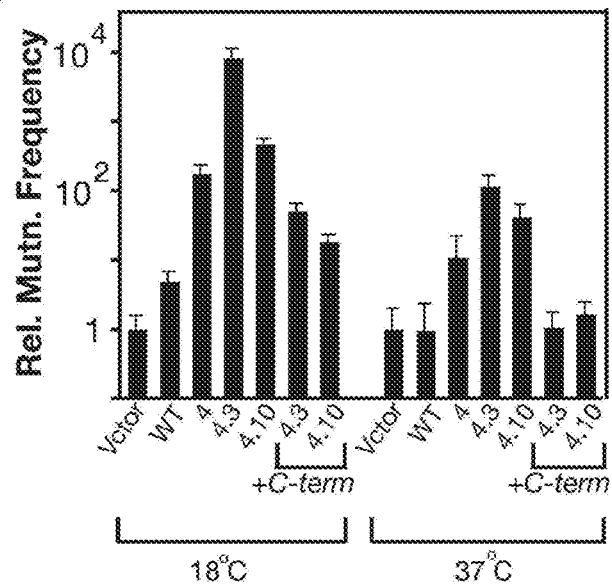

FIG. 5
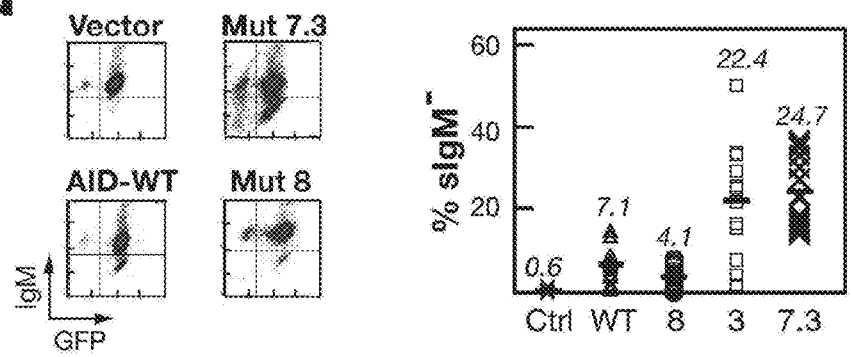
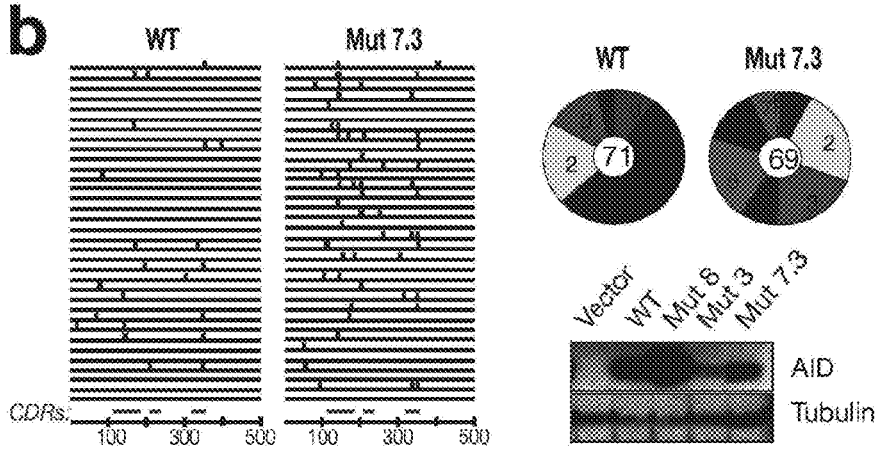
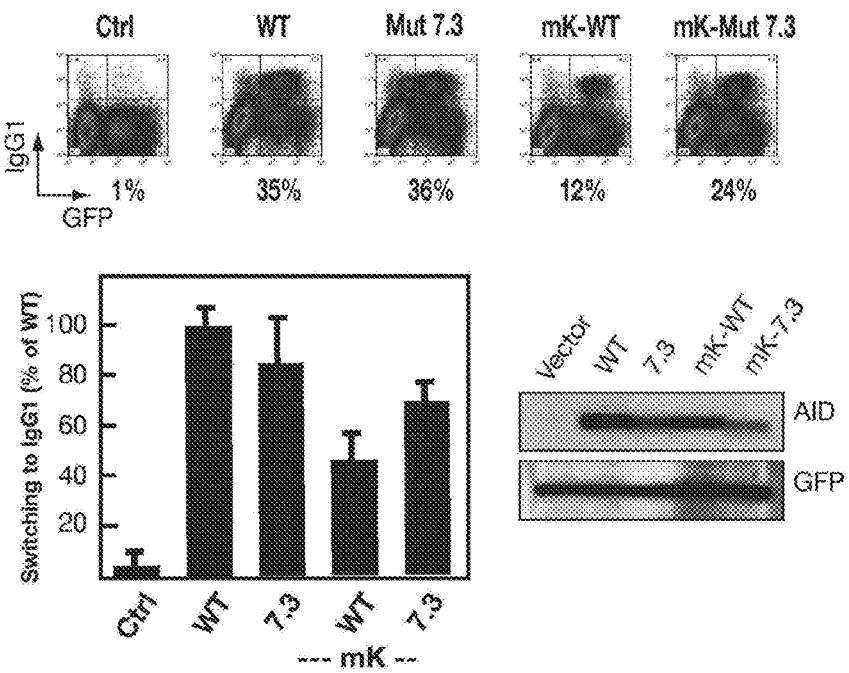

FIG. 8

| Species | Common name | Protein | Accession number/ Ensembl ID |
|---|---|---|---|
| Homo sapiens | Human | A3A (A3Z1) | NM_145699 |
| Homo sapiens | Human | A3B (A3Z2-Z1) | NM_004900 |
| Homo sapiens | Human | A3C (A3Z2) | NM_014508 |
| Homo sapiens | Human | A3DE (A3Z2-Z2) | NM_152426 |
| Homo sapiens | Human | A3F (A3Z2-Z2) | NM_145298 |
| Homo sapiens | Human | A3G (A3Z2-Z1) | NM_021822 |
| Homo sapiens | Human | A3H (A3Z3) | NM_181773 |
| Macaca mulatta | Macaque | A3A (A3Z1) | ENSMMUG00000019046 |
| Macaca mulatta | Macaque | A3B (Z2Z1) | XM_001117049 XM_001117028 |
| Macaca mulatta | Macaque | A3C (A3Z2) | NM_001114359 |
| Macaca mulatta | Macaque | A3DE (A3Z2-Z2) | XM_001094328 |
| Macaca mulatta | Macaque | A3F (A3Z2-Z2) | NM_001042373 |
| Macaca mulatta | Macaque | A3G (A3Z2-Z1) | XM_001094452 |
| Macaca mulatta | Macaque | A3H (A3Z3) | XM_001096739 |
| Bos taurus | Cow | A3Z1 | EU864534 |
| Bos taurus | Cow | A3Z2 | EU864535 |
| Bos taurus | Cow | A3Z3 | EU864536 |
| Ovis aries | Sheep | A3Z1 | EU864541 |
| Ovis aries | Sheep | A3Z2 | EU864542 |
| Ovis aries | Sheep | A3Z3 | EU864543 |
| Sus scrofa | Pig | A3Z2 | EU864539 |
| Sus scrofa | Pig | A3Z3 | EU864540 |
| Tayssu tajacu | Peccary | A3Z2-Z3 | EU864537 |
| Equus caballus | Horse | A3Z1 | XM_001499871 |
| Equus caballus | Horse | A3Z2 | XM_001501833 |
| Equus caballus | Horse | A3Z3 | XM_001501833 |
| Felis catus | Cat | A3Z2-Z3 | EF173021 |
| Canis lupus | Dog | A3Z1 | XM_847690 |
| Canis lupus | Dog | A3Z2 | AACN010393938 |
| Canis lupus | Dog | A3Z3 | XM_538369 |
| Mus musculus | Mouse | A3Z2-Z3 | NM_030255 |
| Rattus norvegicus | Rat | A3Z2-Z3 | NM_001033703 |
| Homo sapiens | Human | AID | NM_020661 |
| Macaca mulatta | Macaque | AID | XM_001113641 |
| Bos taurus | Cow | AID | NM_001038682 |
| Ovis aries | Sheep | AID | EE793762 |
| Sus scrofa | Pig | AID | BP157753 |
| Tayssu tajacu | Peccary | AID | EU864538 |
| Equus caballus | Horse | AID | XM_001493186 |
| Felis catus | Cat | AID | ENSFCAG00000006052 |
| Canis lupus | Dog | AID | NM_001003380 |
| Mus musculus | Mouse | AID | NM_009645 |
| Rattus norvegicus | Rat | AID | XM_001060382 |

FIG. 10a

```
MutE
        ATGGACTACAAAGATGACGATGATAAAGGTCCAAGAAGAAGAGAAAGGTAGACTCTCTCCTCAT
GAAGCAGAGAAAGTT         80
Mut 7.3E
        ATGGACTACAAAGATGACGATGATAAAGGTCCAAGAAGAAGAGAAAGGTAGACTCTCTCCTCAT
GAAGCAGAGAGAGTT         80
Human 7.3   ------------------------------------------------
ATGGACAGCCTCTTGATGAACCGGAGGGAGTT        32

MutE
        TCTCTACCACTTCAAGAACGTCAGATGGGCCAAGGGGAGACATGAGACCTATCTCTGTTACGTCG
TCAAGAGGAGAGACT         160
Mut 7.3E
        TCTCTACCACTTCAAGAACGTCAGATGGGCCAAGGGGAGACATGAGACCTATCTCTGTTACGTCG
TCAAGAGGAGAGACT         160
Human 7.3
        TCTTTACCAATTCAAAAATGTCCGCTGGGCTAAGGGTCGGCGTGAGACCTACCTGTGCTACGTAG
TGAAGAGGCGTGACA         112

MutE
        CAGCCACCTCTTTCTCCCTCGACTTTGGGCATCTCCGGAACAAGTCTGGGTGTCATGTCGAACTC
CTCTTCCTCCGCTAT         240
Mut 7.3E
        CAGCCACCTCTTTCTCCCTCGACTTTGGGCATCTCCGGAACAAGTCTGGGTGTCATGTCGAACTC
CTCTTCCTCCGCTAT         240
Human 7.3
        GTGCTACATCCTTTTCACTGGACTTTGGTTATCTTCGCAATAAGAACGGCTGCCACGTGGAATTG
CTCTTCCTCCGCTAC         192

MutE
        ATCTCAGACTGGGACCTCGACCCCGGGAGATGCTATAGAGTCACTTGGTTTACCTCTTGGTCCCC
CTGTTATGACTGCGC         320
Mut 7.3E
        ATCTCAGACTGGGACCTCGACCCCGGGAGATGCTATAGAGTCACTTGGTTTATCTCTTGGTCCCC
CTGTTATGACTGCGC         320
Human 7.3
        ATCTGGACTGGGACCTAGACCCTGGCCGCTGCTACCGCGTCACCTGGTTCATCTCCTGGAGCCC
CTGCTACGACTGTGC         272

MutE
        CAGACATGTCGCCGACTTCCTCAGGGGGTATCCCAATCTCTCCCTCCGCATATTCGCCGCCCGAC
TCTATTTTTGTGAGG         400
Mut 7.3E
        CAGACATGTCGCCGACTTCCTCAGGGGGTATCCCAATCTCTCCCTCCGCATATTCGCCGCCCGAC
TCTATTTTTGTGAGG         400
Human 7.3
        CCGACATGTGGCCGACTTTCTGCGAGGGAACCCCAACCTCAGTCTGAGGATCTTCACCGCGCGCC
TCTACTTCTGTGAGG         352
```

FIG. 10a (Continued)

```
MutE
        ACAGGAAAGCCGAGCCCGAGGGGCTCAGGAGACTCCACCGGGCCGGGGTCCAGATCGCCATCATG
ACATTTAAGGACTAT     480
Mut 7.3E
        ACAGGAAAGCCGAGCCCGAGGGGCTCAGGAGACTCCACCGGGCCGGGGTCCAGATCGCCATCATG
ACATTTAAGGACTAT     480
Human 7.3
        ACCGCAAGGCTGAGCCCGAGGGGCTGCGGCGGCTGCACCGCGCCGGGGTGCAAATAGCCATCATG
ACCTTCAAAGATTAT     432

MutE
        TTCTATTGTTGGAATACATTTGTCGAGAATCGGGAGAAGACTTTCAAAGCCTGGGAGGGGCTCCA
TGAGAACTCTGTCAG     560
Mut 7.3E
        TTCTATTGTTGGAATACATTTGTCGAGAATCGGGGGAAGACTTTCAAAGCCTGGGAGGGGCTCCA
TGAGAACTCTGTCAG     560
Human 7.3
        TTTTACTGCTGGAATACTTTTGTAGAAAACCACGGAAGAACTTTCAAAGCCTGGGAAGGGCTGCA
TGAAAATTCAGTTCG     512

MutE
        ACTCTCTAGGCAGCTCAGGAGAATCCTCCTCCCCCTCTATGAGGTCGAAGAACTCAGAGAAGCCT
TCCGGATCCTCGGGG     640
Mut 7.3E
        ACTCTCTAGGCAGCTCAGGAGAATCCTCCTCCCCCTCTATGAGGTCGAAGAACTCAGAGAAGCCT
TCCGGATCCTCGGGG     640
Human 7.3
        TCTCTCCAGACAGCTTCGGCGCATCCTTTTGCCCCTGTATGAGGTTGATGACTTACGAGACGCAT
TTCGTACTTTGGGAC     592

MutE       CTTGA    645 (SEQ ID NO: 88)
Mut 7.3E   CTTGA    645 (SEQ ID NO: 89)
Human 7.3  TTTGA    597 (SEQ ID NO: 90)
```

FIG. 10b

```
MutE
      MDYKDDDDKGPKKKRKVDSLLMKQRKFLYHFKNVRWAKGRHETYLCYVVKRRDSATSFSLDFGHL
RNKSGCHVELLFLRY    238
Mut 7.3E
      MDYKDDDDKGPKKKRKVDSLLMKQREFLYHFKNVRWAKGRHETYLCYVVKRRDSATSFSLDFGHL
RNKSGCHVELLFLRY    238
Human 7.3  ----------------
MDSLLMNRREFLYQFKNVRWAKGRRETYLCYVVKRRDSATSFSLDFGYLRNKNGCHVELLFLRY
190

MutE
      ISDWDLDPGRCYRVTWFTSWSPCYDCARHVADFLRGYPNLSLRIFAARLYFCEDRKAEPEGLRRL
HRAGVQIAIMTFKDY    478
Mut 7.3E
      ISDWDLDPGRCYRVTWFISWSPCYDCARHVADFLRGYPNLSLRIFAARLYFCEDRKAEPEGLRRL
HRAGVQIAIMTFKDY    478
Human 7.3
      ISDWDLDPGRCYRVTWFISWSPCYDCARHVADFLRGNPNLSLRIFTARLYFCEDRKAEPEGLRRL
HRAGVQIAIMTFKDY    430

MutE       FYCWNTFVENRKKTFKAWEGLHENSVRLSRQLRRILLPLYEVEELREAFRILGA
643 (SEQ ID NO: 91)
Mut 7.3    FYCWNTFVENRGKTFKAWEGLHENSVRLSRQLRRILLPLYEVEELREAFRILGA
643 (SEQ ID NO: 92)
Human 7.3  FYCWNTFVENHGRTFKAWEGLHENSVRLSRQLRRILLPLYEVDDLRDAFRTLGL
595 (SEQ ID NO: 93)
```

US 9,683,226 B2

MUTANTS OF ACTIVATION-INDUCED CYTIDINE DEAMINASE (AID) AND METHODS OF USE

CROSS-REFERENCE TO RELATED APPLICATIONS

This patent application claims the benefit of U.S. Provisional Patent Application No. 61/166,349, filed Apr. 3, 2009, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 140,103 Byte ASCII (Text) file named "SequenceListing.TXT," created on Apr. 1, 2010.

BACKGROUND OF THE INVENTION

Natural mechanisms for generating antibody diversification exploit the process of somatic hypermutation (SHM) to trigger the evolution of immunoglobulin variable regions, thereby rapidly generating the secondary antibody repertoire associated with the humoral response. In vivo, SHM represents a highly efficient process, which is capable of rapidly exploring productive folding structures and evolving high affinity antibodies in a manner that represents the natural process for antibody optimization. Thus, there has been significant interest to try to replicate SHM in vitro to create a simple, robust process that would be capable of mimicking the natural processes of affinity maturation directly within a mammalian cellular context to select and evolve antibodies that are immunogenically tolerated, and highly expressed in mammalian cells (Cumbers et al., *Nat. Biotechnol.*, 20(11): 1129-1134 (2002); Wang et al., *Prot. Eng. Des. Sel.*, 17(9): 569-664 (2004); Wang et al., *Proc. Natl. Acad. Sci. USA.*, 101(48): 16745-16749 (2004); Ruckerl et al., *Mol. Immunol.*, 43 (10): 1645-1652 (2006); Todo et al., *J. Biosci. Bioeng.*, 102(5): 478-81 (2006); Arakawa et al., *Nucleic Acids Res.*, 36(1): e1 (2008)).

However, native antibodies that have been isolated from an individual human or animal often fail to demonstrate optimal affinity properties because an intrinsic affinity ceiling inherent in the immune system prevents the in vivo discrimination—and thus selection—of antibodies with affinities more potent than about 100 pM (Batista and Neuberger, *Immunity*, 8(6): 751-91998, (1998) and *EMBO J.*, 19(4): 513-20 (2000).

The use of phage display libraries can address some of these issues, and phage display based approaches have been shown to be capable of routinely producing high affinity antibodies. However, from a theoretical perspective, such static libraries are inherently limited in their size and scope, because even the largest ($10^{12}$) libraries can explore only a small fraction of the potential innate immune repertoire. Furthermore it is not possible to simultaneously co-evolve antibodies via phage display approaches on the basis of both good mammalian expression and high affinity, leading to potential downstream manufacturing issues that result from otherwise poor expression in mammalian host cells. Additionally, the use of random mutagenesis in combination with phage display lacks the inherent selectivity profiling found in natural processes of antibody affinity maturation, often resulting in issues of human anti-human immunity, or undesirable cross reactivity profiles.

The use of a cultured cell line to evolve an antibody to a specific target antigen using somatic hypermutation in vitro was first demonstrated using the human Burkitt lymphoma cell line, Ramos (Cumbers et al., *Nat. Biotechnol.*, 20(11): 1129-1134 (2002)). Ramos, and other B cell lines, have also been used successfully to evolve non antibody genes that have been randomly integrated in to the host cell's chromosomal DNA (Wang et al., *Prot. Eng. Des. Sel.*, 17(9): 569-664 (2004) and *Proc. Natl. Acad. Sci. USA.*, 101(48): 16745-16749 (2004)). Additionally, efficient somatic hypermutation has been demonstrated on non antibody genes in B cell lines using episomal vectors, either with or without Ig specific cis regulatory elements (Ruckerl et al., *Mol. Immunol.*, 43 (10): 1645-1652 (2006)). Although some Ramos cell lines show relatively high rates of constitutive hypermutation, B cell lines in general display relatively slow rates of cell division and are difficult to transfect with high efficiency, which limits their practical utility for directed evolution.

The chicken bursal cell line, DT40, diversifies its rearranged Ig light gene by pseudo V gene template gene conversion. However, if gene conversion is blocked by the deletion of the Rad51 paralog, XRCC2 (Sale et al., *Nature*, 412: 921-6 (2001)), or the deletion of the pseudogene conversion donors (Arakawa et al., *Nucleic Acids Res.*, 36(1): e1 (2008)), the cell line displays constitutive hypermutation in culture. By comparison to Ramos cells, DT40 cells have a significantly shorter generation time (12 hours), are amenable to directed gene targeting and have been successfully used for directed evolution of both endogenous antibodies (Seo et al., *Nat. Biotechnol.*, 23(6): 731-5 (2005); *Nat. Protoc.*, 1(3): 1502-6 (2006); *Biotechnol. Genet. Eng. Rev.*, 24: 179-93 (2007); Todo et al., *J. Biosci. Bioeng.*, 102(5): 478-81 (2006)), and non antibody proteins (Arakawa et al., *Nucleic Acids Res.*, 36(1): e1 (2008)).

While B-cell derivatives such as Ramos and DT40 have been successfully used for directed evolution, the reliable use of these cells in a robust process for directed evolution is complicated by a number of factors including: (i) the need to insert the gene of interest into a defined site in the host cell's Ig locus in order to achieve high level mutagenesis (Parsa et al., *Mol. Immunol.*, 44(4): 567-75 (2007), and (ii) the complex natural biology of somatic hypermutation acting at the endogenous immunoglobulin loci in these cells. Additionally such engineered cell lines exhibit significant clonal instability in SHM rates (Zhang et al., *Int. Immunol.*, 13: 1175-1184 (2001), Martin et al., *Proc. Natl. Acad. Sci. USA.*, 99(19): 12304-12308 (2002) and *Nature*, 415(6873): 802-806 (2002); Ruckerl et al., *Mol. Immunol.*, 41: 1135-1143 (2004)), and do not provide for any simple means to regulate or control hypermutation, i.e. to switch off mutagenesis after selection of a desired phenotype has been achieved.

The use of non B cells to initiate targeted somatic hypermutation in a gene of interest has been successfully described by a number of groups (Martin et al., *Proc. Natl. Acad. Sci. USA.*, 99(19): 12304-12308 (2002) and *Nature*, 415(6873): 802-806 (2002); McBride et al., *Proc. Natl. Acad. Sci. USA*, 103(23): 8798-803 (2006); Jovanic et al., *PLoS ONE*, 23; 3(1): e1480 (2008); U.S. patent application Ser. No. 09/075,378; International Patent Application Publications WO 08/103474A1 and WO 08/103475A1), and these cell lines can also provide for efficient gene transfer, high level protein expression, optimal growth characteristics and are readily amenable to suspension culture and flow cytometry.

Activation-induced cytidine deaminase (AID) belongs to the APOBEC family of cytidine deaminase enzymes. AID is expressed within activated B cells and is required to initiate somatic hypermutation (Muramatsu et al., *Cell*, 102(5): 553-63 (2000); Revy et al., *Cell*, 102(5): 565-75 (2000); Yoshikawa et al., *Science*, 296(5575): 2033-6 (2002)) by creating point mutations in the underlying DNA encoding antibody genes (Martin et al., *Proc. Natl. Acad. Sci. USA.*, 99(19): 12304-12308 (2002) and *Nature*, 415(6873): 802-806 (2002); Petersen-Mart et al., *Nature*, 418(6893): 99-103 (2002)). AID is also an essential protein factor for class switch recombination and gene conversion (Muramatsu et al., *Cell*, 102(5): 553-63 (2000); Revy et al., *Cell*, 102(5): 565-75 (2000)).

The discovery that AID is responsible for initiating somatic hypermutation has opened the possibility of using non B cell lines to create more defined, stable and controllable systems for utilizing somatic hypermutation.

Despite these advances, key challenges regarding the development of a practical system for somatic hypermutation remain, including (1) the ability to target somatic hypermutation to a gene of interest, and away from structural genes, (2) the relatively low rates and nature of the mutations achieved using exogenous AID compared to somatic hypermutation in vivo, and (3) the relatively long cell doubling times required to grow up a cell population from a single cell clone between cycles of mutagenesis.

Thus, there is a specific need for improved compositions and methods to improve the efficiency of somatic hypermutation systems. This invention provides such compositions and methods.

BRIEF SUMMARY OF THE INVENTION

The invention provides an isolated or purified nucleic acid molecule comprising a nucleotide sequence encoding a functional mutant activation-induced cytidine deaminase (AID) protein whose amino acid sequence differs from the amino acid sequence of a human AID protein (SEQ ID NO: 1 or SEQ ID NO: 2) by at least one amino acid substitution.

In one embodiment, the amino acid sequence of the functional mutant AID protein differs from the amino acid sequence of a human AID protein (SEQ ID NO: 1 or SEQ ID NO: 2) by at least one amino acid substitution at a residue selected from the group consisting of residue 34, residue 82, and residue 156.

In another embodiment, the amino acid sequence of the functional mutant AID protein differs from the amino acid sequence of a human AID protein (SEQ ID NO: 1 or SEQ ID NO: 2) by at least one amino acid substitution at residue 10 and at least one amino acid substitution at residue 156.

In yet another embodiment, the amino acid sequence of the functional mutant AID protein differs from the amino acid sequence of a human AID protein (SEQ ID NO: 1 or SEQ ID NO: 2) by at least one amino acid substitution at residue 35 and at least one amino acid substitution at residue 145.

In a further embodiment, the amino acid sequence of the functional mutant AID protein differs from the amino acid sequence of a human AID protein (SEQ ID NO: 1 or SEQ ID NO: 2) by at least one amino acid substitution at residue 34 and at least one amino acid substitution at residue 160.

In another embodiment, the amino acid sequence of the functional mutant AID protein differs from the amino acid sequence of a human AID protein (SEQ ID NO: 1 or SEQ ID NO: 2) by at least one amino acid substitution at residue 43 and at least one amino acid substitution at residue 120.

The invention also provides an isolated or purified nucleic acid molecule comprising a nucleotide sequence encoding a functional mutant AID protein whose amino acid sequence differs from the amino acid sequence of a human AID protein (SEQ ID NO: 1 or SEQ ID NO: 2) by at least two amino acid substitutions, wherein at least one substitution is at residue 57 and at least one substitution is at residue 145 or 81, and wherein the functional mutant AID protein has at least a 10-fold improvement in activity compared to the human AID protein in a bacterial papillation assay.

In still another embodiment, the amino acid sequence of the functional mutant AID protein differs from the amino acid sequence of a human AID protein (SEQ ID NO: 1 or SEQ ID NO: 2) by at least one amino acid substitution at residue 156 and at least one amino acid substitution at residue 82.

In a further embodiment, the amino acid sequence of the functional mutant AID protein differs from the amino acid sequence of a human AID protein (SEQ ID NO: 1 or SEQ ID NO: 2) by at least one amino acid substitution at residue 156 and at least one amino acid substitution at residue 34.

In a further embodiment, the amino acid sequence of the functional mutant AID protein differs from the amino acid sequence of a human AID protein (SEQ ID NO: 1 or SEQ ID NO: 2) by at least one amino acid substitution at residue 156 and at least one amino acid substitution at residue 157.

In yet another embodiment, the amino acid sequence of the functional mutant AID protein differs from the amino acid sequence of a human AID protein (SEQ ID NO: 1 or SEQ ID NO: 2) by at least one amino acid substitution at residues 10, 82, and 156.

The invention also provides an isolated or purified nucleic acid molecule comprising a nucleotide sequence encoding a functional mutant activation-induced cytidine deaminase (AID) protein whose amino acid sequence differs from an amino acid sequence selected from the group of a canine AID protein (SEQ ID NO: 3), murine AID protein (SEQ ID NO: 4), rat AID protein (SEQ ID NO: 5), bovine AID protein (SEQ ID NO: 6), and chicken AID protein (SEQ ID NO: 7) by at least one amino acid substitution at a residue selected from the group consisting of residue 34, residue 82, and residue 156, wherein the functional mutant AID protein has at least a 10-fold improvement in activity compared to the human AID protein in a bacterial papillation assay.

Further provided is an expression vector comprising a nucleic acid molecule comprising a nucleotide sequence encoding a functional mutant activation-induced cytidine deaminase (AID).

The invention also provides an isolated cell comprising the nucleic acid molecule encoding a functional mutant AID protein.

Further provided is a transgenic animal comprising the nucleic acid molecule encoding a functional mutant AID protein.

The invention also provides a method for preparing a gene product having a desired property, which method comprises expressing a nucleic acid encoding the gene product in a population of cells, wherein the population of cells expresses, or can be induced to express, a functional mutant AID protein, whereupon expression of the functional mutant AID protein induces a mutation in the nucleic acid encoding the gene product.

Further provided is a method for mutating an organism to have a desired phenotype comprising expressing, or inducing the expression of, a functional mutant AID protein in the organism, whereupon expression of the functional mutant AID protein induces a mutation within the chromosomal DNA of the organism.

BRIEF DESCRIPTION OF THE DRAWINGS

FIG. 2 is a chart that illustrates select human functional AID mutants identified in papillation screens. The numbers depict the mean frequency of mutation to Rif$^r$ of each human AID mutant relative to vector.

FIG. 3a is a sequence diagram of human AID (SEQ ID NO: 2) that illustrates the positions and identities of the functional mutations that were identified in human and pufferfish AID. FIG. 3b compares the expression level of GST-AID mutant fusion proteins by Western blot. FIGS. 3c,d are graphs which quantify the deaminase activity and target specificity of GST-AID mutant fusion proteins.

FIG. 4a is a chart that illustrates select pufferfish AID mutants identified in papillation screens. FIG. 4b is a bar graph that compares the relative mutation frequency of pufferfish AID mutants to Rif$^r$ at 18° C. and 37° C.

FIG. 5a includes flow cytometry plots of IgM and GFP expression in individual DT40 clones expressing the indicated AID protein. FIG. 5a also contains a graph of IgM loss in 12 independent clonal transfectants expressing the indicated protein. FIG. 5b contains a diagram of the distribution of the IgVλ mutations observed in transfected DT40 cells. FIG. 5b also contains pie charts depicting the number of IgVλ mutations after sorting for IgM loss. FIG. 5b also shows AID expression by Western blot. FIG. 5c includes flow cytometry plots of switching to IgG1 in AID-deficient B cells transduced with the indicated retrovirus. The bar graph in FIG. 5c quantifies IgG1 switching relative to wild-type AID, and the Western blot in FIG. 5c shows AID expression by Western blot.

FIG. 6 further provides a Southern blot of c-myc-IgH translocations derived from chromosomes 15 and 12 after amplification by PCR of genomic DNA from AID-deficient B cells transduced with the indicated retrovirus.

FIG. 8 lists the GenBank/Ensembl accession numbers of the mammalian AID and APOBEC3 sequences used to generate FIG. 7.

FIG. 10a is a nucleic acid sequence alignment of AID sequences used in 293-c18 cell experiments described in Example 14. Boxed residues indicate changes between wt and 7.3 mutant sequences. FIG. 10b is an amino acid sequence alignment of AID sequences used in the 293-c18 cell experiments described in Example 14. Boxed residues indicate changes between wt and 7.3 mutant sequences. The L to A mutation in MutE and Mut 7.3 disables the function of the nuclear export signal. A period indicates a stop codon, and a dash specifies positions where there is no corresponding amino acid.

DETAILED DESCRIPTION OF THE INVENTION

Figure 1:
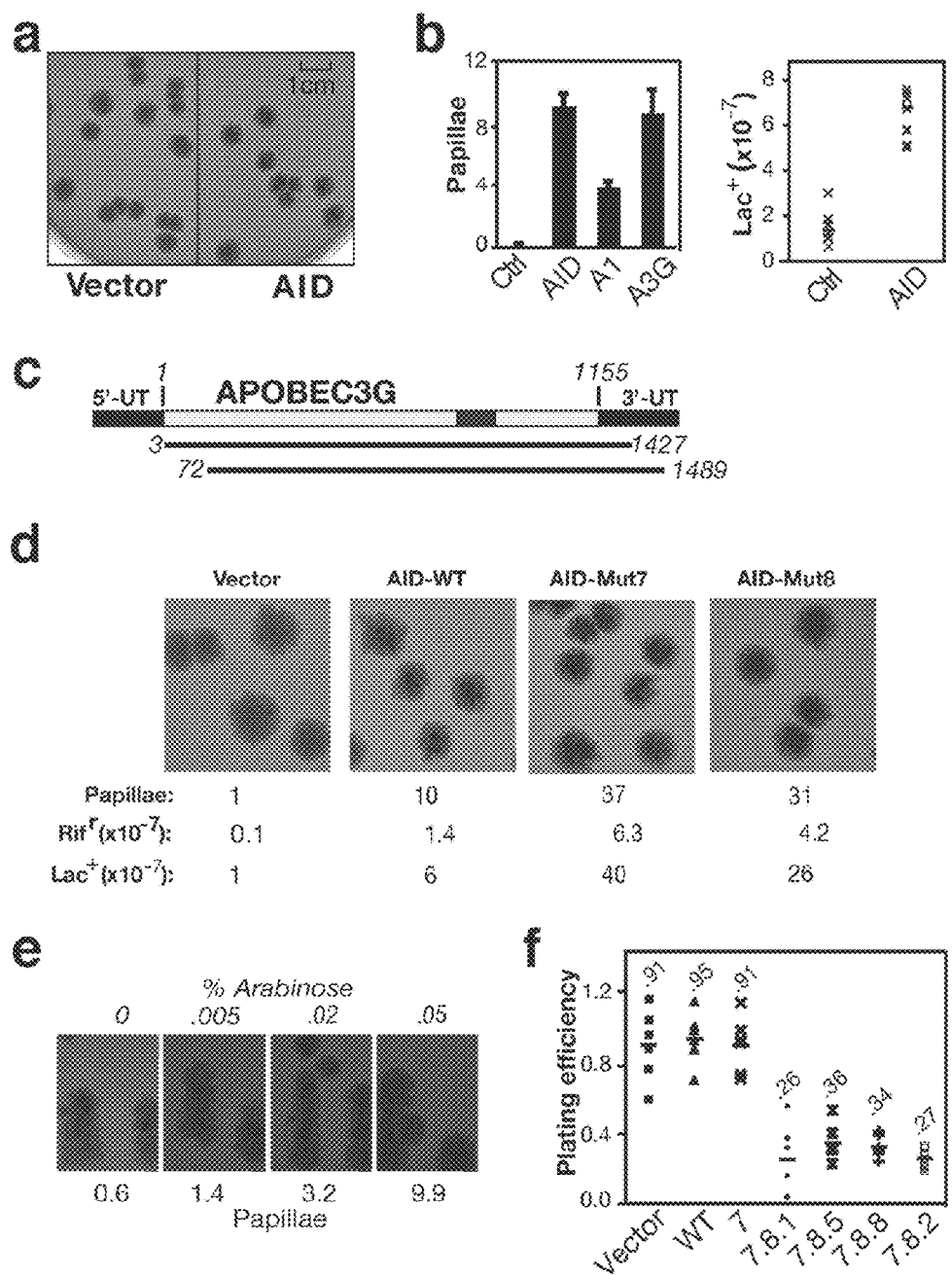
FIG. 1a includes images of papillae in bacterial colonies expressing or not expressing human AID.
FIG. 1b is a bar graph quantifying the papillae in bacterial colonies expressing human AID, APOBEC1 (A1), or APOBEC3G (A3G).
FIG. 1c is a diagram depicting the two APOBEC3G cDNAs obtained by screening a human spleen cDNA library for papillae.
FIG. 1d includes images of papillae in bacterial colonies expressing the indicated AID protein and lists the mutation frequencies relative to vector.
FIG. 1e includes images of papillation by AID Mut1.1 as a function of arabinose concentration.
FIG. 1f is a graph depicting the plating efficiency of human AID mutants.

The invention provides an isolated or purified nucleic acid molecule comprising a nucleotide sequence encoding a functional mutant AID protein whose amino acid sequence differs from the amino acid sequence of a human AID protein (SEQ ID NO: 1 or SEQ ID NO: 2) by at least one amino acid substitution, wherein the functional mutant AID protein has at least a 10-fold improvement in activity compared to the human AID protein in a bacterial papillation assay.

"Nucleic acid molecule" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

The term "nucleotide" as used herein refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates and the like).

The terms "synthetic polynucleotide," "synthetic gene" or "synthetic polypeptide," as used herein, mean that the corresponding polynucleotide sequence or portion thereof, or amino acid sequence or portion thereof, is derived from a sequence that has been designed, or synthesized de novo, or modified, compared to the equivalent naturally occurring sequence. Synthetic polynucleotides or synthetic genes can be prepared by methods known in the art, including but not limited to, the chemical synthesis of nucleic acid or amino acid sequences or amplified via PCR (or similar enzymatic amplification systems). Synthetic genes are typically different from unmodified genes or naturally occurring genes, either at the amino acid level or polynucleotide level (or both) and are typically located within the context of synthetic expression control sequences. For example, synthetic gene sequences may include amino acid or polynucleotide sequences that have been changed, for example, by the replacement, deletion, or addition, of one or more, amino acids, or nucleotides, thereby providing an amino acid sequence, or a polynucleotide coding sequence that is different from the source sequence. Synthetic gene or polynucleotide sequences may not necessarily encode proteins with different amino acids, compared to the natural gene. For example, they can also encompass synthetic polynucleotide sequences that incorporate different codons but which encode the same amino acid; i.e., the nucleotide changes represent silent mutations at the amino acid level. In one embodiment, synthetic genes exhibit altered susceptibility to SHM compared to the naturally occurring or unmodified gene. Synthetic genes can be iteratively modified using the methods described herein and, in each successive iteration, a corresponding polynucleotide sequence or amino acid sequence, is derived, in whole or part, from a sequence that has been designed, or synthesized de novo, or modified, compared to an equivalent unmodified sequence.

As used herein a "codon" refers to the three nucleotides which, when transcribed and translated, encode a single amino acid residue; or in the case of UUA, UGA or UAG encode a termination signal. Codons encoding amino acids are well known in the art.

Optimal codon usage is indicated by codon usage frequencies for expressed genes, for example, as shown in the codon usage chart from the program "Human-High.cod" from the Wisconsin Sequence Analysis Package, Version 8.1, Genetics Computer Group, Madison, Wis. Codon usage is also described in, for example, R. Nussinov, "Eukaryotic Dinucleotide Preference Rules and Their Implications for Degenerate Codon Usage," *J. Mol. Biol.,* 149: 125-131 (1981). The codons which are most frequently used in highly expressed human genes are presumptively the optimal codons for expression in human host cells and, thus, form the bases for constructing a synthetic coding sequence.

By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, nucleic acids will be mixed with an acceptable carrier or diluent when used for introduction into cells.

The term "activation-induced cytidine deaminase" or ("AID") refers to members of the AID/APOBEC family of RNA/DNA editing cytidine deaminases capable of mediating the deamination of cytosine to uracil within a DNA sequence. (See, e.g., Conticello et al., *Mol. Biol. Evol.,* 22: 367-377 (2005) and U.S. Pat. No. 6,815,194).

The term "wild-type AID" refers to a naturally occurring amino acid sequence of an AID protein. Suitable wild-type AID proteins include all vertebrate forms of AID, including, for example, primate, rodent, avian and bony fish. Representative examples of wild-type AID amino acid sequences include without limitation, human AID (SEQ ID NO: 1 or SEQ ID NO: 2), canine AID (SEQ ID NO: 3), murine AID (SEQ ID NO: 4), rat AID (SEQ ID NO: 5), bovine AID (SEQ ID NO: 6), chicken AID (SEQ ID NO: 7), porcine AID (SEQ ID NO: 8), chimp AID (SEQ ID NO: 9), macaque AID (SEQ ID NO: 10), horse AID (SEQ ID NO: 11), *Xenopus* AID (SEQ ID NO: 12), pufferfish (fugu) AID (SEQ ID NO: 13), and zebrafish (SEQ ID NO: 14).

The term "AID homolog" refers to the enzymes of the Apobec family and include, for example, Apobec-1, Apobec3C or Apobec3G (described, for example, in Jarmuz et al., *Genomics,* 79: 285-296 (2002)). The term "AID activity" includes activity mediated by AID and AID homologs.

An "AID mutant" or a "mutant of AID," as used herein, refers to an AID amino acid sequence that differs from a wild-type AID amino acid sequence by at least one amino acid. A wild-type amino acid sequence can be mutated to produce an AID mutant by any suitable method known in the art, such as, for example, by insertion, deletion and/or substitution. For example, mutations may be introduced into a nucleic acid sequence encoding wild-type AID randomly or in a site-specific manner. Random mutations may be generated, for example, by error-prone PCR of an AID template sequence. A preferred means for introducing random mutations in is the Genemorph II Random Mutagenesis Kit (Stratagene, LaJolla, Calif.). Site-specific mutations can be introduced, for example, by ligating into an expression vector a synthesized oligonucleotide comprising the modified site. Alternately, oligonucleotide-directed site-specific mutagenesis procedures can be used, such as those disclosed in Walder et al., *Gene,* 42: 133 (1986); Bauer et al., *Gene,* 37: 73 (1985); Craik, *Biotechniques,* 12-19 (January 1995); and U.S. Pat. Nos. 4,518,584 and 4,737,462. A preferred means for introducing site-specific mutations is the QuikChange Site-Directed Mutagenesis Kit (Stratagene, LaJolla, Calif.).

The terms "functional mutant of AID," "functional AID mutant," or "functional mutant AID protein," each refer to a mutant AID protein which retains all or part of the biological activity of a wild-type AID, or which exhibits increased biological activity as compared to a wild-type AID protein. The biological activity of a wild-type AID includes, but is not limited to, the deamination of cytosine to uracil within a DNA sequence, papillation in a bacterial mutagenesis assay, somatic hypermutation of a target gene, and immunoglobulin class switching. A mutant AID protein can retain any part of the biological activity of a wild-type AID protein. Desirably, the mutant AID protein retains at least 75% (e.g., 75%, 80%, 90% or more) of the biological activity of wild-type AID. Preferably, the mutant AID protein retains at least 90% (e.g., 90%, 95%, 100% or more) of the biological activity of wild-type AID.

In a preferred embodiment, the mutant AID protein exhibits increased biological activity as compared to a wild-type AID protein. In this respect, the functional AID mutant has at least a 10-fold improvement in activity compared to a wild-type AID protein as measured by a bacterial papillation assay. Bacterial papillation assays are known in the art as useful for screening for *E. Coli* mutants that are defective in some aspect of DNA repair (Nghiem et al., *Proc. Natl. Acad. Sci. USA,* 85: 2709-2713 (1988) and Ruiz et al., *J. Bacteriol.,* 175: 4985-4989 (1993)). The bacterial papillation assay can employ *Escherichia coli* CC102 cells harboring a missense mutation within the lacZ gene. *E. Coli* CC102 cells give rise to white colonies on MacConkey-lactose plates. Within such white colonies, a small number of red microcolonies, or "papilli," can often be discerned (typically 0-2 per colony), which reflect spontaneously-arising Lac$^+$ revertants. Bacterial clones which exhibit an elevated frequency of spontaneous mutation (i.e., "mutator clones") can be identified by virtue of an increased number of papilli. Bacterial papillation assays can be used to screen for functional AID mutants having increased activity as compared to wild-type AID. Bacterial papillation assays are described in detail in the Examples.

In one embodiment, the functional AID mutant has at least a 10-fold (e.g., 10-fold, 30-fold, 50-fold or more) improvement in activity compared to the wild-type AID protein in a bacterial papillation assay. Preferably, the functional AID mutant has at least a 100-fold (e.g., 100-fold, 200-fold, 300-fold or more) improvement in activity compared to wild-type AID. More preferably, the functional AID mutant has at least a 400-fold (e.g., 400-fold, 500-fold, 1000-fold or more) improvement in activity compared to wild-type AID.

The functional mutant AID protein comprises an amino acid sequence which differs from the amino acid sequence of a wild-type AID protein by at least one amino acid substitution. The wild-type AID protein can be any vertebrate AID protein, including those described herein. Desirably, the wild-type AID protein is a human AID protein, of which there are at least two known variants (i.e., SEQ ID NO: 1 and SEQ ID NO: 2). Additional vertebrate AID proteins include, without limitation, canine AID (SEQ ID NO: 3), murine AID (SEQ ID NO: 4), rat AID (SEQ ID NO: 5), bovine AID (SEQ ID NO: 6), chicken AID (SEQ ID NO: 7), porcine AID (SEQ ID NO: 8), chimp AID (SEQ ID NO: 9), macaque AID (SEQ ID NO: 10), horse AID (SEQ ID NO: 11), *Xenopus* AID (SEQ ID NO: 12), pufferfish (fugu) AID (SEQ ID NO: 13), or zebrafish (SEQ ID NO: 14).

One of ordinary skill in the art will appreciate that although there is a high degree of homology among the vertebrate AID proteins, there is a variable number of amino acid substitutions, deletions, and insertions in each of the vertebrate AID protein relative to human AID (SEQ ID NO: 1 or SEQ ID NO: 2). As such, the present invention encompasses the mutations described herein when incorporated at the analogous position of any vertebrate AID protein. One of ordinary skill in the art can determine the analogous position in any vertebrate AID protein by performing a sequence alignment of the homologous vertebrate AID protein with that of human AID (SEQ ID NO: 1 or SEQ ID NO: 2) using any computer based alignment program known in the art (e.g., BLAST or ClustalW2).

A wild-type AID protein typically contains a nuclear export sequence near the C-terminus of the protein. In one embodiment of the invention, a residue or a plurality of residues that mediate nuclear export of wild-type AID may be mutated, and a functional mutant AID protein may be generated comprising an amino acid sequence which differs from the amino acid sequence of an AID protein having a mutated nuclear export sequence by at least one additional amino acid substitution. Examples of canine AID proteins having a mutated nuclear export sequence that may serve as a reference sequence into which a mutation(s) identified herein as producing a functional AID mutant may be inserted include a L198A mutant (SEQ ID NO: 70) and a D187E, D188E, D191E, T195I, and L198A mutant (SEQ ID NO: 71).

An amino acid "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine and isoleucine, the "aliphatic slightly-polar sub-group" consists of methionine, serine, threonine, and cysteine, the "aliphatic polar/charged sub-group" consists of glutamic acid, aspartic acid, asparagine, glutamine, lysine, and arginine, and the "small-residue sub-group" consists of glycine and alanine. The group of charged/polar amino acids may be sub-divided into three sub-groups: the "positively-charged sub-group," consisting of lysine and arginine, the "negatively-charged sub-group," consisting of glutamic acid and aspartic acid, and the "polar sub-group" consisting of asparagine and glutamine.

Aromatic amino acids may be sub-divided into two sub-groups: the "nitrogen ring sub-group," consisting of histidine and tryptophan and the "phenyl sub-group," consisting of phenylalanine and tyrosine.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag, New York (1979)). According to such analyses, groups of amino acids may be defined where amino acids within a group exchange preferentially with each other, and therefore resemble each other most in their impact on the overall protein structure (Schulz, G. E. and R. H. Schirmer, supra).

Examples of conservative mutations include amino acid substitutions of amino acids within the sub-groups above, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —NH$_2$ can be maintained.

"Semi-conservative mutations" include amino acid substitutions of amino acids with the same groups listed above, that do not share the same sub-group. For example, the mutation of aspartic acid for asparagine, or asparagine for lysine each involves amino acids within the same group, but different sub-groups.

"Non-conservative mutations" involve amino acid substitutions between different groups, for example lysine for tryptophan, or phenylalanine for serine, etc.

In a preferred embodiment, the nucleic acid molecule encodes a functional AID mutant whose amino acid sequence differs from the amino acid sequence of wild-type AID by at least one amino acid substitution at a residue selected from the group consisting of residue 34, residue 82, and residue 156. These residues can be substituted alone, or in any combination. In embodiments where residue 34 lysine (K) is substituted, preferably it is substituted with a glutamic acid (E) or an aspartic acid (D) residue. In embodiments where residue 82 threonine (T) is substituted, preferably it is substituted with an isoleucine (I) or a leucine (L) residue. In embodiments where residue 156 glutamic acid (E) is substituted, preferably it is substituted with a glycine (G) or an alanine (A) residue. Moreover, when amino acid residue 156 is substituted (either alone, or in combination with a substitution at residue 34 and/or residue 82), it may also be desirable to generate a functional AID mutant protein with amino acid substitutions at residues 9, 13, 38, 42, 96, 115, 132, 157, 180, 181, 183, 197, 198, or combinations thereof. In particular, (a) the amino acid substitution at residue 9 can be methionine (M) or lysine (K), (b) the amino acid substitution at residue 13 can be phenylalanine (F) or tryptophan (W), (c) the amino acid substitution at residue 38 can be glycine (G) or alanine (A), (d) the amino acid substitution at residue 42 can be isoleucine (I) or leucine (L), (e) the amino acid substitution at residue 96 can be glycine (G) or alanine (A), (f) the amino acid substitution at residue 115 can be tyrosine (Y) or tryptophan (W), (g) the amino acid substitution at residue 132 can be glutamic acid (E) or aspartic acid (D), (h) the amino acid substitution at residue 180 can be isoleucine (I) or alanine (A), (i) the amino acid substitution at residue 181 can be methionine (M) or valine (v), (j) the amino acid substitution at residue 183 can be isoleucine (I) or proline (P), (k) the amino acid substitution at residue 197 can be arginine (R) or lysine (K), (l) the amino acid substitution at residue 198 can be valine (V) or leucine (L), and (m) the amino acid substitution at residue 157 can be threonine (T) or lysine (K).

In another embodiment, the nucleic acid molecule encodes a functional AID mutant whose amino acid sequence differs from the amino acid sequence of wild-type AID by at least one amino acid substitution at residue 10 and at least one amino acid substitution at residue 156. These residues can be substituted alone, or in any combination. In embodiments where amino acid residue 10 (lysine) is substituted, preferably it is substituted with a glutamic acid (E) or aspartic acid (D) residue. In embodiments where residue 156 (glutamic acid) is substituted, preferably it is substituted with a glycine (G) or alanine (A) residue. In embodiments where the amino acids at residues 10 and 156 are substituted, it may also be desirable to include amino acid substitutions at residues 13, 34, 82, 95, 115, 120, 134, 145, or combinations thereof. In particular, (a) the amino acid substitution at residue 13 can be phenylalanine (F) or tryptophan (W), (b) the amino acid substitution at residue 34 can be glutamic acid (E) or aspartic acid (D), (c) the amino acid substitution at residue 82 can be isoleucine (I) or leucine (L), (d) the amino acid substitution at residue 95 can be serine (S) or leucine (L), (e) the amino acid substitution at residue 115 can be tyrosine (Y) or tryptophan (W), (f) the amino acid substitution at residue 120 can be arginine (R) or asparagine (N), and (g) the amino acid substitution at residue 145 can be leucine (L) or isoleucine (I).

In another embodiment, the nucleic acid molecule encodes a functional AID mutant whose amino acid sequence differs from the amino acid sequence of wild-type AID by at least one amino acid substitution at residue 35 and at least one amino acid substitution at residue 145. The amino acids at residues 35 and 145 can be substituted with any suitable amino acid. The amino acid at residue 35 preferably is substituted with glycine (G) or alanine (A). The amino acid at residue 145 preferably is substituted with leucine (L) or isoleucine (I).

In another embodiment, the nucleic acid molecule encodes a functional AID mutant whose amino acid sequence differs from the amino acid sequence of wild-type AID by at least one amino acid substitution at residue 34 and at least one amino acid substitution at residue 160. The amino acids at residues 34 and 160 can be substituted with any suitable amino acid. The amino acid at residue 34 preferably is substituted with glutamic acid (E) or aspartic acid (D). The amino acid at residue 160 preferably is substituted with glutamic acid (E) or aspartic acid (D).

In another embodiment, the nucleic acid molecule encodes a functional AID mutant whose amino acid sequence differs from the amino acid sequence of wild-type AID by at least one amino acid substitution at residue 43 and at least one amino acid substitution at residue 120. The amino acids at residues 43 and 120 can be substituted with any suitable amino acid. The amino acid at residue 43 preferably is substituted with proline (P). The amino acid at residue 120 preferably is substituted with arginine (R).

In yet another embodiment, the nucleic acid molecule encodes a functional AID mutant whose amino acid sequence differs from the amino acid sequence of wild-type AID by at least two amino acid substitutions, wherein at least one substitution is at residue 57 and at least one substitution is at residue 145 or 81. These residues can be substituted alone, or in any combination (e.g., substitution of residues 57 and 145 or substitution of residues 57 and 81). Preferably, the amino acid at residue 57 is substituted with glycine (G) or alanine (A). When the amino acid at residue 145 is substituted, preferably it is substituted with leucine (L) or isoleucine (I). When the amino acid at residue 81 is substituted, preferably it is substituted with tyrosine (Y) or tryptophan (W).

In still another embodiment, the nucleic acid molecule encodes a functional AID mutant whose amino acid sequence differs from the amino acid sequence of wild-type AID by at least one amino acid substitution at residue 156 and at least one amino acid substitution at residue 82. The amino acids at residues 156 and 82 can be substituted with any suitable amino acid. The amino acid at residue 156 preferably is substituted with glycine (G) or alanine (A). The amino acid at residue 82 preferably is substituted with leucine (L) or isoleucine (I).

In another embodiment, the nucleic acid molecule encode, s a functional AID mutant whose amino acid sequence differs from the amino acid sequence of wild-type AID by at least one amino acid substitution at residue 156 and at least one amino acid substitution at residue 34. The amino acids at residues 156 and 34 can be substituted with any suitable amino acid. The amino acid at residue 156 is substituted with glycine (G) or alanine (A). The amino acid at residue 34 preferably is substituted with glutamic acid (E) or aspartic acid (D).

In another embodiment, the nucleic acid molecule encodes a functional AID mutant whose amino acid sequence differs from the amino acid sequence of wild-type AID by at least one amino acid substitution at residue 156 and at least one amino acid substitution at residue 157. The amino acids at residues 156 and 157 can be substituted with any suitable amino acid. The amino acid at residue 156 preferably is substituted with glycine (G) or alanine (A). The amino acid at residue 120 preferably is substituted with arginine (R) or asparagine (N).

In yet another embodiment, the nucleic acid molecule encodes a functional AID mutant whose amino acid sequence differs from the amino acid sequence of wild-type AID by at least one amino acid substitution at residues 10, 82, and 156. These residues can be substituted alone, or in any combination. In a preferred embodiment, the nucleic acid molecule encodes a functional AID mutant whose amino acid sequence differs from the amino acid sequence of wild-type AID by amino acid substitutions at residues 10, 82, and 156. In embodiments where the amino acids at residues 10, 82, and 156 are substituted, it may also be desirable to include amino acid substitutions at residues 9, 15, 18, 30, 34, 35, 36, 44, 53, 59, 66, 74, 77, 88, 93, 100, 104, 115, 118, 120 142, 145, 157, 160, 184, 185, 188, 192 or combinations thereof. In particular, (a) the amino acid substitution at residue 9 can be serine (S), methionine (M), or tryptophan (W), (b) the amino acid substitution at residue 10 can be glutamic acid (E) or aspartic acid (D), (c) the amino acid substitution at residue 15 can be tyrosine (Y) or leucine (L), (d) the amino acid substitution at residue 18 can be alanine (A) or leucine (L), (e) the amino acid substitution at residue 30 can be tyrosine (Y) or serine (S), (f) the amino acid substitution at residue 34 can be glutamic acid (E) or aspartic acid (D), (g) the amino acid substitution at residue 35 can be serine (S) or lysine (K), (h) the amino acid substitution at residue 36 can be cysteine (C), (i) the amino acid substitution at residue 44 can be arginine (R) or lysine (K), (j) the amino acid substitution at residue 53 can be tyrosine (Y) or glutamine (Q), (k) the amino acid substitution at residue 57 can be alanine (A) or leucine (L), (l) the amino acid substitution at residue 59 can be methionine (M) or alanine (A), (m) the amino acid substitution at residue 66 can be threonine (T) or alanine (A), (n) the amino acid substitution at residue 74 can be histidine (H) or lysine (K), (O) the amino acid substitution at residue 77 can be serine (S) or lysine (K), (p) the amino acid substitution at residue 82 can be isoleucine (I) or leucine (L), (q) the amino acid substitution at residue 88 can be serine (S) or threonine (T), (r) the amino acid substitution at residue 93 can be leucine (L), arginine (R), or lysine (K), (s) the amino acid substitution at residue 100 can be glutamic acid (E), tryptophan (W), or phenylalanine F, (t) the amino acid substitution at residue 104 can be isoleucine (I) or alanine (A), (u) the amino acid substitution at residue 115 can be tyrosine (Y) or leucine (L), (v) the amino acid substitution at residue 118 can be glutamic acid (E) or valine (V), (x) the amino acid substitution at residue 120 can be arginine (R) or leucine (L), (y) the amino acid substitution at residue 142 can be glutamic acid (E) or aspartic acid (D), (z) the amino acid substitution at residue 145 can be leucine (L) or tyrosine (Y), (aa) the amino acid substitution at residue 156 can be glycine (G) or alanine (A), (bb) the amino acid substitution at residue 157 can be glycine (G) or lysine (K), (cc) the amino acid substitution at residue 160 can be glutamic acid (E) or aspartic acid (D), (dd) the amino acid substitution at residue 184 can be asparagine (N) or glutamine (Q), (ee) the amino acid substitution at residue 185 can be glycine (G) or aspartic acid (D), (ff) the amino acid substitution at residue 188 can be glycine (G) or glutamic acid (E), and (gg) the amino acid substitution at residue 192 can be threonine (T) or serine (S).

The functional AID mutant protein can differ from a wild-type AID protein by any of the amino acid substitutions disclosed herein, alone or in any combination. Alternatively, the functional AID mutant protein can have additional amino acid substitutions as compared to a wild-type AID amino acid sequence (e.g., a human AID amino acid sequence of SEQ ID NO: 1 or SEQ ID NO: 2). For example, a functional AID mutant protein can have any one, or combination of, the following amino acid substitutions with respect to SEQ ID NO: 1 or SEQ ID NO: 2: N7K, R8Q, Q14H, R25H, Y48H, N52S, H156R, R158K, L198A, R9K, G100W, A138G, S173T, T195I, F42C, A138G, H156R, L198F M6K, K10Q, A39P, N52A, E118D, K10L, Q14N, N52M, D67A, G100A, V135A, Y145F, R171H, Q175K, R194K, insertion of K after residue 118, and D119E.

The invention also provides nucleic acid molecules encoding functional AID mutants comprising a C-terminal truncation mutation. The generation of a C-terminal trunca-tion mutation is within the ordinary skill in the art, and can be performed, for example, according to the methods described above for generating AID mutants. For example, the C-terminal truncation mutation can be generated by the insertion of a stop codon at or distal to residue 181 of the AID amino acid sequence.

Figure 2:
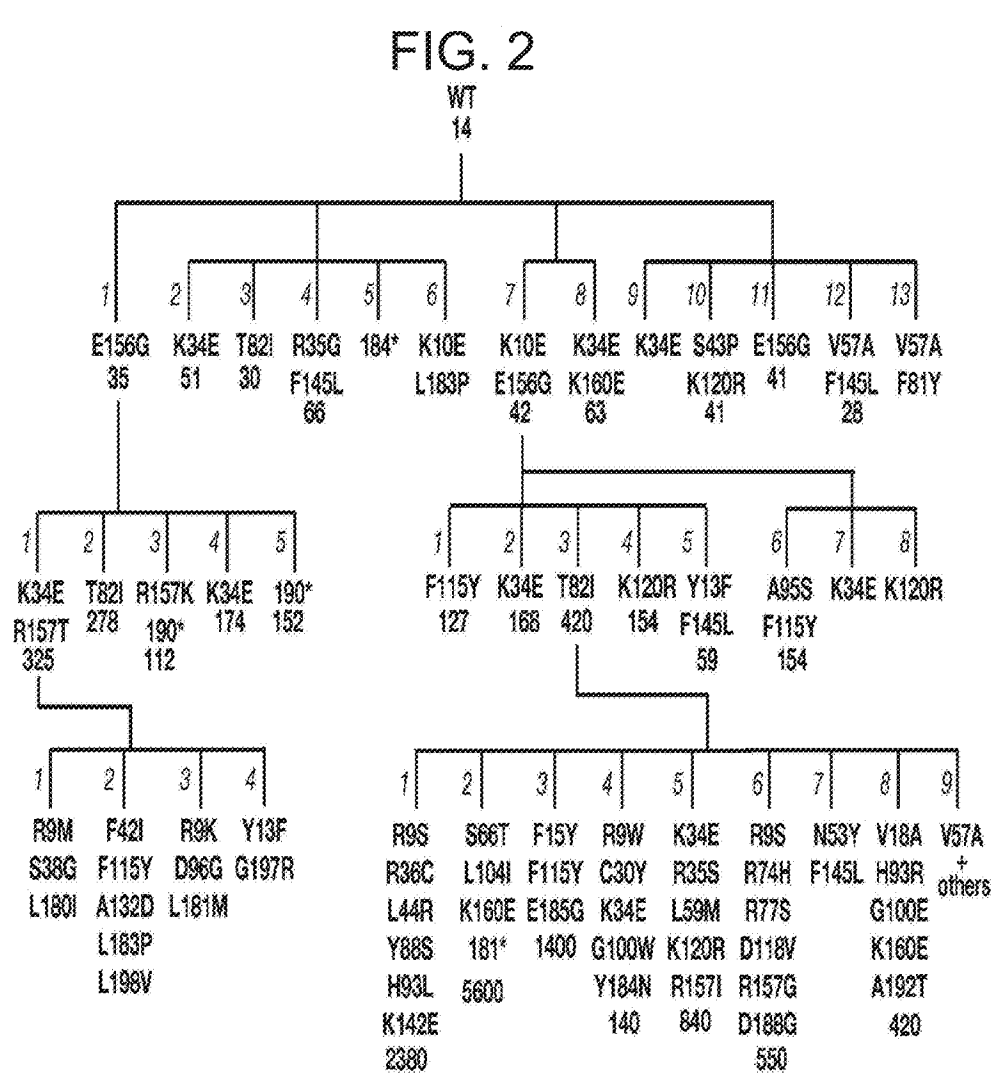

Examples of preferred amino acid substitutions that produce functional AID mutant proteins in the context of the invention are illustrated in FIG. 2.

In the context of the invention, a functional AID mutant also includes a nucleic acid sequence encoding a wild-type AID protein in which a portion of the nucleic acid sequence is deleted and replaced with a nucleic acid sequence from an AID homolog (e.g., Apobec-1, Apobec3C or Apobec3G). In this respect, the human APOBEC3 proteins, like human AID, are able to deaminate cytosine (C) in DNA but, whereas AID prefers to target C residues flanked by a 5'-flanking purine, the APOBEC3s prefer a 5'-pyrimidine flank, with individual APOBEC3s differing with regard to the specific 5'-flanking nucleotide preference. Comparison of human APOBEC3 gene sequences suggests that a stretch of around eight amino acids located about 60 residues from the carboxy terminal end of the protein domain plays an important role in determining this flanking nucleotide preference. In view of the crystal structure of APOBEC2 and the crystal structure of the TadA tRNA-adenosine deaminase in complex with an oligonucleotide substrate, this 60-amino acid sequence in both AID and APOBEC3s likely forms a contact with the DNA substrate. Therefore, in one embodiment of the invention, a functional AID mutant can comprise a nucleic acid sequence encoding a wild-type AID protein in which amino acid residues 115-223 of human AID are removed and replaced with the corresponding sequence from APOBEC3 proteins (e.g., APOBEC3C, APOBec3F, and APOBEC3G).

The invention further provides nucleic acid molecules encoding a fusion protein comprising a functional AID mutant and a second polypeptide fused together in frame. For example, the generation of fusion proteins is within the ordinary skill in the art and can involve the use of restriction enzymes or recombinational cloning techniques.

In one embodiment, the second polypeptide of the fusion protein may comprise a "nuclear localization signal," or "NLS." The terms "nuclear localization signal" and "NLS" refer to a domain, or domains capable of mediating the nuclear import of a protein or polynucleotide, or retention thereof, within the nucleus of a cell. A "strong nuclear import signal" represents a domain or domains capable of mediating greater than 90% subcellular localization in the nucleus when operatively linked to a protein of interest. Representative examples of NLSs include but are not limited to, monopartite nuclear localization signals, bipartite nuclear localization signals and N and C-terminal motifs. N terminal basic domains usually conform to the consensus sequence K-K/R-X-K/R which was first discovered in the SV40 large T antigen and which represents a monopartite NLS. One non-limiting example of an N-terminal basic domain NLS is PKKKRKV (SEQ ID NO: 76). Also known are bipartite nuclear localization signals which contain two clusters of basic amino acids separated by a spacer of about 10 amino acids, as exemplified by the NLS from nucleoplasmin: KR[PAATKKAGQA]KKKK (SEQ ID NO: 77). N and C-terminal motifs include, for example, the acidic M9 domain of hnRNP A1, the sequence KIPIK (SEQ ID NO: 78) in yeast transcription repressor Matα2 and the complex signals of U snRNPs. Most of these NLSs appear to be recognized directly by specific receptors of the importin β family.

In another embodiment, the second polypeptide may be a fusion partner known in the art to facilitate the purification and improve the solubility of the polypeptide to which it is fused, for example, polyhistidine tag, NusA, bacterioferritin (BFR), GrpE, thioredoxin (TRX) or glutathione-S-transferase (GST). The purification of fusion proteins is within the ordinary skill in the art.

In yet another embodiment, the second polypeptide may be a reporter polypeptide such as an autofluorescent protein (e.g., GFP, EGFP). Autofluorescent proteins provide a ready assay for identification of expression of a polynucleotide (and the polypeptide product) of interest. Because the activity of the reporter polypeptide (and by inference its expression level) can be monitored quantitatively using a flow sorter, many independent transfectants can be assayed either sequentially or in bulk population. Cells with the best expression can then be screened for or selected from the population. This is useful when selecting a recombinant cell comprising a functional AID mutant according to the present invention.

In a further embodiment of the invention, the nucleic acid molecules encoding the functional AID mutants of the invention may be codon optimized to reduce or increase the number of somatic hypermutation (SHM) motifs. As used herein, "somatic hypermutation" or "SHM" refers to the mutation of a polynucleotide sequence initiated by, or associated with the action of AID, a functional AID mutant, uracil glycosylase and/or error prone polymerases on that polynucleotide sequence. The term is intended to include mutagenesis that occurs as a consequence of the error prone repair of the initial lesion, including mutagenesis mediated by the mismatch repair machinery and related enzymes.

The term "substrate for SHM" refers to a synthetic or semi-synthetic polynucleotide sequence which is acted upon by AID and/or error prone DNA polymerases to effect a change in the nucleic acid sequence of the synthetic or semi-synthetic polynucleotide sequence.

As used herein, the term "SHM hot spot" or "hot spot" refers to a polynucleotide sequence, or motif, of 3-6 nucleotides that exhibits an increased tendency to undergo somatic hypermutation, as determined via a statistical analysis of SHM mutations in antibody genes. Likewise, as used herein, a "SHM coldspot" or "cold spot" refers to a polynucleotide or motif, of 3-6 nucleotides that exhibits a decreased tendency to undergo somatic hypermutation, as determined via a statistical analysis of SHM mutations in antibody genes. A relative ranking of various motifs for SHM as well as canonical hot spots and cold spots in antibody genes are described in U.S. Patent Application Publication 09/0075378 and International Patent Application Publication WO 08/103475, and the statistical analysis can be extrapolated to analysis of SHM mutations in non-antibody genes (e.g., AID genes) as described therein.

The term "somatic hypermutation motif" or "SHM motif" refers to a polynucleotide sequence that includes, or can be altered to include, one or more hot spots or cold spots, and which encodes a defined set of amino acids. SHM motifs can be of any size, but are conveniently based around polynucleotides of about 2 to about 20 nucleotides in size, or from about 3 to about 9 nucleotides in size. SHM motifs can include any combination of hot spots and cold spots, or may lack both hot spots and cold spots.

The terms "preferred hot spot SHM codon," "preferred hot spot SHM motif," "preferred SHM hot spot codon" and "preferred SHM hot spot motif," all refer to a codon including, but not limited to codons AAC, TAC, TAT, AGT, or AGC. Such sequences may be potentially embedded within the context of a larger SHM motif, recruits SHM mediated mutagenesis and generates targeted amino acid diversity at that codon.

As used herein, a nucleic acid sequence has been "optimized for SHM" if the nucleic acid sequence, or a portion thereof has been altered to increase or decrease the frequency and/or location of hot spots and/or cold spots within the nucleic acid sequence. A nucleic acid sequence that has been made "susceptible to SHM" if the nucleic acid sequence, or a portion thereof, has been altered to increase the frequency and/or location of hot spots within the nucleic acid sequence or to decrease the frequency (density) and/or location of cold spots within the nucleic acid sequence. Conversely, a nucleic acid sequence has been made "resistant to SHM" if the nucleic acid sequence, or a portion thereof, has been altered to decrease the frequency (density) and/or location of hot spots within the open reading frame of the nucleic acid sequence. In general, a sequence can be prepared that has a greater or lesser propensity to undergo SHM mediated mutagenesis by altering the codon usage, and/or the amino acids encoded by nucleic acid sequence.

Optimization of a nucleic acid sequence refers to modifying about 1%, about 2%, about 3%, about 4%, about 5%, about 10%, about 20%, about 25%, about 50%, about 75%, about 90%, about 95%, about 96%, about 97%, about 98%, about 99%, about 100%, or any range therein, of the nucleotides in the nucleic acid sequence. Optimization of a polynucleotide sequence also refers to modifying about 1, about 2, about 3, about 4, about 5, about 10, about 20, about 25, about 50, about 75, about 90, about 95, about 96, about 97, about 98, about 99, about 100, about 200, about 300, about 400, about 500, about 750, about 1000, about 1500, about 2000, about 2500, about 3000 or more, or any range therein, of the nucleotides in the nucleic acid sequence such that some or all of the nucleotides are optimized for SHM-mediated mutagenesis. Reduction in the frequency (density) of hot spots and/or cold spots refers to reducing about 1%, about 2%, about 3%, about 4%, about 5%, about 10%, about 20%, about 25%, about 50%, about 75%, about 90%, about 95%, about 96%, about 97%, about 98%, about 99%, about 100%, or any range therein, of the hot spots or cold spots in a nucleic acid sequence. Increasing the frequency (density) of hot spots and/or cold spots refers to increasing about 1%, about 2%, about 3%, about 4%, about 5%, about 10%, about 20%, about 25%, about 50%, about 75%, about 90%, about 95%, about 96%, about 97%, about 98%, about 99%, about 100%, or any range therein, of the hot spots or cold spots in a nucleic acid sequence.

The position or reading frame of a hot spot or cold spot is also a factor governing whether SHM mediated mutagenesis that can result in a mutation that is silent with regards to the resulting amino acid sequence, or causes conservative, semi-conservative or non conservative changes at the amino acid level. The design parameters can be manipulated to further enhance the relative susceptibility or resistance of a nucleotide sequence to SHM. Thus both the degree of SHM recruitment and the reading frame of the motif are considered in the design of SHM susceptible and SHM resistant nucleic acid sequences.

The invention also provides a vector comprising a nucleic acid molecule encoding a functional AID mutant. A "vector" or "cloning vector" is a replicon, such as plasmid, phage or cosmid, into which another polynucleotide segment may be introduced so as to bring about the replication of the inserted segment. Vectors typically exist as circular, double stranded DNA, and range in size form a few kilobases (kb) to hundreds of kb. Preferred cloning vectors have been modified from naturally occurring plasmids to facilitate the cloning and recombinant manipulation of polynucleotide sequences. Many such vectors are well known in the art; see for example, Sambrook et al, "Molecular Cloning: A Laboratory Manual," second edition, Cold Spring Harbor Laboratory, (1989), and Maniatis et al., Cell Biology: A Comprehensive Treatise, Vol. 3, Gene Sequence Expression, Academic Press, NY, pp. 563-608 (1980).

The term "expression vector" as used herein, refers to vector used for expressing certain polynucleotides within a host cell or in vitro expression system. The term includes plasmids, episomes, cosmids, retroviruses or phages. The expression vector can be used to express a DNA sequence encoding a desired protein and in one aspect includes a transcriptional unit comprising an assembly of expression control sequences. The choice of promoter and other regulatory elements generally varies according to the intended host cell, or in vitro expression system.

As used herein an "in vitro expression system" refers to cell free systems that enable the transcription, or coupled transcription and translation of DNA templates. Such systems include, for example, the rabbit reticulocyte system, as well as novel cell-free synthesis systems, (*J. Biotechnol.*, 110: 257-63 (2004); *Biotechnol. Annu. Rev.*, 10:1-30 (2004)).

"Expression control sequences" are DNA regulatory sequences, such as promoters, enhancers, polyadenylation signals, transcription terminators, internal ribosome entry sites (IRES), and the like, that provide for the expression of a coding sequence in a host cell. Exemplary expression control sequences are known in the art and described in Goeddel; Gene Expression Technology: Methods in Enzymology 185, Academic Press, San Diego, Calif. (1990).

A "promoter" is a DNA sequence capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease 51), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and -35 consensus sequences.

A large number of promoters, including constitutive, inducible, and repressible promoters, from a variety of different sources are well known in the art. Representative sources include for example, viral, mammalian, insect, plant, yeast, and bacterial cell types), and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include the Tet system, (U.S. Pat. Nos. 5,464,758 and 5,814,618), the Ecdysone inducible system (No et al., *Proc. Natl. Acad. Sci.*, 93: 3346-3351 (1996); the T-REx™ system (Invitrogen, Carlsbad, Calif.), LacSwitch® (Stratagene, San Diego, Calif.) and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715). See generally, Kramer & Fussenegger, *Methods Mol. Biol.*, 308: 123-144 (2005)) or any promoter known in the art suitable for expression in the desired cells.

If an inducible system is used, such as the Tet-controlled system, doxycycline can be added to the medium to induce expression of the nucleic acid encoding a functional AID mutant for a period of time (e.g., 1 hour (hr), 2 hrs, 4 hrs, 6 hrs, 8 hrs, 10 hrs, 15 hrs, 20 hrs, 24 hrs or any other time) prior to analysis by an appropriate assay. The cells can be allowed to grow for a certain time to provide for on-going diversification, for example, for 1-3 cell generations, or in certain cases 3-6 generations, or in some cases 6 to 10 generations, or longer.

As used herein, a "minimal promoter" refers to a partial promoter sequence which defines the transcription start site but which by itself is not capable, if at all, of initiating transcription efficiently. The activity of such minimal promoters depends on the binding of activators such as a tetracycline-controlled transactivator to operably linked binding sites.

The terms "IRES" or "internal ribosome entry site" refer to a polynucleotide element that acts to enhance the translation of a coding sequence encoded with a. polycistronic messenger RNA. IRES elements, mediate the initiation of translation by directly recruiting and binding ribosomes to a messenger RNA (mRNA) molecule, bypassing the 7-methyl guanosine-cap involved in typical ribosome scanning. The presence of an IRES sequence can increase the level of cap-independent translation of a desired protein. Early publications descriptively refer to IRES sequences as "translation enhancers." For example, cardioviral RNA "translation enhancers" are described in U.S. Pat. Nos. 4,937,190 and 5,770,428.

The term "enhancer" as used herein, refers to a DNA sequence that increases transcription of, for example, a gene or coding sequence to which it is operably linked. Enhancers can be located many kilobases away from the coding sequence and can mediate the binding of regulatory factors, patterns of DNA methylation or changes in DNA structure. A large number of enhancers, from a variety of different sources are well known in the art and available as or within cloned polynucleotides (from, e.g., depositories such as the ATCC as well as other commercial or individual sources). A number of polynucleotides comprising promoters (such as the commonly-used CMV promoter) also comprise enhancer sequences. Operably linked enhancers can be located upstream, within, or downstream of coding sequences. The term "Ig enhancers" refers to enhancer elements derived from enhancer regions mapped within the Ig locus (such enhancers include for example, the heavy chain (mu) 5' enhancers, light chain (kappa) 5' enhancers, kappa and mu intronic enhancers, and 3' enhancers, (see generally Paul WE (ed) Fundamental Immunology, 3rd Edition, Raven Press, New York (1993) pages 353-363; U.S. Pat. No. 5,885,827).

"Terminator sequences" are those that result in termination of transcription. Termination sequences are known in the art and include, but are not limited to, poly A (e.g., Bgh Poly A and SV40 Poly A) terminators. A transcriptional termination signal will typically include a region of 3' untranslated region (or "3' ut"), an optional intron (also referred to as intervening sequence or "IVS") and one or more poly adenylation signals ("p(A)" or "pA." Terminator sequences may also be referred to as "IVS-pA," "IVS+p (A)," "3' ut+p(A)" or "3' ut/p(A)." Natural or synthetic terminators can be used as a terminator region.

The terms "polyadenylation," "polyadenylation sequence" and "polyadenylation signal", "Poly A," "p(A)" or "pA" refer to a nucleic acid sequence present in a RNA transcript that allows for the transcript, when in the presence of the polyadenyl transferase enzyme, to be polyadenylated. Many polyadenylation signals are known in the art. Non-limiting examples include the human variant growth hormone polyadenylation signal, the SV40 late polyadenylation signal and the bovine growth hormone polyadenylation signal.

An "episomal expression vector" is able to replicate in a host cell, and persists as an extrachromosomal segment of DNA within the host cell in the presence of appropriate selective pressure (see, e.g., Conese et al., *Gene Therapy* 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7 from Invitrogen, pcDNA3.1 from Invitrogen, and pBK-CMV from Stratagene represent non-limiting examples of an episomal vector that uses T-antigen and the SV40 origin of replication in lieu of EBNA1 and oriP.

An "integrating expression vector" may randomly integrate into the host cell's DNA, or may include a recombination site to enable the specific recombination between the expression vector and the host cells chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (e.g., pcDNA™5/FRT), or the cre-lox system, such as can be found in the pExchange-6 Core Vectors from Stratagene. Examples of vectors that integrate into host cell chromosomes in a random fashion include, for example, pcDNA3.1 (when introduced in the absence of T-antigen) from Invitrogen, pCI or pFN10A (ACT) Flexi® from Promega.

Representative commercially available viral expression vectors include, but are not limited to, the adenovirus-based Per.C6 system available from Crucell, Inc., the lentiviral-based pLP1 from Invitrogen, and the Retroviral Vectors pFB-ERV plus pCFB-EGSH from Stratagene.

Alternatively, the expression vector may be used to introduce and integrate a strong promoter or enhancer sequences into a locus in the cell so as to modulate the expression of an endogenous gene of interest (Capecchi M R. *Nat Rev Genet.*, 6(6): 507-12 (2005); Schindehutte et al., *Stem Cells*, 23(1): 10-5 (2005)). This approach can also be used to insert an inducible promoter, such as the Tet-On promoter (U.S. Pat. Nos. 5,464,758 and 5,814,618), in to the genomic DNA of the cell so as to provide inducible expression of an endogenous gene of interest. The activating construct can also include targeting sequence(s) to enable homologous or non-homologous recombination of the activating sequence into a desired locus specific for the gene of interest (see, e.g., Garcia-Otin and Guillou, *Front. Biosci.*, 11: 1108-36 (2006)). Alternatively, an inducible recombinase system, such as the Cre-ER system, can be used to activate a transgene in the presence of 4-hydroxytamoxifen. (Indra et al., *Nuc. Acid. Res.*, 27(22): 4324-4327 (1999); *Nuc. Acid. Res.*, 28(23): e99 (2000); U.S. Pat. No. 7,112,715).

The vector of the present invention may comprise a "selectable marker gene." The term "selectable marker gene" as used herein, refers to polynucleotides that allow cells carrying the polynucleotide to be specifically selected for or against, in the presence of a corresponding selective agent. Selectable markers can be positive, negative or bifunctional. Positive selectable markers allow selection for cells carrying the marker, whereas negative selectable markers allow cells carrying the marker to be selectively eliminated. The selectable marker polynucleotide can either be directly linked to the polynucleotides to be expressed, or introduced into the same cell by co-transfection. A variety of such marker polynucleotides have been described, including, for example, bifunctional (i.e., positive/negative) markers (see, e.g., International Patent Application Publications WO 92/08796 and WO 94/28143), drug-resistance genes (e.g., ampicillin), and proteins that confer resistance to cytostatic or cytocidal drugs (e.g., the DHFR protein) (see, e.g., Wigler et al., *Proc. Natl. Acad. Sci. USA*, 77: 3567 (1980), O'Hare et al., *Proc. Natl. Acad. Sci. USA*, 78: 1527 (1981), Mulligan & Berg, *Proc. Natl. Acad. Sci. USA*, 78: 2072 (1981), Colberre-Garapin et al., *J. Mol. Biol.*, 150:1 (1981), Santerre et al., *Gene*, 30: 147 (1984), Kent et al., *Science*, 237: 901-903 (1987), Wigler et al., *Cell*, 11: 223 (1977), Szybalska & Szybalski, *Proc. Natl. Acad. Sci. USA*, 48:2026 (1962), Lowy et al., *Cell*, 22:817 (1980), and U.S. Pat. Nos. 5,122,464 and 5,770,359).

The vector may comprise a "reporter gene." A "reporter gene" refers to a polynucleotide that confers the ability to be specifically detected, (or detected and selected) typically when expressed with a cell of interest. Numerous reporter gene systems are known in the art and include, for example alkaline phosphatase (Berger, J., et al., *Gene*, 66: 1-10 (1988); Kain, S R., *Methods Mol. Biol.*, 63: 49-60 (1997)), beta-galactosidase (U.S. Pat. No. 5,070,012), chloramphenicol acetyltransferase (Gorman et al., *Mol. Cell. Biol.*, 2: 1044-51 (1982)), beta glucuronidase, peroxidase, beta lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R Y, *Annu. Rev. Biochem.*, 67: 509-544 (1998)). The term "reporter gene," also includes any peptide which can be specifically detected based on the use of one or more, antibodies, epitopes, binding partners, substrates, modifying enzymes, receptors, or ligands that are capable of, or desired to (or desired not to), interact with the peptide of interest to create a detectable signal. Reporter genes also include genes that can modulate cellular phenotype. The reporter protein, when served for such detection purpose, does not have to be fused with the mutant AID protein. It may be encoded by the same polynucleotide (e.g., a vector) which also encodes the mutant AID protein and be co-introduced and co-expressed in a target cell.

Expression vectors may also include anti-sense, ribozymes or siRNA polynucleotides to reduce the expression of target sequences (see, e.g., Sioud M, & Iversen, *Curr. Drug Targets*, 6: 647-53 (2005); Sandy et al., *Biotechniques*, 39:215-24 (2005)).

The invention also provides a cell comprising a nucleic acid molecule encoding a functional AID mutant or a vector comprising the nucleic acid molecule encoding a functional AID mutant. The terms "cells," "cell cultures," "cell line," "recombinant host cells," "recipient cells," and "host cells" are often used interchangeably and include primary subject cells and any progeny thereof, without regard to the number of transfers. It should be understood that not all progeny are exactly identical to the parental cell (due to deliberate or inadvertent mutations or differences in environment). However, such altered progeny are included in these terms, so long as the progeny retain the same functionality as that of the originally transformed cell. For example, though not limited to, such a characteristic might be the ability to produce a particular recombinant protein. A "mutator positive cell line" is a cell line containing cellular factors that are sufficient to work in combination with other vector elements to effect hypermutation. The cell line can be any of those known in the art or described herein. A "clone" is a population of cells derived from a single cell or common ancestor by mitosis.

Cell-based expression and hypermutation systems include any suitable prokaryotic or eukaryotic expression systems. Preferred systems are those that can be easily and reliably grown, have reasonably fast growth rates, have well characterized expression systems and can be transformed or transfected easily and efficiently.

Useful microbial cells include, but are not limited to, cells from the genera Bacillus, Escherichia (such as E. coli), Pseudomonas, Streptomyces, Salmonella, Erwinia, Bacillus subtilis, Bacillus brevis. Particularly useful prokaryotic cells include the various strains of Escherichia coli (e.g., K12, HB101, (ATCC NO. 33694) DH5α, DH10, MC1061 (ATCC NO. 53338), and CC102).

Many strains of yeast cells known to those skilled in the art are also available as host cells for the expression of polypeptides including those from the genera Hansenula, Kluyveromyces, Pichia, Rhino-sporidium, Saccharomyces, and Schizosaccharomyces, and other fungi. Preferred yeast cells include, for example, Saccharomyces cerivisae and Pichia pastoris.

Additionally, where desired, insect cell systems can be utilized in the methods of the present invention. Such systems are described, for example, by Kitts et al., Biotechniques, 14: 810-817 (1993); Lucklow, Curr. Opin. Biotechnol., 4: 564-572 (1993); and Lucklow et al., J. Virol., 67: 4566-4579 (1993). Preferred insect cells include Sf-9 and HI5 (Invitrogen, Carlsbad, Calif.).

The cell comprising the nucleic acid encoding a functional AID mutant preferably is a mammalian cell. A number of suitable mammalian host cells are also known in the art and many are available from the American Type Culture Collection (ATCC, Manassas, Va.). Examples of suitable mammalian cells include, but are not limited to, Chinese hamster ovary cells (CHO) (ATCC No. CCL61) CHO DHFR-cells (Urlaub et al., Proc. Natl. Acad. Sci. USA, 97: 4216-4220 (1980)), human embryonic kidney (HEK) 293 or 293T cells (ATCC No. CRL1573), and 3T3 cells (ATCC No. CCL92). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells can be genotypically deficient in the selection gene, or can contain a dominantly acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines, which are available from the ATCC.

Also within the scope of the invention are lymphoid, or lymphoid derived cell lines, such as a cell line of pre-B lymphocyte origin. Specific examples include without limitation RAMOS(CRL-1596), Daudi (CCL-213), EB-3 (CCL-85), DT40 (CRL-2111), 18-81 (Jack et al., Proc. Natl. Acad. Sci. USA, 85: 1581-1585 (1988)), Raji cells (CCL-86), and derivatives thereof.

A functional AID mutant of the present invention may be introduced into a cell by "transfection," "transformation," or "transduction." "Transfection," "transformation," or "transduction" as used herein, refers to the introduction of one or more exogenous polynucleotides into a host cell by using one or physical or chemical methods. Many transfection techniques are known to those of ordinary skill in the art including but not limited to calcium phosphate DNA co-precipitation (see Methods in Molecular Biology, Vol. 7, Gene Transfer and Expression Protocols, Ed. E. J. Murray, Humana Press (1991)); DEAE-dextran; electroporation; cationic liposome-mediated transfection; tungsten particle-facilitated microparticle bombardment (Johnston, S. A., Nature, 346: 776-777 (1990)); and strontium phosphate DNA co-precipitation (Brash D. E. et al. Molec. Cell. Biol., 7: 2031-2034 (1987). Phage or retroviral vectors can be introduced into host cells, after growth of infectious particles in packaging cells that are commercially available.

The invention also provides a method for preparing a gene product having a desired property, which method comprises expressing a nucleic acid encoding the gene product in a population of cells, wherein the population of cells expresses, or can be induced to express, a functional AID mutant protein of the present invention, whereupon expression of the functional AID mutant protein induces a mutation in the nucleic acid encoding the gene product. Descriptions of the functional AID mutant, cells, and methods of transfecting and expressing nucleic acid molecules into cells set forth above in connection with other embodiments of the invention also are applicable to those same aspects of the aforesaid method.

Desirably, the functional AID mutant protein induces a mutation in the nucleic acid encoding the gene product by way of somatic hypermutation (SHM). The use of AID in SHM systems is described in detail in U.S. patent application Ser. No. 09/075,378 and International Patent Application Publications WO/08103474 and WO 08/103475. As used herein, the term "gene product of interest" or "protein of interest" relates to proteins, or portions thereof, for which it is desired that the nucleic acid encoding the gene product is optimized for SHM by a functional AID mutant in order to rapidly create, select, and identify improved variants of that gene product. Such optimized nucleic acid sequences can be made more susceptible to SHM as a result of codon usage (as described herein), thereby inducing amino acid changes when the polynucleotide is subjected to a functional AID mutant, and screened for improved function. Conversely, such optimized nucleic acid sequences can be made more resistant to SHM (as described herein), thereby decreasing amino acid changes when the polynucleotide is subjected to a functional AID mutant as a result of codon usage, and screened for improved function.

Any protein for which the amino acid, or corresponding nucleotide sequence is known, or available (e.g., can be cloned into a vector as described herein), and a phenotype or function can be improved, is a candidate for use in the inventive method. Examples of suitable proteins include, for example, surface proteins, intracellular proteins, membrane proteins, and secreted proteins from any unmodified or synthetic source. The gene product preferably is an antibody heavy chain or portion thereof, an antibody light chain or portion thereof, an enzyme, a receptor, a structural protein, a co-factor, a polypeptide, a peptide, an intrabody, a selectable marker, a toxin, growth factor, peptide hormone, or any other protein which can be optimized.

The gene product can be any suitable enzyme, including enzymes associated with microbiological fermentation, metabolic pathway engineering, protein manufacture, bioremediation, and plant growth and development (see, e.g., Olsen et al., *Methods Mol. Biol.*, 230: 329-349 (2003); Turner, *Trends Biotechnol.*, 21(11): 474-478 (2003); Zhao et al., *Curr. Opin. Biotechnol.*, 13(2): 104-110 (2002); and Mastrobattista et al., *Chem. Biol.*, 12(12): 1291-300 (2005)).

Suitable receptors for use in the inventive method include, but are not limited to, cell-bound receptors such as antibodies (B cell receptors), T cell receptors, Fc receptors, G-coupled protein receptors, cytokine receptors, carbohydrate receptors, and Avimer™ based receptors. Such receptors can be altered through SHM to improve one or more of the following traits; affinity, avidity, selectivity, thermostability, proteolytic stability, solubility, dimerization, folding, immunotoxicity, coupling to signal transduction cascades and expression.

Suitable gene products for use in the inventive method also include molecules capable of modulating the pharmacokinetics and/or pharmacodynamics of other biologically active proteins, e.g., lipids and polymers such as polyamines, polyamides, polyethylene glycol and other polyethers. Other examples of suitable gene products for use in the inventive method include polypeptides such as VEGF, VEGF receptor, Diptheria toxin subunit A, *B. pertussis* toxin, CC chemokines (e.g., CCL1-CCL28), CXC chemokines (e.g., CXCL1-CXCL16), C chemokines (e.g., XCL1 and XCL2) and CX3C chemokines (e.g., CX3CL1), IFN-gamma, IFN-alpha, IFN-beta, TNF-alpha, TNF-beta, IL-1, IL-2, IL-3, IL-4, IL-5, IL-6, IL-7, IL-10, IL-12, IL-13, IL-15, TGF-beta, TGF-alpha, GM-CSF, G-CSF, M-CSF, TPO, EPO, human growth factor, fibroblast growth factor, nuclear co-factors, Jak and Stat family members, G-protein signaling molecules such as chemokine receptors, JNK, Fos-Jun, NF-κB, I-κB, CD40, CD4, CD8, B7, CD28, and CTLA-4. Methods for selecting a gene product (e.g., protein) of interest as a suitable candidate for mutation and optimization via SHM, as well as related screening assays, are further disclosed in U.S. Patent Application Publication 09/0075378 and International Patent Application Publications WO/08103474 and WO 08/103475.

In a preferred embodiment of the invention, the nucleic acid sequence that is subject to mutation by the functional AID mutant protein encodes an antibody, or a portion thereof. Nucleic acid sequences encoding all naturally occurring germline, affinity matured, synthetic, or semi-synthetic antibodies, as well as fragments thereof, may be used in the present invention. In general, such antibody-encoding sequences can be altered through SHM to improve one or more of the following functional traits: affinity, avidity, selectivity, thermostability, proteolytic stability, solubility, folding, immunotoxicity and expression. Depending upon the antibody format, libraries can be generated which comprise separate heavy chain and light chain libraries that can be co-expressed in a host cell. In certain embodiments, full length antibodies can be secreted (or released), and/or surface displayed at the plasma membrane of the host cell. In still other embodiments, heavy and light chain libraries can be inserted in to the same expression vector, or different expression vectors to enable simultaneous co-evolution of both antibody chains.

Therefore, the inventive method provides the ability to bypass the need for immunization in vivo to select antibodies that bind to key surface epitopes that are aligned with producing the most robust biological effects on target protein function. Additionally, mammalian antibodies intrinsically process optimal codon usage patterns for targeted SHM, greatly simplifying template design strategies. For certain antigens, in vivo immunization leads to epitope selection that does not impact target function, thereby hindering the selection of potent and efficacious antibody candidates. In still other embodiments, the inventive method can provide for the rapid evolution of site-directed antibodies that have potent activity by nature of the role of that epitope in determining target protein function. This provides the ability to scan target proteins for optimal epitope position and produce best in class antibodies drugs for use in the clinic.

The inventive method can be used to increase the hotspot density in specific sub domains of antibodies or fragments thereof (e.g., F(ab')2, Fab', Fab, Fv, scFv, dsFv, dAb or a single chain binding polypeptide), which can result in an improvement in a characteristic (e.g., increased binding affinity, increased binding avidity, and/or decreased non-specific binding). The inventive method also can be used to generate synthetic antibodies with increased hotspots in the constant domain (e.g., Fc), which can result in increased binding affinity for an Fc receptor (FcR), thereby modulating signal cascades. Heavy chains and light chains, or portions thereof, can be simultaneously modified using the methods described herein.

Intrabodies can be modified using the inventive method to improve or enhance folding of the heavy and/or light chain in the reducing environment of the cytoplasm. Alternatively, or in addition, a sFv intrabody can be modified to stabilize frameworks that could fold properly in the absence of intradomain disulfide bonds. Intrabodies can also be modified to increase, for example, one or more of the following characteristics: binding affinity, binding avidity, epitope accessibility, competition with endogenous proteins for the target epitope, half-life, target sequestration, post-translational modification of the target protein, etc. Because intrabodies act within the cell, their activity is more analogous to assay methodologies for enzyme activity assays.

Methods for designing and creating antibody libraries, as well as methods for identifying optimal epitopes that provide for the selection of antibodies with superior selectivity, cross species reactivity, and blocking activity are known in the art (see, e.g., U.S. Patent Application Publication 09/0075378 and International Patent Application Publications WO 08/103474 and WO 08/103475). Specific screens to detect and select surface exposed or secreted antibodies with improved traits, are well known in the art. Such screens can involve several rounds of selection based on the simultaneous selection of multiple parameters, for example, affinity, avidity, selectivity and thermostability in order to evolve the overall best antibody.

It will be appreciated that there are a variety of other component nucleotide sequences, such as coding sequences and genetic elements, that one of ordinary skill in the art would prefer the functional mutant AID protein not mutate to maintain overall system integrity. These component nucleotide sequences are described herein and include, without limitation, (i) selectable markers, (ii) reporter genes, (iii) genetic regulatory signals, (iv) enzymes or accessory factors used for high level enhanced SHM, or its regulation, or measurement (e.g., AID or a functional AID mutant, pol eta, transcription factors, and MSH2, (v) signal transduction components (e.g., kinases, receptors, transcription factors), and (vi) domains or sub domains of proteins (e.g., nuclear localization signals, transmembrane domains, catalytic domains, protein-protein interaction domains, and other protein family conserved motifs, domains and sub-domains).

Depending on the nature of the gene product of interest, and amount of information available on the gene product of interest, one of ordinary skill in the art can follow any combination of the following strategies prior to, or in conjunction with, practicing the inventive method to prepare a gene product of interest with a desired property.

1. No SHM optimization: Although it can be desirable to enhance the number of hot spots within the nucleic acid sequence encoding a gene product of interest, it should be noted that any unmodified nucleic acid sequence is expected to undergo a certain amount of SHM, and can be used in the inventive method without optimization, or any specific knowledge of the actual sequence. Moreover, certain proteins (e.g., antibodies) naturally comprise nucleic acid sequences which have evolved suitable codon usage, and do not require codon modification. Alternatively, it can be desirable to enhance the number of cold spots within the nucleic acid sequence encoding a gene product of interest (e.g., framework regions of antibodies or fragments thereof).

2. Global SHM Hot spot optimization: In some aspects, the number of hotspots in a nucleic acid sequence encoding a gene product can be increased, as described in detail in U.S. Patent Application Publication 09/0075378 and International Patent Application Publication WO 08/103475. This approach can be applied to the entire coding region of the nucleic acid sequence, thereby rendering the entire nucleic acid sequence more susceptible to SHM. This approach can be preferred if relatively little is known about structure activity relationships of the gene product, or between related isotypes.

3. Selective SHM hot spot modification: Alternatively, a nucleic acid sequence encoding the protein of interest can be selectively and/or systematically modified through the targeted replacement of regions of interest with synthetic variable regions as described in U.S. Patent Application Publication 09/0075378 and International Patent Application Publication WO 08/103475, which provide for a high density of hot spots and seed maximal diversity through SHM at specific loci.

One of ordinary skill in the art would understand, based on the foregoing, that any or all of the above approaches can be undertaken in conjunction with the inventive method. Methods for global SHM hot spot optimization and selective SHM hot spot modification, however, are likely to lead to faster and more efficient optimization of protein function.

Following the design of an SHM-optimized nucleic acid sequence encoding the gene product of interest, it can be synthesized using standard methodology and sequenced to confirm correct synthesis. Once the sequence of the nucleic acid sequence has been confirmed, the nucleic acid sequence can be inserted into a vector as described herein, and the vector can then be introduced into a host cell as described herein. Enhancers (e.g., Ig enhancers) can be inserted into a vector to increase expression, and/or targeting of SHM initiated by the functional AID mutant protein to the nucleic acid sequence encoding a gene product of interest.

In accordance with the inventive method, any of the vectors described herein can be co-transfected into a host cell with a separate vector containing the nucleic acid sequence encoding a functional AID mutant as described herein. In one aspect, the vectors described herein can be transfected into a host cell that contains (and expresses) an endogenous AID protein. In another aspect, the vectors described herein can be co-transfected into a host cell that contains an endogenous AID protein with a separate vector containing the nucleic acid sequence of a functional AID mutant such that the functional AID mutant is over-expressed in the cell. In yet another aspect, the vectors described herein can be modified to include a nucleic acid sequence encoding a functional AID mutant for transfection into a host cell that does, or does not, contain an endogenous AID protein. In a preferred embodiment the functional AID mutant is a synthetic AID that is encoded by a nucleic acid sequence that is SHM resistant.

Following introduction of one or more nucleic acids into an expression vector, the vector can be amplified, purified, introduced into a host cell using standard transfection techniques and characterized using standard molecular biological techniques. Purified plasmid DNA can be introduced into a host cell using standard transfection/transformation techniques and the resulting transformants/transfectants grown in appropriate medium containing antibiotics, selectable agents and/or activation/transactivator signals (e.g. inducible agents such as doxycycline) to induce expression of the nucleic acid sequence encoding the gene product of interest.

The inventive method can further comprise introducing into the cell or population of cells one or more of the following (i) at least one nucleic acid sequence that that has been altered in whole or part, from a corresponding wild-type nucleic acid sequence to positively influence the rate of SHM experienced by that nucleic acid sequence, or a nucleic acid sequence that has a naturally high percentage of hot spots prior to any modification, and/or (ii) a nucleic acid sequence that has been altered, in whole or part, to negatively influence the rate of SHM.

In one aspect, the inventive method can further comprise introducing into the cell or population of cells one or more nucleic acid sequences that have been altered from a corresponding wild-type nucleic acid sequence to negatively influence the rate of SHM. The nucleic acid sequence can encode, for example, one or more of factors for SHM (e.g. AID, Pol eta, UDG), one or more selectable marker genes, or one or more reporter genes.

In another aspect, the inventive method can further comprise introducing into the cell or population of cells one or more nucleic acid sequences that have been altered, in whole or part, from a corresponding wild-type nucleic acid sequence to positively influence the rate of SHM. The nucleic acid sequence can encode, for example, an enzyme, receptor, transcription factor, structural protein, toxin, co-factor, or specific binding protein of interest.

In yet another aspect, the inventive method can further comprise introducing into the cell or population of cells a nucleic acid sequence having an intrinsically high rate of SHM such as, for example, a nucleic acid sequence encoding an immunoglobulin heavy chain or an immunoglobulin light chain, or a hypervariable region of an antibody gene.

The cell or population of cells of the inventive method can further comprise one or more of the following additional elements (i) an inducible system to regulate the expression of AID, an AID homolog, or a functional AID mutant of the present invention, (ii) one or more Ig enhancers, (iii) one or more E-boxes, (iv) one or more auxiliary factors for SHM, (v) one or more factors for stable episomal expression, such as EBNA1, EBP2 or ori-P, (vi) one or more selectable marker genes, (vii) one or more secondary vectors containing the gene for AID, an AID homolog, or a functional AID mutant of the present invention, or (viii) a combination thereof.

In another aspect of the invention, the method comprises expressing two nucleic acid sequences, each encoding a gene product of interest, in which both nucleic acid sequences are located in proximity to a promoter, and expressed and co-evolved in the same cell simultaneously. The promoter can be a bi-directional promoter such as a bi-directional CMV promoter. In another embodiment, the two nucleic acid sequences of interest are placed in front of two uni-directional promoters. The two promoters can be the same promoter or different promoters. The two nucleic acid sequences of interest can be in the same vector or on different vectors.

The cell or population of cells either constitutively expresses, or can be induced to express a functional mutant AID protein as described herein. Expression of the functional mutant AID protein induces a mutation in the nucleic acid sequence encoding the gene product. The cell or population of cells also can express other factors that enhance AID-mediated mutation of the nucleic acid sequence. As a result of the inventive method, on-going sequence diversification of the nucleic acid sequence encoding the gene product of interest is achieved. After an appropriate period of time, (e.g., 2-10 cell divisions) the resulting host cells, which include variants of the gene product of interest, can be screened and improved mutants identified and separated from the cell population. Cells can be iteratively grown, assayed, and selected as described herein to selectively enrich those cells that express a nucleic acid sequence encoding a gene product of interest exhibiting a desired property. Suitable assay and enrichment strategies (e.g., fluorescent activated cell sorting (FACS), affinity separation, enzyme activity, toxicity, receptor binding, growth stimulation, etc.) are known in the art and described in, for example, U.S. Patent Application Publication 09/0075378 and International Patent Application Publications WO 08/103475 and WO 08/103474.

In one embodiment of the invention, the nucleic acid sequence encoding the gene product of interest can be engineered such that the gene product of interest is displayed at the cell-surface. In this respect, a cell-surface displayed protein can be created through the creation of a chimeric molecule of a protein of interest coupled in frame to a suitable transmembrane domain. In the case of mammalian cell expression, for example, a MHC type 1 transmembrane domain such as that from H2kk (including peri-transmembrane domain, transmembrane domain, and cytoplasmic domain; NCBI Gene Accession number AK153419) can be used. Likewise the surface expression of proteins in prokaryotic cells (such as *E. coli* and *Staphylococcus*) insect cells, and yeast is well established in the art (see, e.g., Winter et al., *Annu. Rev. Immunol.*, 12: 433-55 (1994); Plückthun A. *Bio/Technology*, 9: 545-551 (1991); Gunneriusson et al., *J. Bacteriol.*, 78: 1341-1346 (1996); Ghiasi et al., *Virology*, 185: 187-194 (1991); Boder and Wittrup, *Nat. Biotechnol.*, 15: 553-557 (1997); and Mazor et al., *Nat. Biotechnol.*, 25(5): 563-565 (2007)).

Surface displayed antibodies or proteins can be created through the secretion and then binding (or association) of the secreted protein on the cell surface. Conjugation of the antibody or protein to the cell membrane can occur either during protein synthesis or after the protein has been secreted from the cell. Conjugation can occur via covalent linkage, by binding interactions (e.g., mediated by specific binding members) or a combination of covalent and non-covalent linkage. Proteins also can be coupled to a cell through the creation of an antibody or binding protein fusion protein comprising a first specific binding member that specifically binds to a target of interest fused to a second binding member specific for display on a cell surface (e.g., in the case of exploiting the binding of protein A and a Fc domain: protein A is expressed on and attached to a cell surface and binds to, and localizes, a secreted antibody (or a protein of interest expressed as an Fc fusion protein)).

It may be desirable in some instances to convert a surface displayed protein into a protein that is released or shed from the cell for further characterization. Conversion can be accomplished through the use of a specific linker that can be cleaved by incubation with a selective protease such as factor X, thrombin or any other selective proteolytic agent. It is also possible to include nucleic sequences that enable the genetic manipulation of the encoded protein in the vector (i.e., that allow excision of a surface attachment signal from the protein reading frame). Such genetic manipulation can be accomplished using a recombination system. A "recombination system", as used herein, refers to a system which allows for recombination between a vector and a chromosome for incorporation of a gene of interest. Recombination systems are known in the art and include, for example, Cre/Lox systems and FLP-IN systems (see, e.g., Abremski et al., *Cell*, 32: 1301-1311 (1983), and U.S. Pat. Nos. 4,959, 317; 5,654,182; and 5,677,177). For example, the insertion of one or more unique restriction sites, or cre/lox elements, or other recombination elements that enable the selective removal of an attachment signal and subsequent intracellular accumulation (or secretion) of the protein of interest at will. Further examples include the insertion of flanking loxP sites around an attachment signal (such as a transmembrane domain) allowing for efficient cell surface expression of a protein of interest. However, upon expression of the cre recombinase in the cell, recombination occurs between the LoxP sites resulting in the loss of the attachment signal, and thus leading to the release or shedding of the protein of interest.

A gene product of interest generated by the inventive method can be screened for a desired property (e.g., a selectable or improved phenotype) using a variety of standard physiological, pharmacological and biochemical procedures. Such assays include for example, biochemical assays such as binding assays, fluorescence polarization assays, solubility assays, folding assays, thermostability assays, proteolytic stability assays, and enzyme activity assays (see generally Glickman et al., *J. Biomolecular Screening*, 7(1): 3-10 (2002); Salazar et al., *Methods. Mol. Biol.*, 230: 85-97 (2003)), as well as a range of cell based assays including signal transduction, motility, whole cell binding, flow cytometry and fluorescent activated cell sorting (FACS) based assays. When the gene product is an antibody, or a fragment thereof, the phenotype/function of the antibody or fragment thereof can be further analyzed using art-recognized assays (e.g., enzyme-linked immunosorbant assays (ELISA), enzyme-linked immunosorbant spot (ELISPOT assay), gel detection and fluorescent detection of mutated IgH chains, Scatchard analysis, BIACOR analysis, western blots, polyacrylamide gel (PAGE) analysis, radioimmunoassays, etc. which can determine binding affinity, binding avidity, etc.).

Cells expressing a protein of interest encoded by a synthetic or semi-synthetic library as described herein can be enriched any art-recognized assay including, but not limited to, methods of coupling peptides to microparticles.

Many FACS and high throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like. Exemplary screening assays that can be used in the context of the inventive method are described in U.S. Patent Application Publication 09/0075378 and International Patent Application Publications WO 08/103475 and WO 08/103474.

Once a population of cells of interest has been obtained, the nucleic acid sequences of interest can be rescued and the corresponding mutations sequenced and identified. For example, total mRNA, or extrachromosal plasmid DNA can be amplified by co-expression of SV40 T antigen (*J. Virol.*, 62(10): 3738-3746 (1988)) and/or can be extracted from cells and used as a template for polymerase chain reaction (PCR) or reverse transcriptase (RT)-PCR to clone the modified nucleic acid sequence using appropriate primers. Mutant nucleic acid sequences can be sub-cloned into a vector and expressed in *E. coli*. A tag (e.g., His-6 tag) can be added to the carboxy terminus to facilitate protein purification using chromatography. The resulting data can be used to populate a database linking specific amino acid substitutions with changes in one or more of the desired properties. Such databases can then be used to recombine favorable mutations or to design next generation polynucleotide library with targeted diversity in newly identified regions of interest, e.g. nucleic acid sequences which encode a functional portion of a protein.

When the gene product of interest is an antibody, or fragment thereof, DNA can be extracted by PCR using variable heavy chain ($V_H$) leader region and/or variable light chain ($V_L$) leader region specific sense primers and isotype specific anti-sense primers. Alternatively, total RNA from selected sorted cell populations can be isolated subjected to RT-PCR using variable heavy chain ($V_H$) leader region and/or variable light chain ($V_L$) leader region specific sense primers and isotype specific anti-sense primers. Clones can be sequenced using standard methodologies and the resulting sequences can be analyzed for frequency of nucleotide insertions and deletions, receptor revision and V gene selection.

Cells can then be re-grown, SHM re-induced, and re-screened over a number of cycles to effect iterative improvements in the desired function. At any point, the nucleic acid sequence encoding the gene product of interest can be rescued and/or sequenced to monitor on-going mutagenesis.

The present invention additionally provides a method for mutating an organism to have a desired phenotype comprising expressing, or inducing the expression of, a functional AID mutant protein in the organism, whereupon expression of the functional mutant AID protein induces a mutation within the chromosomal DNA of the organism. The organism desirably is a prokaryote (e.g., bacteria) or a eukaryote. The eukaryote may be an invertebrate or a vertebrate, but preferably is a vertebrate. More preferably, the organism is a mammal. Most preferably, the organism is a mouse.

The vectors described herein which comprise a nucleic acid sequence encoding a functional mutant AID protein can be used in the aforementioned method of mutating an organism. Indeed, such vectors can be used to generate mice that are transgenic for a functional mutant AID protein using routine methods known in the art (see, e.g., *Methods Mol. Med.*, 99: 255-67 (2004)). In one embodiment, a vector comprising a nucleic acid encoding a functional mutant AID protein can be used to create a transgenic mouse wherein the endogenous AID gene is not disrupted. In another embodiment, a vector comprising a nucleic acid encoding a functional mutant AID protein can be used to create a transgenic mouse wherein the nucleic acid sequence encoding the functional AID mutant is inserted into the endogenous (i.e., chromosomal) AID locus to create a "knock-in" mouse, thereby preventing the expression of endogenous AID. In certain embodiments, the transgenic mouse comprises a functional mutant AID protein whose expression can be regulated by, for example, tissue-specific promoters or other inducible promoters (e.g., doxycycline or tetracycline (see, e.g., *Curr. Opin. Biotechnol.*, 13(5): 448-52 (2002)). In another embodiment, the organism comprises at least one nucleic acid sequence that has been codon-optimized for SHM to increase the number of SHM motifs according to the methods described above.

Whatever method is used to generate a transgenic mouse, expression of the functional mutant AID protein induces a mutation within the chromosomal DNA of the mouse. Once mutagenesis has occurred in an organism in accordance with the inventive method, cell or cells within the organism preferably are selected and/or screened for a desired phenotype using methods known in the art and described herein.

The inventive methods described herein also can be used to generate a transgenic animal which produces an antibody directed against an antigen of interest, or epitope thereof. In one aspect, the inventive methods preferably are used to generate a transgenic mouse which produces monoclonal antibodies. Methods for generating monoclonal antibodies are known in the art and are described in, for example, see, e.g., Köhler and Milstein, *Eur. J. Immunol.*, 5: 511-519 (1976), Harlow and Lane (eds.), Antibodies: A Laboratory Manual, CSH Press (1988), and C. A. Janeway et al. (eds.), Immunobiology, 5th Ed., Garland Publishing, New York, N.Y. (2001)).

The desired antibody can be any natural or synthetically derived antibody as described herein, or any antigen-binding fragment thereof. In addition, the antibody can be a non-human antibody, a humanized antibody, or a fully human antibody. Preferably, the antibody is a humanized antibody. "Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally also will comprise at least a portion of an immunoglobulin constant region (Fc), typically that of a human immunoglobulin. For further details, see Jones et al., *Nature,* 321: 522-525 (1986), Reichmann et al., *Nature,* 332: 323-329 (1988), and Presta, *Curr. Op. Struct. Biol.,* 2: 593-596 (1992). In another embodiment, a monoclonal antibody can be humanized by grafting mouse CDRs into a human antibody framework without substantially interfering with the ability of the antibody to bind antigen. Methods of preparing humanized antibodies are generally well known in the art and can readily be applied to the antibodies produced by the methods described herein.

In a preferred embodiment of the invention, humanized or fully human antibodies are generated using transgenic mice comprising a functional AID mutant protein that have been bred with a transgenic strain of mice in which endogenous mouse antibody gene expression is suppressed and effectively replaced with human antibody gene expression. Examples of transgenic mice wherein endogenous antibody genes are effectively replaced with human antibody genes include, but are not limited to, the HuMAb-Mouse®, the Kirin TC Mouse™, and the KM-Mouse® (see, e.g., Lonberg N. *Nat. Biotechnol.,* 23(9): 1117-25 (2005) and Lonberg N. *Handb. Exp. Pharmacol.,* 181: 69-97 (2008)).

The following examples further illustrate the invention but should not be construed as in any way limiting its scope.

EXAMPLE 1

This example demonstrates a method of screening for active mutators of DNA using a papillation assay.

Papillation assays have been used to screen for *E. coli* mutants that are defective in some aspect of DNA repair (Nghiem et al., *Proc. Natl. Acad. Sci. USA,* 85: 2709-17 (1988) and Ruiz et al., *J. Bacteriol.,* 175: 4985-89 (1993)).

For papillation assays, AID/APOBEC cDNAs in plasmid pTrc99[44] were transformed into *Escherichia coli* K12 strain CC102 araΔ(lacproB)$_{XIII}$ carrying F' lacI⁻ Z⁻ proAB⁺ episome in which the lacZ gene carries a GAG→GGG missense mutation at codon 461 (Cupples et al., *Proc. Natl. Acad. Sci. USA,* 86: 5345-49 (1989)), and plated on MacConkey-lactose agar (BD Biosciences) supplemented with ampicillin (100 μg/ml) and isopropyl β-D-1-thiogalactopyranoside (IPTG; 1 mM). Plates were incubated at 37° C. for 4 days with papilli becoming visible after 3 days.

The frequency of reversion of CC102 [pTrc99-AID/APOBEC] transformants to Lac⁺ was determined by plating cultures grown overnight to saturation in LB medium supplemented with ampicillin (100 μg/ml) and IPTG (1 mM) on M9+0.2% lactose agar. Mutation frequencies were measured by determining the median number of colony-forming cells that survived selection per 10⁷ viable cells plated with each median determined from 12 independent cultures. The identity of mutations was determined by sequencing PCR-amplified relevant sections of lacZ (5'-AGAATTCCT-GAAGTTCAGATGT (SEQ ID NO: 79) and 5'-GGAATTC-GAAACCGCCAAGAC (SEQ ID NO: 80)).

*E. Coli* cells which harbor a missense mutation within lacZ give rise to white colonies on MacConkey-lactose plates: within such white colonies, a small number of red microcolonies can often be discerned (papilli, typically 0-2 per colony) which reflect spontaneously-arising Lac⁺ revertants. Bacterial mutator clones which exhibit an elevated frequency of spontaneous mutation can be identified by virtue of an increased number of papilli.

The *E. Coli* strain CC102 carries a missense mutation in codon 461 of lacZ with glutamate being substituted by glycine owing to a A:T to G:C transition mutation (Cupples et al., *Proc. Natl. Acad. Sci. USA,* 86: 5345-49 (1989)). If expression of AID in CC102 were to increase the rate of cytosine deamination at codon 461, this might be expected to increase the frequency of Lac⁺ revertants. AID-expressing transformants of CC102 gave an increased frequency of papillation on MacConkey-lactose plates (FIGS. 1a, b). The number of papilli per colony as assayed after 6 days of incubation increased from 0-2 per colony to 8-10, which correlated with a more than threefold increase in the frequency of Lac⁺ revertants in overnight cultures as judged on minimal-lactose plates. Sequence analysis of six such Lac⁺ revertants confirmed that they had indeed arisen through reversion at codon 461. The AID-related deaminases APOBEC1 (A1) and APOBEC3G (A3G) also triggered increased papillation when expressed in CC102 cells (FIG. 1b).

This assay was also used to determine whether active mutators could be isolated from a total splenic cDNA library. A human spleen cDNA library was introduced into CC102 cells and fifty thousand colonies were screened for enhanced papillation. Thirty-six possible candidates were identified, which were retested by streaking on MacConkey lactose plates. Only two colonies were confirmed as giving increased papillation. Sequence analysis revealed that they carried distinct cDNAs derived from APOBEC3G. FIG. 1c depicts wild-type full length APOBEC3G mRNA and the two APOBEC3G cDNAs obtained in the human spleen cDNA library screen, wherein nucleotide residues are numbered relative to the start of the open reading frame (+1).

This example demonstrates that an *E. Coli* papillation assay can be used as a high throughput screen for active mutators.

EXAMPLE 2

This example demonstrates an assay to identify AID mutants.

First and second generation human AID mutant libraries were generated by error-prone PCR using Taq polymerase (2.5 U; Bioline) on 1 ng of template DNA with 1 μM forward and reverse primers (5'-ATGGAATTCATGGACAGC-CTCTTG (SEQ ID NO: 81); 5'-CT-GAAGCTTTCAAAGTCCCAAAGTA (SEQ ID NO: 82)), 250 μM-dNTPs, 10-mM-MgCl2 in Taq buffer at 94° C. (2 min), followed by 30 cycles of 94° C. (30 s), 65° C. (30 s) and, 72° C. (1 min). The third generation human AID mutant libraries were generated using Genemorph II Random Mutagenesis Kit (Stratagene) on 0.1 ng DNA template according to the manufacturer's instructions.

Papillation assays were performed as described in Example 1, except that plates were incubated at 37° C. for 3-6 days with papilli becoming visible after 3 days and their numbers increasing until day 7. For analysis of arabinose-inducible expression, AID was expressed in plasmid pBAD30 (Guzman et al., *J. Bacteriol,* 177: 4121-30 (1995)).

The frequency of reversion of CC102 [pTrc99-AID] transformants to Lac⁺ was determined as described in Example 1, whereas mutation to rifampicin resistance (Rif^r) was assessed following transformation into *E. Coli* strain KL16 (Hfr (PO-45) relA1 spoT1 thi-1) and colony growth in the presence of rifampicin (50 μg/ml) and arabinose (0%-0.5%). Mutation frequencies were measured as described in Example 1, and the identity of mutations was determined by sequencing of PCR-amplified relevant sections of lacZ as described in Example 1 or PCR-amplified relevant sections of rpoB (5'-TTGGCGAAATGGCGGAAAACC-3' (SEQ ID NO: 83) and 5'-CACCGACGGATACCACCTGCTG-3' (SEQ ID NO: 84)).

The results shown in FIG. 1d and FIG. 2 demonstrate that this assay can identify AID upmutants. A total of sixty thousand colonies from four independent PCR-mutagenesis experiments yielded 13 clones which exhibited increased papillation on MacConkey-lactose plates. Nine of these mutants were then tested in re-transfected E. Coli strain KL16 for the frequency with which they yielded rifampicin-resistant colonies, and all nine exhibited an increased frequency of mutation at the rpoB locus.

The AID cDNAs from two of the first-generation upmutants, i.e., Mutt and Mut7, were then themselves subjected to PCR mutagenesis and second-generation mutants exhibiting enhanced papillation were obtained (FIG. 2). The high papillation exhibited by these second generation mutants made it difficult to visually discern any additional increases in papillation. In order to screen for further enhancement of mutator activity in a third round of mutation/selection, cDNAs encoding AID Mut1.1 and Mut7.3 were cloned into an arabinose-inducible expression vector such that the number of papilli obtained in CC102 transformants could be regulated by varying the concentration of arabinose in the medium (FIG. 1e). A third generation of AID upmutants was obtained by screening for papillation under low (0.02%) arabinose, some of which gave a mutation frequency that was nearly 400-times greater than the wild-type AID as judged by the frequency of mutation to rifampicin resistance (FIG. 2).

FIG. 2 depicts the dynasty of AID upmutants selected by the papillation screen. Upmutants obtained in three successive rounds of mutagenesis with mutants obtained from individual PCR-mutagenesis experiments grouped as families of siblings. The additional amino acid substitutions introduced in each round of mutagenesis are indicated with the numbers below the indicated substitutions giving the mean frequency of mutation to Rif$^r$ relative to vector. * indicates a C-terminal truncation caused by introduction of a premature stop codon at the indicated codon. Individual mutants are numbered according to their dynastic origin: thus, for example, Mut7 (K10E/E156G) is the parent of Mut7.1 (K10E/E156G/F115Y).

Several of the third generation mutants appeared to exhibit toxicity in E. Coli as judged by smaller colony size when grown under inducing conditions; this was accompanied by a reduced viable cell count in bacterial cultures grown to saturation. This result is demonstrated in FIG. 1f, which depicts bacterial titers in CC102 transformants expressing different AID upmutants grown to saturation in LB/Amp under conditions of IPTG induction relative to the titers obtained from cultures grown in the absence of induction. This toxicity might have caused some highly papillating mutants to give anomalously low frequencies of mutation to Rif$^r$ (e.g., Mut7.3.4; FIG. 2) with AID expression possibly being downregulated during overnight culture.

This example demonstrates that the E. Coli papillation assay can identify functional AID mutant proteins that exhibit at least a 10-fold improvement in activity compared to a wild-type AID protein.

EXAMPLE 3

This example demonstrates that the bacterial papillation assay can identify hot spots for AID mutants having increased activity.

FIG. 3a compares the primary sequence of human AID (SEQ ID NO: 2) containing specific mutations that confer increased activity with upmutations in the pufferfish (Fugu) AID sequence. Mutations at asterisked residues are deduced to confer increased mutator activity since they constitute the sole difference between at least one pair of AID sequences exhibiting >2-fold difference in mutation frequencies at rpoB. Residues that are double underlined indicate sites where substitutions have been identified in multiple independent upmutants but in the presence of one or more other substitutions. The box above or below the asterisked or double underlined residues shows the identity of the substitution mutations and the frequency with which each substitution was detected in the total of nine independent libraries. Residues where the corresponding position in fugu AID also appears to be a site of selected upmutation, as judged by the fact that it is either the sole mutation identified in a fugu upmutant or that the substitution was identified (albeit with others) in multiple fugu upmutants, are identified by a bold, single underline. The zinc-coordination motifs (HVE and PCYDC (SEQ ID NO: 86)) and regions of suggested polynucleotide contact (FCEDRKA (SEQ ID NO: 87) (Cupples et al., Proc. Natl. Acad. Sci. USA, 86: 5345-49 (1989); Conticello et al., Nat. Struct. Mol. Biol., 14: 7-9 (2007); and Chen et al., Nature, 452: 116-119 (2008)), are highlighted by boxes.

Apart from the premature stop codon mutations identified in three of the AID upmutants (Mut5, Mut1.3, and Mut1.5), analysis of the sequences of the various AID upmutants revealed a striking preference for certain amino acid substitutions. For example, the K34E, T82I, and E156G substitutions (each of which is sufficient on its own to increase AID activity) were selected in independent experiments. These mutations were not found amongst sequences of 48 random (i.e., unselected) clones from the PCR-generated libraries, where a wide spectrum of mutations was observed without indications of any major hotspots of the mutagenesis procedure itself. Thus, the repeat identification of a small number of amino acid substitutions suggests that there are a limited number of single amino acid substitutions in AID that yield increased papillation.

Although in some cases (especially in the third generation) the multiplicity of mutations introduced in a single round prevents unambiguous identification of those mutations responsible for the increased papillation, in many cases the relevant upmutation can be definitively identified because it constitutes the sole difference between a pair of differently-papillating AID sequences or (somewhat less definitively) because it was independently obtained in multiple PCRs. The locations of such upmutations are depicted in FIG. 3a, where it is seen that whereas some are located around the zinc-coordination motif in the vicinity of the likely catalytic site (V57A; T82I), others are in a region equivalent to a portion of APOBEC3s that have previously been suggested to be involved in polynucleotide binding (F115Y; K120R) (Conticello et al., Nat. Struct. Mol. Biol., 14: 7-9 (2007); Chen et al., Nature, 452: 116-119 (2008); and Holden et al., Nature, 456: 121-124 (2008)), several are clustered in regions whose function is unknown.

This example demonstrates a method for identifying AID mutants having increased activity.

EXAMPLE 4

This example demonstrates that the upmutations identified in the bacterial papillation screen increase the specific activity of AID.

GST-AID fusion proteins were purified from pOPTG-AID transformants of E. coli strain Rosetta (DE3) pLysS (pOPTG vector a gift from O. Perisic, Cambridge, UK). Cells were grown at 37° C. in 2×TY containing 100 µg/ml ampicillin and 100 nM $ZnCl_2$ until the culture reached an absorbance of 0.8 at 600 nm when it was induced with 1 mM IPTG for 16 h at 18° C. and the pelleted cells then lysed by a 30 min incubation on ice in lysis buffer (20 mM-Tris pH 7.4, 100 mM-NaCl, 0.1% Triton X-100, 5 mM-DTT, 4 µg/ml RNase A and complete EDTA-free protease inhibitor cocktail (Roche)) followed by sonication. Cell lysates were clarified by centrifugation (95,000 g; 1 h) and GST-AID was purified from these lysates by absorption onto glutathione-Sepharose (Amersham Pharmacia) at 4° C. for 5 h and elution following extensive washing with lysis buffer supplemented with 50 mM reduced glutathione lacking Triton X100. Eluted samples were stored at 4° C. for up to one week.

The abundance of GST-AID fusion protein was monitored by Western blot (FIG. 3b). Initial screening of the sonic extracts of a large number of upmutants did not reveal any which exhibited a significant increase in the fractional yield of soluble protein as judged by Western blot analysis.

Deaminase activity of semi-purified GST-AID (100-400 ng) was assayed at 37° C. in 10 µl of reaction buffer (8 mM-Tris, pH 8.0, 8 mM-KCl, 10 mM-NaCl, 2.5 mMEDTA, 0.2 mM-dithiothreitol, 5 µg RNase A and 0.4 units uracil-DNA glycosylase (NEB)) with 0.5 pmol oligodeoxyribonucleotide (fluorescein-5'-ATATGAATAGAATA-GAGGGGTGAGCTGGGGTGAGCTGGGGTGAG-3'-biotin (SEQ ID NO: 85)). Reactions were terminated at indicated times by addition of an equal volume of loading dye (formamide, 0.5 mM EDTA) and heating at 98° C. for 3 minutes. The resultant cleaved oligonucleotides were subjected electrophoresis in 10% PAGE-urea gels and fluorescence detected with a Typhoon Phosphoimager (Molecular Dynamics). The extent of deamination was determined from the scanned images, expressing the pixel volume of the cleaved product bands (following background subtraction) as a percentage of the combined pixel volume of product and residual substrate bands.

When GST-fusion proteins were generated from human upmutants Mut1.1 and Mut7.3.6, a clear increase in specific activity was evident as judged by in vitro deamination assays performed on an oligonucleotide substrate (FIGS. 3b,c). From analysis of initial rates, the specific deamination activity of these upmutants had increased some five-fold compared to wild-type.

Transition mutations at any one of 11 C:G pairs within rpoB can give rise to $Rif^r$. The distribution of such mutations amongst $Rif^r$ colonies is shown for AID upmutants Mut8, 1.1, 1.2, 7.3.5 and 7.3.6 in FIG. 3d. The increased specific activity does not appear to have been accompanied by any gross change in the target specificity since analysis of the rpoB mutations obtained using several human AID mutants did not reveal any major difference in mutation spectrum (FIG. 3d).

This example demonstrates that the mutations identified in the bacterial papillation screen increase the specific activity of AID.

EXAMPLE 5

This example describes the generation of mutations in pufferfish (fugu) AID that result in increased AID activity.

Libraries containing mutants of fugu AID were generated using Genemorph II Random Mutagenesis Kit (Stratagene) on 0.1 ng DNA template according to the manufacturer's instructions. A bacterial papillation screen of the library of fugu mutants was performed as described in Example 1. The frequency of mutation to $Rif^r$ relative to vector-only transformants at either 18° C. or 37° C. is shown in FIG. 4b for E. coli K16 transformed with plasmids encoding wild type or mutated fugu AID as indicated. Derivatives of Mut4.3 and 4.10 were constructed in which the nonsense mutation at 190 had been reverted, thereby yielding a wild-type C-terminus.

AID from pufferfish (which live at around 26° C.) exhibits little bacterial mutator activity when assayed at 37° C., whereas mutator activity can be detected at 18° C. (Conticello et al., Mol. Biol. Evol., 22: 367-377 (2005)). Mutants of fugu AID that gave robust papillation at 37° C. were identified in a bacterial papillation assay. As shown in FIG. 4a, all the first generation mutants isolated harbored C-terminal truncation mutations (indicated by a "*", wherein "*a" and "*b" indicate different single nucleotide substitutions at codon 190 causing the premature stop codon), with the six mutants obtained harboring 5 distinct truncation mutations. Mutations causing the C-terminal region to be read out-of-frame were also identified, which are designated "Ins200a" and "Ins200b" in FIG. 4a to indicate different single nucleotide insertion mutations at codon 200.

A variety of amino acid substitutions, however, could then lead to enhanced papillation in second generation mutants (FIG. 4a), with several of these occurring at positions analogous to the upmutations identified in human AID (FIGS. 3a and 4a). Thus, the mutation (C88L) responsible for the increased activity of fugu AID Mut1.3 occurs at the equivalent position to the T82I mutation in human AID. Similarly, residues F121, L124 and L128 in fugu AID (each of which is a target for mutation in either two or three fugu upmutants) are all located in a stretch of fugu AID corresponding to 115-121 in human AID where upmutations were also obtained.

Although C-terminal truncations were detected amongst the panel of human AID upmutants, and such truncations have previously been shown to give higher mutator activity in E. coli (Barreto et al., Mol. Cell, 12: 501-508 (2003); Ta et al, Nat. Immunol., 4: 843-848 (2003)), all the first generation mutants of fugu AID selected at 37° C. carried truncations at the C-terminus. One plausible explanation for this observation is that C-terminal mutations underpinned increased thermal stability and that the amino acid substitutions giving rise to increased papillation in the second generation fugu upmutants might not have been discernible at 37° C. in the absence of a C-terminal truncation mutation. However, this does indeed appear a likely explanation. The C88L and L128P substitutions both gave increased frequency of mutation to $Rif^r$ as assayed at 18° C. in the presence or absence of a C-terminal truncation. However, when assayed at 37° C., these amino acid substitutions did not give any discernible increase in mutation frequency in the absence of the C-terminal truncation (FIG. 4b).

This example demonstrates that mutations in pufferfish (fugu) AID that increase its activity are analogous to certain mutations identified in human AID.

EXAMPLE 6

This example demonstrates a method of enhancing antibody diversification in cells using a functional AID mutant protein of the present invention.

Somatic mutation of the IgV was assayed by monitoring surface IgM-loss in $AID^{-/-}$ $\phi V^{-/-}$ $sIgM^+$ DT40 cells (Teng et al., Immunity, 28: 621-629 (2008)) that had been stably transfected with AID-encoding vectors based on pExpress-Puro2 by flow cytometry. For each construct, the percentage of sIgM⁻ cells was monitored in 12-24 independent transfectants that had been expanded under selection (0.25 µg/ml puromycin) for 3 weeks prior to flow cytometry.

Mutations in the IgVλ region were characterized by sequencing genomic DNA that was PCR-amplified from either 100,000 unsorted or from (GFP⁺; sIgM⁻)-sorted cell equivalents (Sale et al., *Nature*, 412: 921-926 (2001)).

For assaying class-switching, surface IgG1 expression was analyzed by flow cytometry in B cells that had been purified from AID⁻/⁻ mice and cultured in the presence of LPS+IL4 (48 h) following a 24 h-infection with AID encoding retroviruses as previously described (Di Noia, *J. Exp. Med.*, 204: 3209-3219 (2007)). To facilitate a diminution in the extent of AID overexpression in the transduced B cells, a retroviral vector with a mutated Kozak sequence was used as described (McBride et al., *J. Exp. Med.*, 205: 2199-2206 (2008)). AID abundance in extracts prepared by heating cells (10⁶) in 50 µl of reducing SDS-sample buffer was monitored following SDS/PAGE by Western blot analysis using rabbit anti-AID antiserum (Abcam); GFP was detected using HRP conjugated goat anti-GFP antiserum (Abcam).

Mutants 3 (T82I), 8 (K34E, K160E) and 7.3 (K10E, E156G, T82I) were expressed in an AID deficient chicken DT40 B cell line in which somatic mutation of the IgV can be inferred from the frequency of generation of sIgM-loss variants (Arakawa et al., *PLoS Biol.*, 2: E179 (2004)). Both Mut3 and Mut7.3 appeared to give significantly enhanced somatic mutation as judged by this sIgM-loss assay (FIG. 5a). Furthermore, sequence analysis revealed that after one month of clonal expansion, cells expressing these mutant AIDs did indeed carry a higher mutation load in the IgGλ gene than did control cells expressing the wild type enzyme (FIG. 5b). Not only did a higher proportion of sequences carry mutations but those that did carry mutations also carried a higher mutation load. This effect is particularly marked when account is taken of the fact that the mutant AID is expressed at lower abundance than its wild type counterpart in these transfectants. In contrast, mutant 8 did not give enhanced somatic mutation indicating that the K34E and/or K160E substitutions are likely to diminish aspects of AID's function in B cells. Interestingly, Mut8 polypeptide is found at much higher abundance in the DT40 transfectants than are the Mut3 or 7.3 polypeptides. This is consistent with observations in other work (e.g., Conticello et al., *Mol. Cell*, 31: 474-484 (2008)) that AID mutants which exhibit compromised activity in antibody diversification/genomic mutation in DT40 cells tend to be expressed at higher abundance without any evident alteration in intracellular localization. One possible explanation for these differences in expression levels is that, in cell transfectants, there is selection against cells expressing high levels of AID proteins which are active in chromosomal mutation.

An assay based on retroviral transduction of the mutant enzymes into AID-deficient mouse B cells was used to assay the activity of the mutant AID in class switch recombination. In order to limit the degree of over expression of AID which might otherwise saturate the switching assay, the assay was performed using both the conventional pMX-Ig virus as well as a variant in which the transduced AID is expressed at lower levels through mutation of the Kozak sequence (McBride et al., *J. Exp. Med.*, 2005: 2585-2594 (2008)). As indicated in FIG. 5c, which depicts representative flow cytometry plots of switching to IgG1 wherein 'mK' indicates where transduction was performed using vectors with a mutated Kozak sequence, Mut7.3 was more effective in promoting class-switch recombination than the wild type counterpart although expressed at lower levels.

This example demonstrates the use of a functional mutant AID protein to enhance antibody diversification in accordance with the inventive method.

EXAMPLE 7

This example demonstrates that AID mutants increase chromosomal translocations.

Figure 6:
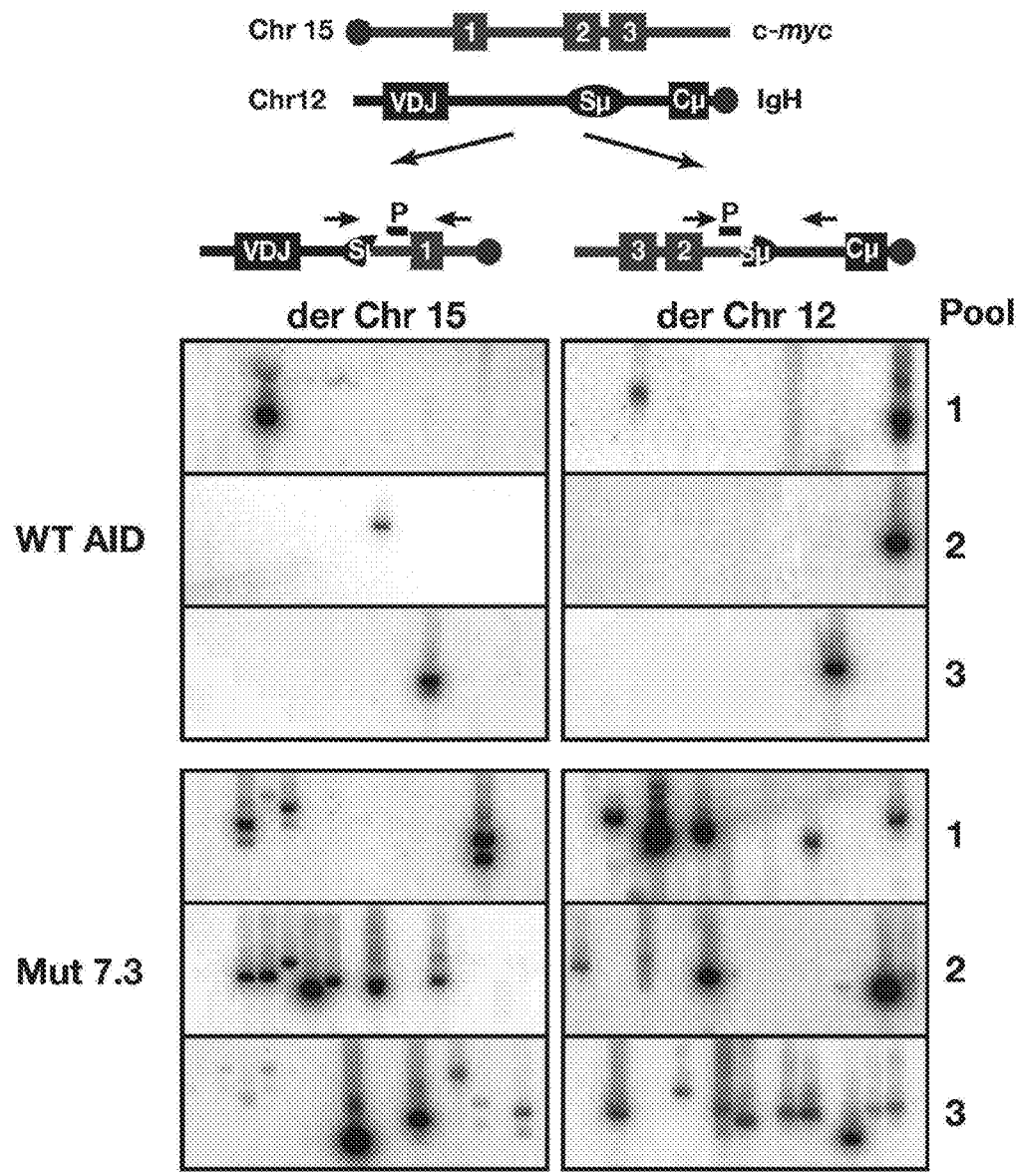
FIG. 6 provides a diagram that illustrates a reciprocal translocation between c-myc and IgH locus and depicts the primers (arrows) and probes (P) used for detection of the translocation.

A PCR-based assay (Janz et al., *Proc. Natl. Acad. Sci. USA.*, 90: 7361-7365 (1993)) was used to detect c-myc/IgH translocations in B cells. B cells from AID-deficient mice were transduced with AID-expressing retrovirus and cultured in medium containing LPS (20 µg/ml) and IL4 (50 ng/ml) as described for the class-switching assays in Example 6, seeding 8×10⁵ cell/ml in 6-well plates. Genomic DNA from 2×10⁵ cells that had been prepared using Direct-PCR (Viatech) from sorted GFP⁺ cells 36 h after transduction was subjected to two rounds of nested PCR with Expand Long Template PCR system (Roche) followed by Southern blotting to amplify and detect both der12 c-myc/Igµ and der15 c-myc/Igµ translocations and the specific products as described (Ramiro et al., *Nature*, 440: 105-109 (2006)). FIG. 6 (top) depicts the scheme of reciprocal translocation between the c-myc and IgH loci and indicates the primers used for PCR amplification (arrows) and the probes (P) used for Southern blot hybridization.

B cells from AID-deficient mice were retrovirally transduced for AID expression and cultured for 1-2 days in vitro. AID Mut7.3 gave rise to a significantly higher proportion of cultures containing c-myc/IgH translocations than did the wild type enzyme (FIG. 6 (bottom)).

This example demonstrates a method of increasing chromosomal translocations using a functional AID mutant protein.

EXAMPLE 8

This example demonstrates that nucleic acid sequences encoding AID mutants with increased activity are closer to the nucleic acid sequences of APOBEC3 deaminases than wild-type AID.

A Web LOGO alignment (Crooks et al., *Genome Research*, 14: 1188-1190 (2004)) was performed (FIG. 7), which depicts amino acid conservation surrounding the major sites of upmutation of AID and the homologous regions in the Z1, Z2 and Z3 domains of mammalian APOBEC3s (cow, sheep, pig, dog, peccary, horse, cat, dog, mouse, rat, human and macaque: sequence accession numbers are provided in FIG. 8). Any sequence with over 90% amino acid identity to any other sequence was discarded from generation of the LOGO profiles. The AID upmutations are shown in the box above the numbered residues. Arrows at the bottom of the alignment highlight the homologous residues in the APOBEC3s.

Figure 7:
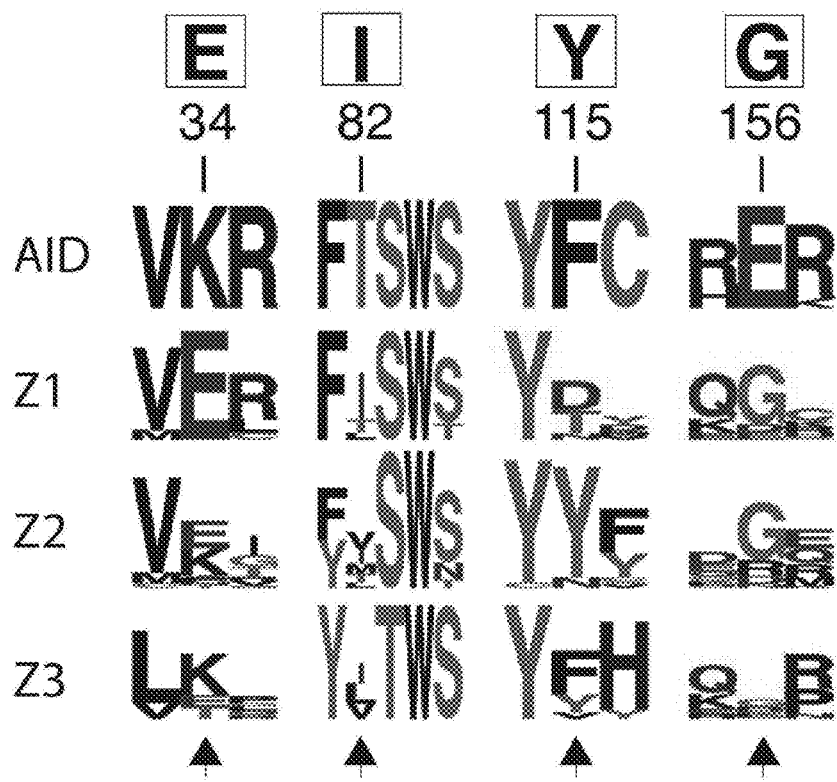
FIG. 7 is a LOGO alignment which illustrates that the functional mutations identified in the bacterial papillation screen bring the AID sequence closer to that of APOBEC3s.

FIG. 7 illustrates that APOBEC3 family proteins are rapidly evolving and present in multiple copies in higher animals: their zinc coordination domains can be classified by sequence homology into one of three subgroupings (Z1, Z2 and Z3) (Conticello et al., *Mol. Biol. Evol.*, 22: 367-377 (2005)). Alignment of AID sequences with those of the APOBEC3s revealed that most of the frequently selected upmutations in human AID served to bring the sequence of AID closer to that of its APOBEC3 relatives (FIG. 7). In fact, whereas the AID upmutation at F115 substitutes the amino acid preferred at the corresponding position in APOBEC3 Z2 domains (Y), the upmutations at K34, T82 and E156 all substitute to the preferred amino acid at the corresponding position in the APOBEC3 Z1 domains. Interestingly, it is these Z1 domains which were found to be the most catalytically active of APOBEC3 domains (LaRue et al., *J. Virol.*, 83: 494-497 (2009)). Thus, it appears that whereas the deamination activity of AID can be artificially increased by specific upmutations, such upmutations may have been counterselected during the evolution of AID but not during the evolution of APOBEC3s.

This example demonstrates that nucleic acid sequences encoding AID mutants with increased activity are closer to the nucleic acid sequences of APOBEC3 deaminases than wild-type AID.

EXAMPLE 9

This example compares human (SEQ ID NO: 2) and pufferfish (fugu) (SEQ ID NO: 13) AID upmutations.

Figure 9:
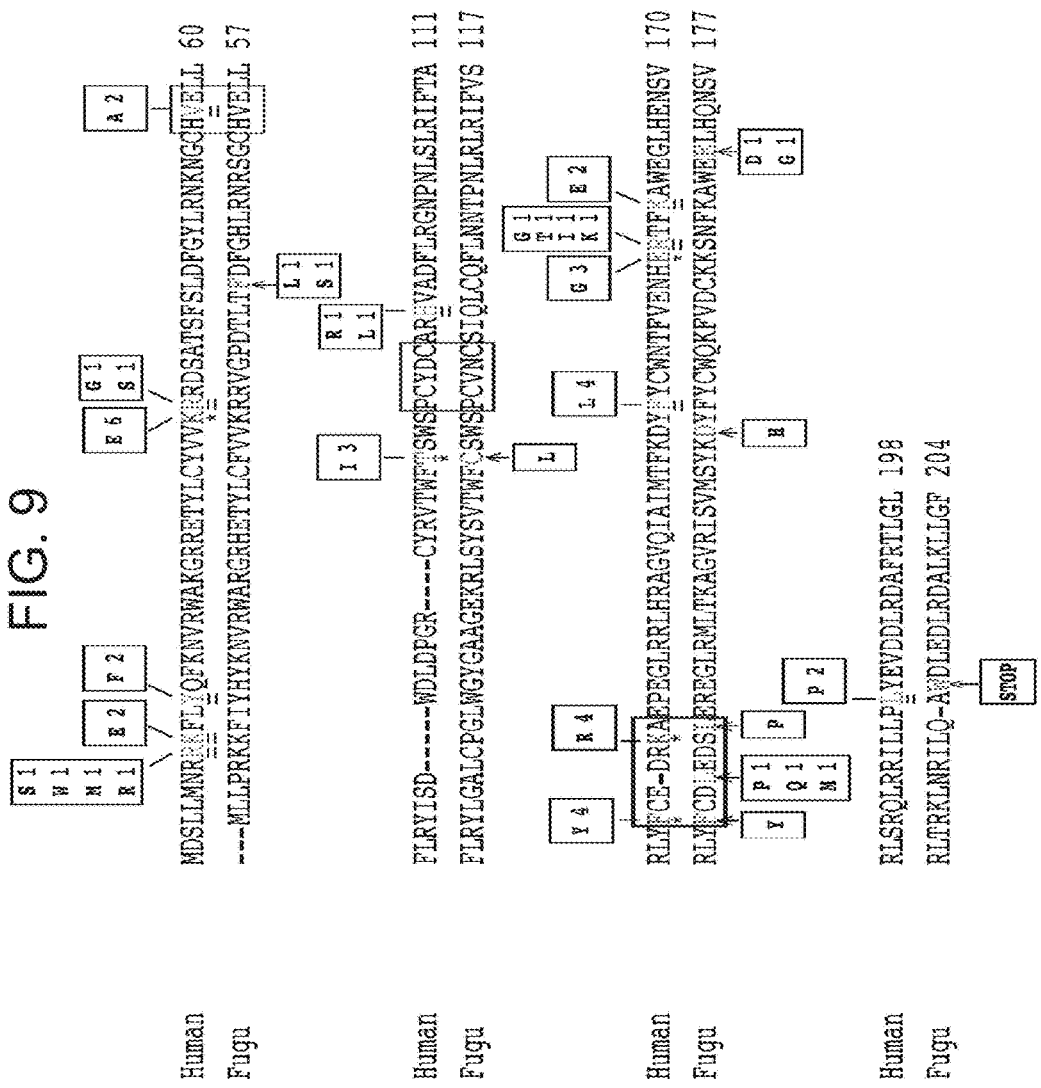
FIG. 9 is a sequence diagram of human AID (SEQ ID NO: 2) and pufferfish (fugu) AID (SEQ ID NO: 13) that illustrates the positions and identities of the functional mutations that were identified.

Human and fugu AID primary sequences are aligned using ClustalW2 (e.g., Larkin et al., *Bioinformatics*, 23: 2947-2948 (2007)) (FIG. 9). The human AID upmutations are indicated by an asterisk or double underlining as described in Example 3 (FIG. 3a). The fugu AID upmutations are indicated by a carrot ("^"), having been identified either because they constitute the sole mutation in a fugu upmutant or because the residue was mutated in multiple fugu upmutants. The nature of the substitutions are indicated in boxes above or below the highlighted residues as in FIG. 3a. The zinc-coordination motifs (HVE, PCYDC) and regions of suggested polynucleotide contact (FCEDRKA) are boxed.

This example compared human and pufferfish (fugu) AID upmutations.

EXAMPLE 10

This example describes a method of generating a functional AID mutant comprising replacing an amino acid sequence of a wild-type AID protein with a corresponding amino acid sequence from an AID homolog.

Human AID mutants in which amino acid residues 115-123 have been replaced by equivalent regions from APOBEC3C (AID/3C), APOBEC3F (AID/3F), and APOBEC3G (AID/3G) were cloned into a bacterial expression plasmid. The mutator activity of these modified AID sequences was assayed by monitoring the frequency with which they yielded colonies resistant to rifampicin after transformation into *E. coli*. Specifically, *E. coli* strain KL16 [Hfr (PO-45) relA1 spoT1 thi-1] transformed with pTrc99/AID plasmids was grown overnight to saturation in LB medium supplemented with ampicillin (100 μg ml$^{-1}$) and isopropyl β-D-1-thiogalactopyranoside (IPTG; 1 mM), and plated on LB low salt agar containing ampicillin (100 μg ml$^{-1}$) and rifampicin (50 μg ml$^{-1}$). Mutation frequencies were measured by determining the median number of colony-forming cells that survived selection per 10$^7$ viable cells plated with each median determined from 12 independent cultures. The identity of mutations was determined by sequencing the relevant section of rpoB (typically from 25-200 individual colonies) after PCR amplification using oligonucleotides 5'-TTGGCGAAATGGCGGAAAACC (SEQ ID NO: 88) and 5'-CACCGACGGATACCACCT-GCTG-3' (SEQ ID NO: 89). Whilst the AID/3C and AID/3F proteins retained good mutator activity, AID/3G gave rifampicin resistant colonies at a frequency indistinguishable over background. Rifampicin resistance is conferred by one of a limited number of mutations in rpoB with the nature of the mutations obtained giving insight into the target specificity of the deaminase (Harris et al., *Mol. Cell.*, 10: 1247-1253 (2002)). Wild-type AID prefers to deaminate the C residues at rpoB position 1576 (C1576), which has a 5'-flanking purine (G) residue. In contrast, the AID variants in which residues 115-123 have been replaced by corresponding regions from APOBEC3C/F/G showed a preference (as do the APOBEC3s themselves) for pyrimidines at the −1 position. Thus, AID/3C and AID/3F exhibited a shift in the spectrum of rpoB mutations to favor targets with a 5'-T (C1535, C1565 and C1592), while the AID/3G transformants almost solely targeted C1691, which has a 5'-C.

This results of this example demonstrate that replacement of amino acid residues 115-123 of human AID with corresponding sequences from APOBEC3 proteins alters the specific activity of AID.

EXAMPLE 11

This example describes a method of generating a functional AID mutant comprising replacing an amino acid sequence of a wild-type AID protein with a corresponding amino acid sequence from an AID homolog.

Although Example 10 demonstrates that the mutator activity of AID/3G is sufficient to yield a shift in the distribution of rpoB mutations observed in rifampicin-resistant *E. coli*, the mutator activity of the AID/3G mutant is considerably lower than that of wild-type AID, since it does not yield a total frequency of mutation to rifampicin-resistance that is above background. To improve the mutator activity of the AID/3G mutant, two AID/3G upmutants were generated (designated AID1/3G and AID2/3G) in which three additional amino acid substitutions (i.e., AID1: K10E, T82I, E156G; AID2: K34E, E156G, R157T) were introduced into these proteins. Both of these AID/3G upmutants appeared to retain the parental AID/3G protein's preference for a 5'-flanking C residue as determined by the rpoB mutation spectrum.

AID variants (designated AID*, AID*/3F, AID1*/3G, etc.) also were generated in which the C-terminal portion of AID (which includes its nuclear-export sequence) was deleted. The C-terminal truncation does not yield a detectable effect on AID mutational target site preference in bacterial mutation assays.

To analyse the biochemical target specificity of the above mutant AIDs in greater detail, the various AID enzymes were partially purified from *E. coli* extracts as recombinant GST-fusion proteins and used to deaminate single-stranded lacZ target DNA in the context of the M13 gapped duplex assay (Bebenek and Kunkel, *Methods Enzymol.*, 262: 217-232 (1995); Pham et al., *Nature*, 424: 103-107 (2003)). In this assay, recombinant GST-AID is incubated with gapped duplex M13lacZ DNA, which is then transformed into *E. coli*.

Analysis of 30-50 mutated M13lacZ clones in each experiment yielded databases of 471-685 mutations, all of which were transitions at C:G pairs. In the case of AID1, 74% of the C mutations were at sites flanked by a 5'-purine. In contrast, the AID mutants carrying transplanted segments from APOBEC3 proteins showed a shift towards a preference for a flanking pyrimidine, which was especially marked in the case of the AID/3C and AID/3G proteins (85% and 77% pyrimidine, respectively). This change in flanking nucleotide preference was accompanied by a change in the distribution of mutations along lacZ. Given that for most of the AID variants, the mutated sequences carried an average of 10-16 transition mutations over the 475 nucleotide stretch of single-stranded substrate analyzed, the mutations observed largely reflected the intrinsic preference of the mutational process without extensive skewing by virtue of the selection for lacZ inactivation.

The results of this example confirm that replacement of amino acid residues 115-123 of human AID with corresponding sequences from APOBEC3 proteins alters the specific activity of AID

EXAMPLE 12

This example demonstrate that mutant AID proteins exhibit altered mutation spectra in B cells.

In order to ascertain whether changing the catalytic specificity of AID results in an alteration in the distribution of nucleotide substitutions introduced during SHM in B cells, the mutant AIDs described in Examples 10 and 11 were expressed in an AID-deficient, ΨV-deleted chicken DT40 B cell line. In the DT40 B cell line, the mutations are largely restricted to nucleotide substitutions at C:G pairs with little contribution from polymerase η-triggered hypermutation (Arakawa et al., PLoS Biol., 2: E179 (2004); Di Noia and Neuberger, Nature, 419: 43-48 (2002); Sale et al., Nature, 412: 921-926 (2001)), meaning that mutations at C:G can largely be ascribed to the direct effects of AID rather than possibly being a consequence of a second phase of mutation creation. The frequency of SHM at the IgV can be inferred from the frequency of generation of sIgM-loss variants (Buerstedde et al., EMBO J., 9: 921-927 (1990); Sale et al., Nature, 412: 921-926 (2001)). This assay demonstrated that both AID/3C and AID/3F are proficient in SHM. Indeed, AID/3C is even more potent than the wild-type enzyme, especially when the lower abundance of the AID/3C polypeptide in the B cell extracts is taken into account. The low abundance of AID/3C was evident in multiple independent transfectants. The reason for this low expression may reflect cytotoxicity of excessive DNA deaminase activity.

In contrast to the AID/3C and AID/3F mutants, the AID1/3G mutant gave only a very low frequency of sIgM-loss variants. However, this frequency was considerably enhanced by deleting the AID C-terminal portion.

To characterise the IgV gene hypermutation spectrum in the DT40 B cell transfectants expressing the various modified AID proteins, the IgVλ segment from multiple independent transfectants for each expression construct was PCR amplified and sequenced after eight weeks of clonal expansion. The results revealed that the modifications of the AID active site resulted in a substantial alteration to the IgVλ mutation spectrum. Thus, AID/3C and AID1*/3G largely targeted C residues with a 5'-flanking pyrimidine residue (68% and 75% respectively), in contrast to the wild-type enzyme in which only 19% of the mutations are targeted to C residues with a 5'-flanking pyrimidine. This significant change in mutation spectrum is evident both in the composite datasets as well as in each of those from independent clones. In contrast, AID/3F maintained the preference of the parental enzyme for a flanking purine residue but, as found in the in vitro assay on the gapped duplex lacZ substrate (Example 11) there is shift towards a preference for a flanking guanine rather than adenine.

The change in mutational targeting as judged by the nature of the 5'-flanking nucleotide broadly correlated with an altered mutational spectrum as determined by the distribution of nucleotide substitutions along the IgVλ segment. Thus, for example, the IgVλ mutation hotspots were found at distinct locations when comparing wild-type AID with AID1*/3G. With wild type AID (as well as in the AID1 upmutant), clusters of hotspots were evident within CDR1, towards the 5'-side of CDR2, and also within CDR3, with these hotspots mostly conforming to a WRC consensus as observed previously (Arakawa et al., PLoS Biol., 2: E179 (2004); Sale et al., Nature, 412: 921-926 (2001); Saribasak et al., J. Immunol., 176: 365-371 (2006); Wang et al., Nat Struct Mol. Biol., 16: 769-76 (2009)). In contrast, the IgVλ mutations obtained using AID1*/3G showed reduced clustering in CDR1 and CDR3, with a focus on hotspots with a 5'-pyrimidine flank and which are located in regions (FR1 and FR3) that are relatively spared by the wild type enzyme.

The results of this example demonstrate that changing the active site of AID modifies the mutation spectrum that is obtained both by DNA deamination in vitro and by antibody hypermutation in B cell transfectants.

EXAMPLE 13

This example describes the identification of "hotspots" of AID mutants.

Although the active site modifications in AID/3C and AID1*/3G resulted in a shift from a preference for a flanking 5'-purine to a flanking 5'-pyrimidine in both in vivo (DT40 IgVλ) and in vitro (gapped-duplex lacZ) mutation assays, the nature of the shift in the two assays was not equivalent. Thus, for AID/3G, although T is the flanking pyrimidine of choice in the DT40 IgVλ mutation spectrum, a flanking C is preferred in the in vitro assay. This discrepancy is substantially due to the skewing effect of a few major hotspots in the DT40 IgVλ spectrum, suggesting that some aspect of hypermutation in B cells might result in the creation of dominant hotspots which are not recapitulated in the in vitro gapped duplex assay.

To confirm this, the gapped duplex mutation assay was performed on an IgVλ (rather than lacZ) target sequence, and the resulting in vitro mutation spectrum was compared to that observed on the equivalent (non-transcribed) IgVλ DNA strand in DT40 B cells. Significant differences in mutational targeting were observed. These differences were similarly evident if the highly mutated sequences were excluded from the database used to deduce the patterns of in vitro mutational targeting.

To find out whether the differences in targeting reflects the fact that mutation in vivo likely occurs on transcribing double-stranded DNA, whereas the gapped duplex assay uses a single-stranded DNA target, mutational targeting was employed, using an assay described by Bransteitter et al., J. Biol. Chem., 279: 51612-21 (2004). This mutational targeting assay involves incubating recombinant AID with double-stranded DNA at the same time the target gene (lacZ) within the substrate is being transcribed from a linked T7 polymerase promoter. In this assay, AID1*/3G clearly differed from wild type AID, still preferring a 5'-pyrimidine, and especially a 5'-C, rather than the 5'-T that was observed in DT40 B cells. In order to assess mutational targeting within an IgVλ substrate in an in vitro transcription-coupled assay, the T7-linked assay was modified to create a substrate in which unselected mutations in short segments of IgVλ could be scored in clones that have suffered mutational inactivation of a closely linked GFP reporter gene. However, in such assays it was found that, as in the gapped duplex assay, the relative dominance of major hotspots at IgVλ positions 141 (with wild type AID) or 252 (with AID1*/3G) that was observed during hypermutation in DT40 cells was not recaptured. In fact, the mutational targeting in the transcription-linked assay appeared to be more similar to that obtained in the gapped duplex assay than to the pattern of mutational targeting observed in DT40 B cells. Thus, neither in vitro assay fully recapitulated the pattern of IgV hotspot dominance observed in B cells.

The results of this example demonstrate that B cells expressing modified AID proteins yield altered hotspot usage.

EXAMPLE 14

This example describes the effects of transferring the Mut7.3 mutation to canine AID and human AID.

The function of AID in HEK293-c18 cells was measured by sequencing a co-expressed antibody template. Cells were cotransfected with three episomal vectors containing unique selection markers, one expressing an antibody heavy chain with puromycin selection, one expressing an antibody light chain with hygromycin selection, and one expressing AID with blasticidin selection. After transfection, cells were always cultured with puromycin and hygromycin but differentially treated with blasticidin. For cells "pulsed" with AID, no blasticidin was added to the culture and transient transfection of an AID vector was repeated each week of the experiment. For "stable" AID cells, blasticidin was added to the culture media, and for "stable+pulsed," cells were cultured with blasticidin in addition to transfection with an AID vector each week. Three different AID mutants were examined in these experiments: canine AID ("MutE"), canine AID containing Mut7.3 ("Mut 7.3 E"), and human AID containing Mut7.3 ("Human 7.3) (SEQ ID NOs: 88-93 and FIGS. 10a and 10b) and two different vector constructs were tested for AID expression (i.e., an IRES vector and a pEpi vector). With the IRES vector both AID and blasticidin expression were controlled by the same promoter with an IRES element between the genes. In the pEpi vectors, blasticidin expression was controlled by a separate promoter.

After approximately one month in culture, heavy chain variable regions were recovered by PCR for sequencing. Ninety-four templates were sequenced for each separate cell transfection experiment with an average of 88 complete sequences returned per experiment. The sequencing chromatograms were examined to verify the quality of the mutations observed and the frequency of mutation was calculated by dividing the number of mutations by the total number of nucleotides sequenced then dividing by the number of days in culture. The doubling time of HEK293-c18 cells is approximately 24 hours, so the days in culture was used to normalize the mutation rate per generation.

There was no significant difference in mutation frequency between the pulsed, stable, or stable+pulsed groups for each AID vector. In addition, there was no significant difference between IRES and pEpi vectors for MutE AID, nor any significant difference between Mut 7.3E and human 7.3. However, the difference in mutation frequency for Mut 7.3E in pEpi was statistically significant (p=0.0003) from Mut 7.3E in IRES.

This example demonstrates that Mut7.3 can be translated to canine AID and human AID.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid molecule comprising a nucleotide sequence encoding a functional mutant activation-induced cytidine deaminase (AID) protein variant the amino acid sequence of which differs from the amino acid sequence of a human AID protein of either SEQ ID NO:1 or SEQ ID NO:2 by amino acid substitutions at residue positions 10, 156, and 82 selected from the group consisting of K10E or K10D, E156G or E156A, and T82I or T82L, wherein the functional mutant AID protein has at least a 10-fold improvement in activity compared to the human AID protein in a bacterial papillation assay.

2. An expression vector comprising a nucleic acid molecule of claim 1.

3. An isolated eukaryotic cell comprising the vector of claim 2.

4. An isolated prokaryotic cell comprising the vector of claim 2.

5. An isolated or purified polypeptide comprising the amino acid sequence of SEQ ID NO: 33.

6. An isolated or purified polypeptide comprising the amino acid sequence of SEQ ID NO: 35.

7. An isolated or purified nucleic acid molecule wherein a nucleotide sequence encodes a functional mutant activation-induced cytidine deaminase (AID) protein variant of SEQ ID NO:1 or SEQ ID NO:2 wherein substitutions at the residue positions 10, 156, and 82 are selected from the group consisting of K10E or K10D, E156G or E156A, and T82I or T82L, and wherein one or more amino acid substitutions occur at residue positions selected from the group consisting of 9, 13, 15, 18, 30, 34, 35, 36, 38, 42, 43, 44, 53, 57, 59, 66, 74, 77, 81, 88, 93, 95, 96, 100, 104, 115, 118, 120, 132, 142, 145, 157, 160, 180, 181, 183, 184, 185, 188, 192, and 198 of SEQ ID NO:1 or SEQ ID NO:2.

8. The isolated or purified polynucleotide of claim 7, wherein amino acid substitutions at residue positions consisting of 9, 13, 15, 18, 30, 34, 35, 36, 38, 42, 43, 44, 53, 57, 59, 66, 74, 77, 81, 88, 93, 95, 96, 100, 104, 115, 118, 120, 132, 142, 145, 157, 160, 180, 181, 183, 184, 185, 188, 192, and 198 are selected from one or more of the following amino acid substitutions:

substitution at residue 9 by lysine (K), serine (S), methionine (M), or tryptophan (W),
substitution at residue 13 by phenylalanine (F) or tryptophan (W),
substitution at residue 15 by tyrosine (Y) or leucine (L),
substitution at residue 18 by alanine (A) or leucine (L),
substitution at residue 30 by tyrosine (Y) or serine (S),
substitution at residue 34 by glutamic acid (E) or aspartic acid (D),
substitution at residue 35 by serine (S) or lysine (K),
substitution at residue 36 by cysteine (C),
substitution at residue 38 by glycine (G) or alanine (A),
substitution at residue 42 by isoleucine (I) or leucine (L),
substitution at residue 43 by proline (P),
substitution at residue 44 by arginine (R) or lysine (K),
substitution at residue 53 by tyrosine (Y) or glutamine (Q),
substitution at residue 57 by alanine (A) or leucine (L),
substitution at residue 59 by methionine (M) or alanine (A),
substitution at residue 66 by threonine (T) or alanine (A),
substitution at residue 74 by histidine (H) or lysine (K),
substitution at residue 77 by serine (S) or lysine (K),
substitution at residue 81 by tyrosine (Y) or tryptophan (W),
substitution at residue 88 by serine (S) or threonine (T),
substitution at residue 93 by leucine (L), arginine (R), or lysine (K),
substitution at residue 95 by serine (S) or leucine (L),
substitution at residue 96 by glycine (G) or alanine (A),
substitution at residue 100 by glutamic acid (E), tryptophan (W), or phenylalanine (F),
substitution at residue 104 by isoleucine (I) or alanine (A),
substitution at residue 115 by tyrosine (Y) or leucine (L),
substitution at residue 118 by glutamic acid (E) or valine (V),
substitution at residue 120 by arginine (R) or leucine (L),
substitution at residue 132 by glutamic acid (E) or aspartic acid (D),
substitution at residue 142 by glutamic acid (E) or aspartic acid (D),
substitution at residue 145 by leucine (L) or tyrosine (Y),
substitution at residue 157 by isoleucine (I), glycine (G) or lysine (K),
substitution at residue 160 by glutamic acid (E) or aspartic acid (D),
substitution at residue 180 by isoleucine (I) or alanine (A),
substitution at residue 181 by methionine (M) or valine (V), 35
substitution at residue 183 by methionine (M) or valine (V),
substitution at residue 184 by asparagine (N) or glutamine (Q),
substitution at residue 185 by glycine (G) or aspartic acid (D),
substitution at residue 188 by glycine (G) or glutamic acid (E),
substitution at residue 192 by threonine (T) or serine (S), and
substitution at residue 198 by valine (V) or leucine (L).

9. The isolated or purified nucleic acid molecule of claim 7, which encodes a functional mutant activation-induced cytidine deaminase (AID) protein variant of SEQ ID NO:1 or SEQ ID NO:2 wherein amino acid substitutions at positions 10, 156, and 82, are selected from the group consisting of K10E or K10D, E156G or E156A, and T82I or T82L, and wherein one or more amino acid substitutions occur at residue positions selected from the group consisting of 9, 15, 18, 30, 34, 35, 36, 44, 53, 57, 59, 66, 74, 77, 88, 93, 100, 104, 115, 118, 120, 142, 145, 157, 160, 181, 184, 185, 188, and 192 of SEQ ID NO:1 or SEQ ID NO:2.

10. The isolated or purified nucleic acid molecule of claim 7, wherein amino acid substitutions at residue positions consisting of 9, 15, 18, 30, 34, 35, 36, 44, 53, 57, 59, 66, 74, 77, 88, 93, 100, 104, 115, 118, 120, 142, 145, 157, 160, 181, 184, 185, 188, and 192 are selected from one or more of the following amino acid substitutions:

substitution at residue 9 by serine (S), methionine (M), or tryptophan (W),
substitution at residue 15 by tyrosine (Y) or leucine (L),
substitution at residue 18 by alanine (A) or leucine (L),
substitution at residue 30 by tyrosine (Y) or serine (S),
substitution at residue 34 by glutamic acid (E) or aspartic acid (D),
substitution at residue 35 by serine (S) or lysine (K),
substitution at residue 36 by cysteine (C),
substitution at residue 44 by arginine (R) or lysine (K),
substitution at residue 53 by tyrosine (Y) or glutamine (Q),
substitution at residue 57 by alanine (A) or leucine (L),
substitution at residue 59 by methionine (M) or alanine (A),
substitution at residue 66 by threonine (T) or alanine (A),
substitution at residue 74 by histidine (H) or lysine (K),
substitution at residue 77 by serine (S) or lysine (K),
substitution at residue 88 by serine (S) or threonine (T),
substitution at residue 93 by leucine (L), arginine (R), or lysine (K),
substitution at residue 100 by glutamic acid (E), tryptophan (W), or phenylalanine (F),
substitution at residue 104 by isoleucine (I) or alanine (A),
substitution at residue 115 by tyrosine (Y) or leucine (L),
substitution at residue 118 by glutamic acid (E) or valine (V),
substitution at residue 120 by arginine (R) or leucine (L),
substitution at residue 142 by glutamic acid (E) or aspartic acid (D),
substitution at residue 145 by leucine (L) or tyrosine (Y),
substitution at residue 157 by isoleucine (I), glycine (G) or lysine (K),
substitution at residue 160 by glutamic acid (E) or aspartic acid (D),
substitution at residue 181 by methionine (M) or valine (V),
substitution at residue 184 by asparagine (N) or glutamine (Q),
substitution at residue 185 by glycine (G) or aspartic acid (D),
substitution at residue 188 by glycine (G) or glutamic acid (E), and
substitution at residue 192 by threonine (T) or serine (S).

11. The isolated or purified polynucleotide of claim 7, wherein a set of amino acid substitutions occurs at a one of the following sets of residue positions:

the set of positions 9, 36, 44, 88, 93, and 142,
the set of positions 66, 104, 160, and 181,
the set of positions 15, 115, and 185,
the set of positions 9, 30, 34, 100, and 184,
the set of positions 34, 35, 59, 120, and 157,
the set of positions 9, 74, 77, 118, 157, and 188,
the set of positions 53 and 145,
the set of positions 18, 93, 100, 160, and 192, or
the position 57.

12. The isolated or purified polynucleotide of claim 7 wherein the encoded amino acid substitutions in the functional mutant activation-induced cytidine deaminase (AID) protein consist of the substitutions K10E, E156G, T82I, S66T, L104I, and K160E.

13. An expression vector comprising a nucleic acid molecule of claim 7.

14. An isolated eukaryotic cell comprising the vector of claim 13.

15. An isolated prokaryotic cell comprising the vector of claim 13.

16. A method for preparing a gene product having a desired property, which method comprises expressing a nucleic acid encoding the gene product in a population of cells, wherein the population of cells expresses, or is induced to express, a functional mutant activation-induced cytidine deaminase (AID) protein encoded by the nucleic acid molecule of claim 1, whereupon expression of the functional mutant AID protein induces a mutation in the nucleic acid encoding the gene product.

17. The method of claim 16, wherein the method further comprises the step of selecting a cell or cells within the population which expresses the mutated nucleic acid sequence encoding the gene product having the desired property.

18. The method of claim 16, wherein the cell is a eukaryotic cell or a prokaryotic cell.

19. The method of claim 16, wherein the cell is a mammalian cell.

20. The method of claim 16, wherein the cell is a B cell or B cell derivative.

21. The method of claim 16, wherein the cell comprises at least one nucleic acid sequence that has been codon optimized for somatic hypermutation (SHM) to increase the number of SHM motifs.

\* \* \* \* \*

SEQUENCE LISTING

```
<160> NUMBER OF SEQ ID NOS: 93

<210> SEQ ID NO 1
<211> LENGTH: 198
<212> TYPE: PRT
<213> ORGANISM: Homo sapiens

<400> SEQUENCE: 1

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30
```

```
Val Lys Arg Arg Asp Ser Ala Thr Ser Phe Ser Leu Asp Phe Gly Tyr
         35                  40                  45

Leu Arg Asn Lys Asn Gly Cys His Val Glu Leu Leu Phe Leu Arg Tyr
 50                  55                  60

Ile Ser Asp Trp Asp Leu Asp Pro Gly Arg Cys Tyr Arg Val Thr Trp
 65                  70                  75                  80

Phe Thr Ser Arg Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
            130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 2
<211> LENGTH: 198
<212> TYPE: PRT
<213> ORGANISM: Homo sapiens

<400> SEQUENCE: 2

Met Asp Ser Leu Leu Met Asn Arg Arg Lys Phe Leu Tyr Gln Phe Lys
  1               5                  10                  15

Asn Val Arg Trp Ala Lys Gly Arg Arg Glu Thr Tyr Leu Cys Tyr Val
                 20                  25                  30

Val Lys Arg Arg Asp Ser Ala Thr Ser Phe Ser Leu Asp Phe Gly Tyr
         35                  40                  45

Leu Arg Asn Lys Asn Gly Cys His Val Glu Leu Leu Phe Leu Arg Tyr
 50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
            130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195
```

<210> SEQ ID NO 3
<211> LENGTH: 198
<212> TYPE: PRT
<213> ORGANISM: Canis lupus

<400> SEQUENCE: 3

```
Met Asp Ser Leu Leu Met Lys Gln Arg Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Ala Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Lys Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 4
<211> LENGTH: 198
<212> TYPE: PRT
<213> ORGANISM: Mus musculus

<400> SEQUENCE: 4

```
Met Asp Ser Leu Leu Met Lys Gln Lys Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Cys Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Glu
                85                  90                  95

Phe Leu Arg Trp Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125
```

```
Leu His Arg Ala Gly Val Gln Ile Gly Ile Met Thr Phe Lys Asp Tyr
    130                 135                 140

Phe Tyr Cys Trp Asn Thr Phe Val Glu Asn Arg Glu Arg Thr Phe Lys
145                 150                 155                 160

Ala Trp Glu Gly Leu His Glu Asn Ser Val Arg Leu Thr Arg Gln Leu
                165                 170                 175

Arg Arg Ile Leu Leu Pro Leu Tyr Glu Val Asp Asp Leu Arg Asp Ala
            180                 185                 190

Phe Arg Met Leu Gly Phe
        195

<210> SEQ ID NO 5
<211> LENGTH: 198
<212> TYPE: PRT
<213> ORGANISM: Rattus norvegicus

<400> SEQUENCE: 5

Met Asp Ser Leu Leu Met Lys Gln Lys Lys Phe Leu Tyr His Phe Lys
1               5                   10                  15

Asn Val Arg Trp Ala Lys Gly Arg His Glu Thr Tyr Leu Cys Tyr Val
                20                  25                  30

Val Lys Arg Arg Asp Ser Ala Thr Ser Phe Ser Leu Asp Phe Gly His
            35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Glu
                85                  90                  95

Phe Leu Arg Trp Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Gly Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Thr Arg Gln Leu
                165                 170                 175

Arg Arg Ile Leu Leu Pro Leu Tyr Glu Val Asp Asp Leu Arg Asp Ala
            180                 185                 190

Phe Arg Ile Leu Gly Leu
        195

<210> SEQ ID NO 6
<211> LENGTH: 199
<212> TYPE: PRT
<213> ORGANISM: Bos taurus

<400> SEQUENCE: 6

Met Asp Ser Leu Leu Lys Lys Gln Arg Gln Phe Leu Tyr Gln Phe Lys
1               5                   10                  15

Asn Val Arg Trp Ala Lys Gly Arg His Glu Thr Tyr Leu Cys Tyr Val
                20                  25                  30

Val Lys Arg Arg Asp Ser Pro Thr Ser Phe Ser Leu Asp Phe Gly His
            35                  40                  45
```

```
Leu Arg Asn Lys Ala Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Tyr Pro Asn Leu Ser Leu Arg Ile Phe Thr Ala Arg
                100                 105                 110

Leu Tyr Phe Cys Asp Lys Glu Arg Lys Ala Glu Pro Glu Gly Leu Arg
            115                 120                 125

Arg Leu His Arg Ala Gly Val Gln Ile Ala Ile Met Thr Phe Lys Asp
        130                 135                 140

Tyr Phe Tyr Cys Trp Asn Thr Phe Val Glu Asn His Glu Arg Thr Phe
145                 150                 155                 160

Lys Ala Trp Glu Gly Leu His Glu Asn Ser Val Arg Leu Ser Arg Gln
                165                 170                 175

Leu Arg Arg Ile Leu Leu Pro Leu Tyr Glu Val Asp Asp Leu Arg Asp
                180                 185                 190

Ala Phe Arg Thr Leu Gly Leu
            195

<210> SEQ ID NO 7
<211> LENGTH: 198
<212> TYPE: PRT
<213> ORGANISM: Gallus gallus

<400> SEQUENCE: 7

Met Asp Ser Leu Leu Met Lys Arg Lys Leu Phe Leu Tyr Asn Phe Lys
  1               5                  10                  15

Asn Leu Arg Trp Ala Lys Gly Arg Arg Glu Thr Tyr Leu Cys Tyr Val
                 20                  25                  30

Val Lys Arg Arg Asp Ser Ala Thr Ser Cys Ser Leu Asp Phe Gly Tyr
             35                  40                  45

Leu Arg Asn Lys Met Gly Cys His Val Glu Val Leu Phe Leu Arg Tyr
        50                  55                  60

Ile Ser Ala Trp Asp Leu Asp Pro Gly Arg Cys Tyr Arg Ile Thr Trp
 65                  70                  75                  80

Phe Thr Ser Trp Ser Pro Cys Tyr Asp Cys Ala Arg His Val Ala Asp
                 85                  90                  95

Phe Leu Arg Ala Tyr Pro Asn Leu Thr Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Ala Gln Ile Ala Ile Met Thr Phe Lys Asp Phe
        130                 135                 140

Phe Tyr Cys Trp Asn Thr Phe Val Glu Asn Arg Glu Lys Thr Phe Lys
145                 150                 155                 160

Ala Trp Glu Gly Leu His Glu Asn Ser Val His Leu Ser Arg Lys Leu
                165                 170                 175

Arg Arg Ile Leu Leu Pro Leu Tyr Glu Val Asp Asp Leu Arg Asp Ala
                180                 185                 190

Phe Lys Thr Leu Gly Leu
            195
```

```
<210> SEQ ID NO 8
<211> LENGTH: 198
<212> TYPE: PRT
<213> ORGANISM: Sus scrofa

<400> SEQUENCE: 8

Met Asp Ser Leu Leu Met Lys Gln Arg Gln Phe Leu Tyr Gln Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asn
                85                  90                  95

Phe Leu Arg Gly Asn Pro Asn Leu Ser Leu Arg Ile Phe Thr Ala Arg
            100                 105                 110

Leu Tyr Phe Cys Asp Gly Tyr Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Arg Ser Phe Lys
145                 150                 155                 160

Ala Trp Glu Gly Leu His Glu Asn Ser Val Arg Leu Thr Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 9
<211> LENGTH: 198
<212> TYPE: PRT
<213> ORGANISM: Pan troglodytes

<400> SEQUENCE: 9

Met Asp Ser Leu Leu Met Asn Arg Lys Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
```

```
            130                 135                 140
Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 10
<211> LENGTH: 198
<212> TYPE: PRT
<213> ORGANISM: Macaca mulatta

<400> SEQUENCE: 10

Met Asp Ser Leu Leu Met Asn Arg Arg Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 11
<211> LENGTH: 239
<212> TYPE: PRT
<213> ORGANISM: Equus cabullus

<400> SEQUENCE: 11

Met Ser Glu Val Leu Thr Thr Arg Pro Ala Val Pro Asp Ala Val Pro
1               5                   10                  15

Pro Val Pro Asn Leu Leu Ile His Thr Ala Gln Glu Glu Asn Asp Leu
            20                  25                  30

Cys Ser Phe Ile Phe Leu Pro Pro Leu Ile His Ser Leu Leu Met Lys
        35                  40                  45

Gln Arg Lys Phe Leu Tyr His Phe Lys Asn Val Arg Trp Ala Lys Gly
```

```
            50                  55                  60
Arg His Glu Thr Tyr Leu Cys Tyr Val Val Lys Arg Arg Asp Ser Ala
 65                  70                  75                  80

Thr Ser Phe Ser Leu Asp Phe Gly His Leu Arg Asn Lys Ser Gly Cys
                     85                  90                  95

His Val Glu Leu Leu Phe Leu Arg Tyr Ile Ser Asp Trp Asp Leu Asp
                100                 105                 110

Pro Gly Arg Cys Tyr Arg Val Thr Trp Phe Thr Ser Trp Ser Pro Cys
                115                 120                 125

Tyr Asp Cys Ala Arg His Val Ala Asp Phe Leu Arg Gly Tyr Pro Asn
130                 135                 140

Leu Ser Leu Arg Ile Phe Ala Ala Arg Leu Tyr Phe Cys Glu Asp Arg
145                 150                 155                 160

Lys Ala Glu Pro Glu Gly Leu Arg Arg Leu His Arg Ala Gly Val Gln
                165                 170                 175

Ile Ala Ile Met Thr Phe Lys Asp Tyr Phe Tyr Cys Trp Asn Thr Phe
                180                 185                 190

Val Glu Asn Arg Glu Arg Thr Phe Lys Ala Trp Glu Gly Leu His Glu
                195                 200                 205

Asn Ser Val Arg Leu Ser Arg Gln Leu Arg Arg Ile Leu Leu Pro Leu
210                 215                 220

Tyr Glu Val Asp Asp Leu Arg Asp Ala Phe Arg Thr Leu Gly Leu
225                 230                 235

<210> SEQ ID NO 12
<211> LENGTH: 201
<212> TYPE: PRT
<213> ORGANISM: Xenopus sp.

<400> SEQUENCE: 12

Met Thr Met Asp Ser Met Leu Leu Lys Arg Asn Lys Phe Ile Tyr His
 1               5                  10                  15

Tyr Lys Asn Leu Arg Trp Ala Arg Gly Arg His Glu Thr Tyr Leu Cys
                 20                  25                  30

Tyr Ile Val Lys Arg Arg Tyr Ser Ser Val Ser Cys Ala Leu Asp Phe
             35                  40                  45

Gly Tyr Leu Arg Asn Arg Asn Gly Cys His Ala Glu Met Leu Phe Leu
 50                  55                  60

Arg Tyr Leu Ser Ile Trp Val Gly His Asp Pro His Arg Asn Tyr Arg
 65                  70                  75                  80

Val Thr Trp Phe Ser Ser Trp Ser Pro Cys Tyr Asp Cys Ala Lys Arg
                 85                  90                  95

Thr Leu Glu Phe Leu Lys Gly His Pro Asn Phe Ser Leu Arg Ile Phe
                100                 105                 110

Ser Ala Arg Leu Tyr Phe Cys Glu Glu Arg Asn Ala Glu Pro Glu Gly
             115                 120                 125

Leu Arg Lys Leu Gln Lys Ala Gly Val Arg Leu Ser Val Met Ser Tyr
130                 135                 140

Lys Asp Tyr Phe Tyr Cys Trp Asn Thr Phe Val Glu Thr Arg Glu Ser
145                 150                 155                 160

Gly Phe Glu Ala Trp Asp Gly Leu His Glu Asn Ser Val Arg Leu Ala
                165                 170                 175

Arg Lys Leu Arg Arg Ile Leu Gln Pro Pro Tyr Asp Met Glu Asp Leu
                180                 185                 190
```

Arg Glu Val Phe Val Leu Leu Gly Leu
        195                 200

<210> SEQ ID NO 13
<211> LENGTH: 204
<212> TYPE: PRT
<213> ORGANISM: Takifugu rubripes

<400> SEQUENCE: 13

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
        35                  40                  45

Arg Ser Gly Cys His Val Glu Leu Leu Phe Leu Arg Tyr Leu Gly Ala
    50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asp Ser Leu
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala Trp Asp Leu
            180                 185                 190

Glu Asp Leu Arg Asp Ala Leu Lys Leu Leu Gly Phe
        195                 200

<210> SEQ ID NO 14
<211> LENGTH: 210
<212> TYPE: PRT
<213> ORGANISM: Danio rerio

<400> SEQUENCE: 14

Met Ile Cys Lys Leu Asp Ser Val Leu Met Thr Gln Lys Lys Phe Ile
1               5                   10                  15

Phe His Tyr Lys Asn Val Arg Trp Ala Arg Gly Arg His Glu Thr Tyr
            20                  25                  30

Leu Cys Phe Val Val Lys Arg Arg Ile Gly Pro Asp Ser Leu Ser Phe
        35                  40                  45

Asp Phe Gly His Leu Arg Asn Arg Ser Gly Cys His Val Glu Leu Leu
    50                  55                  60

Phe Leu Arg His Leu Gly Ala Leu Cys Pro Gly Leu Ser Ala Ser Ser
65                  70                  75                  80

Val Asp Gly Ala Arg Leu Cys Tyr Ser Val Thr Trp Phe Cys Ser Trp
                85                  90                  95

Ser Pro Cys Ser Lys Cys Ala Gln Gln Leu Ala His Phe Leu Ser Gln
            100                 105                 110

```
Thr Pro Asn Leu Arg Leu Arg Ile Phe Val Ser Arg Leu Tyr Phe Cys
        115                 120                 125

Asp Glu Glu Asp Ser Val Glu Arg Gly Leu Arg His Leu Lys Arg
130                 135                 140

Ala Gly Val Gln Ile Ser Val Met Thr Tyr Lys Asp Phe Phe Tyr Cys
145                 150                 155                 160

Trp Gln Thr Phe Val Ala Arg Arg Glu Arg Ser Phe Lys Ala Trp Asp
            165                 170                 175

Gly Leu His Glu Asn Ser Val Arg Leu Val Arg Lys Leu Asn Arg Ile
            180                 185                 190

Leu Gln Pro Cys Glu Thr Glu Asp Leu Arg Asp Val Phe Ala Leu Leu
            195                 200                 205

Gly Leu
    210

<210> SEQ ID NO 15
<211> LENGTH: 198
<212> TYPE: PRT
<213> ORGANISM: Artificial Sequence
<220> FEATURE:
<223> OTHER INFORMATION: AID mutant Mut1

<400> SEQUENCE: 15

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
            85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
            165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 16
<211> LENGTH: 198
<212> TYPE: PRT
<213> ORGANISM: Artificial Sequence
<220> FEATURE:
<223> OTHER INFORMATION: AID mutant Mut1.1

<400> SEQUENCE: 16
```

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Glu Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Thr Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 17
<211> LENGTH: 198
<212> TYPE: PRT
<213> ORGANISM: Artificial Sequence
<220> FEATURE:
<223> OTHER INFORMATION: AID mutant Mut1.1.1

<400> SEQUENCE: 17

Met Asp Ser Leu Leu Met Asn Arg Met Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Glu Arg Arg Asp Gly Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Thr Thr Phe Lys
145                 150                 155                 160

```
Ala Trp Glu Gly Leu His Glu Asn Ser Val Arg Leu Ser Arg Gln Leu
                165                 170                 175

Arg Arg Ile Ile Leu Pro Leu Tyr Glu Val Asp Asp Leu Arg Asp Ala
            180                 185                 190

Phe Arg Thr Leu Gly Leu
        195

<210> SEQ ID NO 18
<211> LENGTH: 198
<212> TYPE: PRT
<213> ORGANISM: Artificial Sequence
<220> FEATURE:
<223> OTHER INFORMATION: AID mutant Mut1.1.2

<400> SEQUENCE: 18

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Ile Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Tyr Cys Glu Asp Arg Lys Ala Glu Pro Glu Gly Leu Arg Arg
        115                 120                 125

Leu His Arg Asp Gly Val Gln Ile Ala Ile Met Thr Phe Lys Asp Tyr
    130                 135                 140

Phe Tyr Cys Trp Asn Thr Phe Val Glu Asn His Gly Thr Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Pro Tyr Glu Val Asp Asp Leu Arg Asp Ala
            180                 185                 190

Phe Arg Thr Leu Gly Val
        195

<210> SEQ ID NO 19
<211> LENGTH: 198
<212> TYPE: PRT
<213> ORGANISM: Artificial Sequence
<220> FEATURE:
<223> OTHER INFORMATION: AID mutant Mut1.1.3

<400> SEQUENCE: 19

Met Asp Ser Leu Leu Met Asn Arg Lys Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
```

```
                    50                  55                  60
Ile Ser Asp Trp Asp Leu Asp Pro Gly Arg Cys Tyr Arg Val Thr Trp
 65                  70                  75                  80

Phe Thr Ser Arg Ser Pro Cys Tyr Asp Cys Ala Arg His Val Ala Gly
                 85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
            130                 135                 140

Phe Tyr Cys Trp Asn Thr Phe Val Glu Asn His Gly Thr Thr Phe Lys
145                 150                 155                 160

Ala Trp Glu Gly Leu His Glu Asn Ser Val Arg Leu Ser Arg Gln Leu
                165                 170                 175

Arg Arg Ile Leu Met Pro Leu Tyr Glu Val Asp Asp Leu Arg Asp Ala
            180                 185                 190

Phe Arg Thr Leu Gly Leu
            195

<210> SEQ ID NO 20
<211> LENGTH: 198
<212> TYPE: PRT
<213> ORGANISM: Artificial Sequence
<220> FEATURE:
<223> OTHER INFORMATION: AID mutant Mut1.1.4

<400> SEQUENCE: 20

Met Asp Ser Leu Leu Met Asn Arg Arg Lys Phe Leu Phe Gln Phe Lys
 1               5                  10                  15

Asn Val Arg Trp Ala Lys Gly Arg Arg Glu Thr Tyr Leu Cys Tyr Val
                20                  25                  30

Val Glu Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
 50                  55                  60

Ile Ser Asp Trp Asp Leu Asp Pro Gly Arg Cys Tyr Arg Val Thr Trp
 65                  70                  75                  80

Phe Thr Ser Arg Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
            130                 135                 140

Phe Tyr Cys Trp Asn Thr Phe Val Glu Asn His Gly Thr Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Arg Leu
            195
```

```
<210> SEQ ID NO 21
<211> LENGTH: 198
<212> TYPE: PRT
<213> ORGANISM: Artificial Sequence
<220> FEATURE:
<223> OTHER INFORMATION: AID mutant Mut1.2

<400> SEQUENCE: 21

Met Asp Ser Leu Leu Met Asn Arg Arg Lys Phe Leu Tyr Gln Phe Lys
1               5                   10                  15

Asn Val Arg Trp Ala Lys Gly Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Ile Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 22
<211> LENGTH: 189
<212> TYPE: PRT
<213> ORGANISM: Artificial Sequence
<220> FEATURE:
<223> OTHER INFORMATION: AID mutant Mut1.3

<400> SEQUENCE: 22

Met Asp Ser Leu Leu Met Asn Arg Arg Lys Phe Leu Tyr Gln Phe Lys
1               5                   10                  15

Asn Val Arg Trp Ala Lys Gly Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110
```

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Gly Lys Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu
            180                 185

<210> SEQ ID NO 23
<211> LENGTH: 198
<212> TYPE: PRT
<213> ORGANISM: Artificial Sequence
<220> FEATURE:
<223> OTHER INFORMATION: AID mutant Mut1.4

<400> SEQUENCE: 23

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 24
<211> LENGTH: 189
<212> TYPE: PRT
<213> ORGANISM: Artificial Sequence
<220> FEATURE:
<223> OTHER INFORMATION: AID mutant Mut1.5

<400> SEQUENCE: 24

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

```
Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu
                180                 185

<210> SEQ ID NO 25
<211> LENGTH: 198
<212> TYPE: PRT
<213> ORGANISM: Artificial Sequence
<220> FEATURE:
<223> OTHER INFORMATION: AID mutant Mut2

<400> SEQUENCE: 25

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
                180                 185                 190

Phe Arg Thr Leu Gly Leu
                195
```

<210> SEQ ID NO 26
<211> LENGTH: 198
<212> TYPE: PRT
<213> ORGANISM: Artificial Sequence
<220> FEATURE:
<223> OTHER INFORMATION: AID mutant Mut3

<400> SEQUENCE: 26

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Ile Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 27
<211> LENGTH: 198
<212> TYPE: PRT
<213> ORGANISM: Artificial Sequence
<220> FEATURE:
<223> OTHER INFORMATION: AID mutant Mut4

<400> SEQUENCE: 27

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Gly Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
```

```
                     100                 105                 110
Leu Tyr Phe Cys Glu Arg Lys Ala Glu Pro Glu Gly Leu Arg Arg
        115                 120                 125

Leu His Arg Ala Gly Val Gln Ile Ala Ile Met Thr Phe Lys Asp Tyr
        130                 135                 140

Leu Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                    165                 170                 175

Arg Arg Ile Leu Leu Pro Leu Tyr Glu Val Asp Asp Leu Arg Asp Ala
                180                 185                 190

Phe Arg Thr Leu Gly Leu
            195

<210> SEQ ID NO 28
<211> LENGTH: 183
<212> TYPE: PRT
<213> ORGANISM: Artificial Sequence
<220> FEATURE:
<223> OTHER INFORMATION: AID mutant Mut5

<400> SEQUENCE: 28

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                    165                 170                 175

Arg Arg Ile Leu Leu Pro Leu
                180

<210> SEQ ID NO 29
<211> LENGTH: 198
<212> TYPE: PRT
<213> ORGANISM: Artificial Sequence
<220> FEATURE:
<223> OTHER INFORMATION: AID mutant Mut6

<400> SEQUENCE: 29

Met Asp Ser Leu Leu Met Asn Arg Arg Glu Phe Leu Tyr Gln Phe Lys
1               5                   10                  15
```

```
Asn Val Arg Trp Ala Lys Gly Arg Arg Glu Thr Tyr Leu Cys Tyr Val
             20                  25                  30

Val Lys Arg Arg Asp Ser Ala Thr Ser Phe Ser Leu Asp Phe Gly Tyr
         35                  40                  45

Leu Arg Asn Lys Asn Gly Cys His Val Glu Leu Leu Phe Leu Arg Tyr
     50                  55                  60

Ile Ser Asp Trp Asp Leu Asp Pro Gly Arg Cys Tyr Arg Val Thr Trp
 65                  70                  75                  80

Phe Thr Ser Arg Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Pro Tyr Glu Val Asp Asp Leu Arg Asp Ala
            180                 185                 190

Phe Arg Thr Leu Gly Leu
            195

<210> SEQ ID NO 30
<211> LENGTH: 198
<212> TYPE: PRT
<213> ORGANISM: Artificial Sequence
<220> FEATURE:
<223> OTHER INFORMATION: AID mutant Mut7

<400> SEQUENCE: 30

Met Asp Ser Leu Leu Met Asn Arg Arg Glu Phe Leu Tyr Gln Phe Lys
 1               5                  10                  15

Asn Val Arg Trp Ala Lys Gly Arg Arg Glu Thr Tyr Leu Cys Tyr Val
             20                  25                  30

Val Lys Arg Arg Asp Ser Ala Thr Ser Phe Ser Leu Asp Phe Gly Tyr
         35                  40                  45

Leu Arg Asn Lys Asn Gly Cys His Val Glu Leu Leu Phe Leu Arg Tyr
     50                  55                  60

Ile Ser Asp Trp Asp Leu Asp Pro Gly Arg Cys Tyr Arg Val Thr Trp
 65                  70                  75                  80

Phe Thr Ser Arg Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175
```

```
Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 31
<211> LENGTH: 198
<212> TYPE: PRT
<213> ORGANISM: Artificial Sequence
<220> FEATURE:
<223> OTHER INFORMATION: AID mutant Mut7.1

<400> SEQUENCE: 31

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Tyr Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 32
<211> LENGTH: 198
<212> TYPE: PRT
<213> ORGANISM: Artificial Sequence
<220> FEATURE:
<223> OTHER INFORMATION: AID mutant Mut7.2

<400> SEQUENCE: 32

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80
```

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 33
<211> LENGTH: 198
<212> TYPE: PRT
<213> ORGANISM: Artificial Sequence
<220> FEATURE:
<223> OTHER INFORMATION: AID mutant Mut7.3

<400> SEQUENCE: 33

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Ile Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 34
<211> LENGTH: 198
<212> TYPE: PRT
<213> ORGANISM: Artificial Sequence
<220> FEATURE:
<223> OTHER INFORMATION: AID mutant Mut7.3.1

<400> SEQUENCE: 34

Met Asp Ser Leu Leu Met Asn Arg Ser Glu Phe Leu Tyr Gln Phe Lys
1               5                   10                  15

Asn Val Arg Trp Ala Lys Gly Arg Glu Thr Tyr Leu Cys Tyr Val
            20                  25                  30

Val Lys Arg Cys Asp Ser Ala Thr Ser Phe Ser Arg Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Ile Ser Arg Ser Pro Cys Ser Asp Cys Ala Arg Leu Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Glu Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 35
<211> LENGTH: 180
<212> TYPE: PRT
<213> ORGANISM: Artificial Sequence
<220> FEATURE:
<223> OTHER INFORMATION: AID mutant Mut7.3.2

<400> SEQUENCE: 35

Met Asp Ser Leu Leu Met Asn Arg Arg Glu Phe Leu Tyr Gln Phe Lys
1               5                   10                  15

Asn Val Arg Trp Ala Lys Gly Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Thr Asp Trp Asp Leu Asp Pro Gly Arg Cys Tyr Arg Val Thr Trp
65                  70                  75                  80

Phe Ile Ser Arg Ser Pro Cys Tyr Asp Cys Ala Arg His Val Ala Asp
                85                  90                  95

Phe Leu Arg Gly Asn Pro Asn Ile Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr

-continued

```
                130                 135                 140
Phe Tyr Cys Trp Asn Thr Phe Val Glu Asn His Gly Arg Thr Phe Glu
145                 150                 155                 160

Ala Trp Glu Gly Leu His Glu Asn Ser Val Arg Leu Ser Arg Gln Leu
                165                 170                 175

Arg Arg Ile Leu
            180

<210> SEQ ID NO 36
<211> LENGTH: 198
<212> TYPE: PRT
<213> ORGANISM: Artificial Sequence
<220> FEATURE:
<223> OTHER INFORMATION: AID mutant Mut7.3.3

<400> SEQUENCE: 36

Met Asp Ser Leu Leu Met Asn Arg Arg Glu Phe Leu Tyr Gln Tyr Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
50                  55                  60

Ile Ser Asp Trp Asp Leu Asp Pro Gly Arg Cys Tyr Arg Val Thr Trp
65                  70                  75                  80

Phe Ile Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Tyr Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Gly Val Asp Asp Leu Arg Asp Ala
            180                 185                 190

Phe Arg Thr Leu Gly Leu
        195

<210> SEQ ID NO 37
<211> LENGTH: 198
<212> TYPE: PRT
<213> ORGANISM: Artificial Sequence
<220> FEATURE:
<223> OTHER INFORMATION: AID mutant Mut7.3.4

<400> SEQUENCE: 37

Met Asp Ser Leu Leu Met Asn Arg Trp Glu Phe Leu Tyr Gln Phe Lys
1               5                   10                  15

Asn Val Arg Trp Ala Lys Gly Arg Arg Glu Thr Tyr Leu Tyr Tyr Val
                20                  25                  30

Val Glu Arg Arg Asp Ser Ala Thr Ser Phe Ser Leu Asp Phe Gly Tyr
            35                  40                  45
```

```
Leu Arg Asn Lys Asn Gly Cys His Val Glu Leu Leu Phe Leu Arg Tyr
 50                  55                  60

Ile Ser Asp Trp Asp Leu Asp Pro Gly Arg Cys Tyr Arg Val Thr Trp
 65              70                  75                  80

Phe Ile Ser Arg Ser Pro Cys Tyr Asp Cys Ala Arg His Val Ala Asp
                 85                  90                  95

Phe Leu Arg Trp Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
                115                 120                 125

Leu His Arg Ala Gly Val Gln Ile Ala Ile Met Thr Phe Lys Asp Tyr
                130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                    165                 170                 175

Arg Arg Ile Leu Leu Pro Leu Asn Glu Val Asp Asp Leu Arg Asp Ala
                180                 185                 190

Phe Arg Thr Leu Gly Leu
                195

<210> SEQ ID NO 38
<211> LENGTH: 198
<212> TYPE: PRT
<213> ORGANISM: Artificial Sequence
<220> FEATURE:
<223> OTHER INFORMATION: AID mutant Mut7.3.5

<400> SEQUENCE: 38

Met Asp Ser Leu Leu Met Asn Arg Arg Glu Phe Leu Tyr Gln Phe Lys
 1               5                  10                  15

Asn Val Arg Trp Ala Lys Gly Arg Arg Glu Thr Tyr Leu Cys Tyr Val
                 20                  25                  30

Val Glu Ser Arg Asp Ser Ala Thr Ser Phe Ser Leu Asp Phe Gly Tyr
                 35                  40                  45

Leu Arg Asn Lys Asn Gly Cys His Val Glu Met Leu Phe Leu Arg Tyr
 50                  55                  60

Ile Ser Asp Trp Asp Leu Asp Pro Gly Arg Cys Tyr Arg Val Thr Trp
 65              70                  75                  80

Phe Ile Ser Arg Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
                100                 105                 110

Leu Tyr Phe Cys Glu Asp Arg Arg Ala Glu Pro Glu Gly Leu Arg Arg
                115                 120                 125

Leu His Arg Ala Gly Val Gln Ile Ala Ile Met Thr Phe Lys Asp Tyr
                130                 135                 140

Phe Tyr Cys Trp Asn Thr Phe Val Glu Asn His Gly Ile Thr Phe Lys
145                 150                 155                 160

Ala Trp Glu Gly Leu His Glu Asn Ser Val Arg Leu Ser Arg Gln Leu
                    165                 170                 175

Arg Arg Ile Leu Leu Pro Leu Tyr Glu Val Asp Asp Leu Arg Asp Ala
                180                 185                 190

Phe Arg Thr Leu Gly Leu
                195
```

<210> SEQ ID NO 39
<211> LENGTH: 198
<212> TYPE: PRT
<213> ORGANISM: Artificial Sequence
<220> FEATURE:
<223> OTHER INFORMATION: AID mutant Mut7.3.6

<400> SEQUENCE: 39

```
Met Asp Ser Leu Leu Met Asn Arg Ser Glu Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly His Cys Tyr Ser Val Thr Trp
65                  70                  75                  80

Phe Ile Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Val Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Gly Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Gly Leu Arg Asp Ala
            180                 185                 190

Phe Arg Thr Leu Gly Leu
        195
```

<210> SEQ ID NO 40
<211> LENGTH: 198
<212> TYPE: PRT
<213> ORGANISM: Artificial Sequence
<220> FEATURE:
<223> OTHER INFORMATION: AID mutant Mut7.3.7

<400> SEQUENCE: 40

```
Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Tyr Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Ile Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110
```

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Leu Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 41
<211> LENGTH: 198
<212> TYPE: PRT
<213> ORGANISM: Artificial Sequence
<220> FEATURE:
<223> OTHER INFORMATION: AID mutant Mut7.3.8

<400> SEQUENCE: 41

Met Asp Ser Leu Leu Met Asn Arg Arg Glu Phe Leu Tyr Gln Phe Lys
1               5                   10                  15

Asn Ala Arg Trp Ala Lys Gly Arg Glu Thr Tyr Leu Cys Tyr Val Val
            20                  25                  30

Lys Arg Arg Asp Ser Ala Thr Ser Phe Ser Leu Asp Phe Gly Tyr Leu
        35                  40                  45

Arg Asn Lys Asn Gly Cys His Val Glu Leu Leu Phe Leu Arg Tyr Ile
    50                  55                  60

Ser Asp Trp Asp Leu Asp Pro Gly Arg Cys Tyr Arg Val Thr Trp Phe
65                  70                  75                  80

Ile Ser Arg Ser Pro Cys Tyr Asp Cys Ala Arg Arg Val Ala Asp Phe
                85                  90                  95

Leu Arg Glu Asn Pro Asn Leu Ser Leu Arg Ile Phe Thr Ala Arg Leu
            100                 105                 110

Tyr Phe Cys Glu Asp Arg Lys Ala Glu Pro Glu Gly Leu Arg Arg Leu
        115                 120                 125

His Arg Ala Gly Val Gln Ile Ala Ile Met Thr Phe Lys Asp Tyr Phe
    130                 135                 140

Tyr Cys Trp Asn Thr Phe Val Glu Asn His Gly Arg Thr Phe Glu Ala
145                 150                 155                 160

Trp Glu Gly Leu His Glu Asn Ser Val Arg Leu Ser Arg Gln Leu Arg
                165                 170                 175

Arg Ile Leu Leu Pro Leu Tyr Glu Val Asp Asp Leu Arg Asp Thr Phe
            180                 185                 190

Arg Thr Leu Gly Leu
        195

<210> SEQ ID NO 42
<211> LENGTH: 198
<212> TYPE: PRT
<213> ORGANISM: Artificial Sequence
<220> FEATURE:
<223> OTHER INFORMATION: AID mutant Mut7.3.9

<400> SEQUENCE: 42

Met Asp Ser Leu Leu Met Asn Arg Arg Glu Phe Leu Tyr Gln Phe Lys

```
   1               5                  10                 15
Asn Val Arg Trp Ala Lys Gly Arg Arg Glu Thr Tyr Leu Cys Tyr Val
                20                 25                 30

Val Lys Arg Arg Asp Ser Ala Thr Ser Phe Ser Leu Asp Phe Gly Tyr
            35                 40                 45

Leu Arg Asn Lys Asn Gly Cys His Ala Glu Leu Leu Phe Leu Arg Tyr
        50                 55                 60

Ile Ser Asp Trp Asp Leu Asp Pro Gly Arg Cys Tyr Arg Val Thr Trp
 65                 70                 75                 80

Phe Ile Ser Arg Ser Pro Cys Tyr Asp Cys Ala Arg His Val Ala Asp
                85                 90                 95

Phe Leu Arg Gly Asn Pro Asn Leu Ser Leu Arg Ile Phe Thr Ala Arg
            100                105                110

Leu Tyr Phe Cys Glu Asp Arg Lys Ala Glu Pro Glu Gly Leu Arg Arg
        115                120                125

Leu His Arg Ala Gly Val Gln Ile Ala Ile Met Thr Phe Lys Asp Tyr
    130                135                140

Phe Tyr Cys Trp Asn Thr Phe Val Glu Asn His Gly Arg Thr Phe Lys
145                150                155                160

Ala Trp Glu Gly Leu His Glu Asn Ser Val Arg Leu Ser Arg Gln Leu
                165                170                175

Arg Arg Ile Leu Leu Pro Leu Tyr Glu Val Asp Asp Leu Arg Asp Ala
            180                185                190

Phe Arg Thr Leu Gly Leu
            195
```

<210> SEQ ID NO 43
<211> LENGTH: 198
<212> TYPE: PRT
<213> ORGANISM: Artificial Sequence
<220> FEATURE:
<223> OTHER INFORMATION: AID mutant Mut7.4

<400> SEQUENCE: 43

```
Met Asp Ser Leu Leu Met Asn Arg Arg Glu Phe Leu Tyr Gln Phe Lys
 1               5                  10                 15

Asn Val Arg Trp Ala Lys Gly Arg Arg Glu Thr Tyr Leu Cys Tyr Val
                20                 25                 30

Val Lys Arg Arg Asp Ser Ala Thr Ser Phe Ser Leu Asp Phe Gly Tyr
            35                 40                 45

Leu Arg Asn Lys Asn Gly Cys His Val Glu Leu Leu Phe Leu Arg Tyr
        50                 55                 60

Ile Ser Asp Trp Asp Leu Asp Pro Gly Arg Cys Tyr Arg Val Thr Trp
 65                 70                 75                 80

Phe Thr Ser Arg Ser Pro Cys Tyr Asp Cys Ala Arg His Val Ala Asp
                85                 90                 95

Phe Leu Arg Gly Asn Pro Asn Leu Ser Leu Arg Ile Phe Thr Ala Arg
            100                105                110

Leu Tyr Phe Cys Glu Asp Arg Arg Ala Glu Pro Glu Gly Leu Arg Arg
        115                120                125

Leu His Arg Ala Gly Val Gln Ile Ala Ile Met Thr Phe Lys Asp Tyr
    130                135                140

Phe Tyr Cys Trp Asn Thr Phe Val Glu Asn His Gly Arg Thr Phe Lys
145                150                155                160

Ala Trp Glu Gly Leu His Glu Asn Ser Val Arg Leu Ser Arg Gln Leu
```

```
                165                 170                 175
Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 44
<211> LENGTH: 198
<212> TYPE: PRT
<213> ORGANISM: Artificial Sequence
<220> FEATURE:
<223> OTHER INFORMATION: AID mutant Mut7.5

<400> SEQUENCE: 44

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
130                 135                 140

Leu Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 45
<211> LENGTH: 198
<212> TYPE: PRT
<213> ORGANISM: Artificial Sequence
<220> FEATURE:
<223> OTHER INFORMATION: AID mutant Mut7.6

<400> SEQUENCE: 45

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
50                  55                  60
```

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ser Asp
                85                  90                  95

Phe Leu Arg Gly Asn Pro Asn Leu Ser Leu Arg Ile Phe Thr Ala Arg
            100                 105                 110

Leu Tyr Tyr Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 46
<211> LENGTH: 198
<212> TYPE: PRT
<213> ORGANISM: Artificial Sequence
<220> FEATURE:
<223> OTHER INFORMATION: AID mutant Mut7.7

<400> SEQUENCE: 46

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 47
<211> LENGTH: 198

```
<212> TYPE: PRT
<213> ORGANISM: Artificial Sequence
<220> FEATURE:
<223> OTHER INFORMATION: AID mutant Mut7.8

<400> SEQUENCE: 47

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Arg Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 48
<211> LENGTH: 198
<212> TYPE: PRT
<213> ORGANISM: Artificial Sequence
<220> FEATURE:
<223> OTHER INFORMATION: AID mutant Mut8

<400> SEQUENCE: 48

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125
```

Leu His Arg Ala Gly Val Gln Ile Ala Ile Met Thr Phe Lys Asp Tyr
            130                 135                 140

Phe Tyr Cys Trp Asn Thr Phe Val Glu Asn His Glu Arg Thr Phe Glu
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 49
<211> LENGTH: 198
<212> TYPE: PRT
<213> ORGANISM: Artificial Sequence
<220> FEATURE:
<223> OTHER INFORMATION: AID mutant Mut9

<400> SEQUENCE: 49

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Glu Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
            130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 50
<211> LENGTH: 198
<212> TYPE: PRT
<213> ORGANISM: Artificial Sequence
<220> FEATURE:
<223> OTHER INFORMATION: AID mutant Mut10

<400> SEQUENCE: 50

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val

```
                20                  25                  30
Val Lys Arg Arg Asp Ser Ala Thr Ser Phe Pro Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
 65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Ala Glu Pro Glu Gly Leu Arg Arg
        115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 51
<211> LENGTH: 198
<212> TYPE: PRT
<213> ORGANISM: Artificial Sequence
<220> FEATURE:
<223> OTHER INFORMATION: AID mutant Mut11

<400> SEQUENCE: 51

Met Asp Ser Leu Leu Met Asn Arg Arg Lys Phe Leu Tyr Gln Phe Lys
 1               5                  10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
 65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
```

Phe Arg Thr Leu Gly Leu
        195

<210> SEQ ID NO 52
<211> LENGTH: 198
<212> TYPE: PRT
<213> ORGANISM: Artificial Sequence
<220> FEATURE:
<223> OTHER INFORMATION: AID mutant Mut12

<400> SEQUENCE: 52

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Ala Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Arg Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Leu Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 53
<211> LENGTH: 198
<212> TYPE: PRT
<213> ORGANISM: Artificial Sequence
<220> FEATURE:
<223> OTHER INFORMATION: AID mutant Mut13

<400> SEQUENCE: 53

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Ala Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

```
Tyr Thr Ser Arg Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
            130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 54
<211> LENGTH: 189
<212> TYPE: PRT
<213> ORGANISM: Artificial Sequence
<220> FEATURE:
<223> OTHER INFORMATION: AID mutant Fugu1

<400> SEQUENCE: 54

Met Leu Leu Pro Arg Lys Lys Phe Ile Tyr His Tyr Lys Asn Val Leu
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala
        50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asp Ser Leu
            115                 120                 125

Glu Arg Glu Gly Leu Arg Met Leu Thr Lys Ala Gly Val Arg Ile Ser
            130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
            180                 185

<210> SEQ ID NO 55
<211> LENGTH: 189
<212> TYPE: PRT
<213> ORGANISM: Artificial Sequence
<220> FEATURE:
<223> OTHER INFORMATION: AID mutant Fugu2

<400> SEQUENCE: 55
```

-continued

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
                20                  25                  30

Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala
        50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Arg Phe Leu Asn Asn Thr Pro Asn Leu Arg Leu
            100                 105                 110

Arg Ile Phe Val Ser Arg Leu Tyr Phe Cys Asp Leu Glu Asp Ser Leu
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
                180                 185

<210> SEQ ID NO 56
<211> LENGTH: 228
<212> TYPE: PRT
<213> ORGANISM: Artificial Sequence
<220> FEATURE:
<223> OTHER INFORMATION: AID mutant Fugu3

<400> SEQUENCE: 56

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
                20                  25                  30

Arg Val Gly Pro Asp Thr Leu Ser Asp Phe Gly His Leu Arg Asn
            35                  40                  45

Arg Arg Gly Cys His Val Glu Leu Leu Phe Leu Arg Tyr Leu Gly Ala
        50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asp Ser Leu
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Glu Leu Asn Arg Ile Leu Gln Ala Trp Asp Leu
                180                 185                 190

Asp Asp Leu Arg Asp Ala Leu Asn Pro Pro Asp Ser Glu Asp Pro Leu
            195                 200                 205

Glu Ser Thr Cys Arg His Ala Ser Leu Ala Val Leu Ala Asp Glu Arg
        210                 215                 220

Arg Phe Ser Ala
225

<210> SEQ ID NO 57
<211> LENGTH: 189
<212> TYPE: PRT
<213> ORGANISM: Artificial Sequence
<220> FEATURE:
<223> OTHER INFORMATION: AID mutant Fugu4

<400> SEQUENCE: 57

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
                20                  25                  30

Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala
        50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
                100                 105                 110

Arg Ile Phe Val Ser Arg Leu Tyr Phe Cys Asp Leu Glu Asp Ser Leu
            115                 120                 125

Glu Arg Glu Gly Leu Arg Met Leu Thr Lys Ala Gly Val Arg Ile Ser
        130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
                180                 185

<210> SEQ ID NO 58
<211> LENGTH: 189
<212> TYPE: PRT
<213> ORGANISM: Artificial Sequence
<220> FEATURE:
<223> OTHER INFORMATION: AID mutant Fugu4.1

<400> SEQUENCE: 58

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
                20                  25                  30

Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala

```
                 50                  55                  60
Leu Cys Pro Gly Leu Trp Gly Tyr Gly Ala Ala Gly Glu Lys Arg Leu
 65                  70                  75                  80

Ser Tyr Ser Val Thr Trp Phe Cys Ser Trp Ser Pro Cys Val Asn Cys
                     85                  90                  95

Ser Ile Gln Leu Cys Gln Phe Leu Asn Asn Thr Pro Asn Leu Arg Leu
                100                 105                 110

Arg Ile Phe Val Ser Arg Leu Tyr Phe Cys Asp Leu Glu Asp Ser Leu
                115                 120                 125

Glu Arg Glu Gly Leu Arg Met Leu Thr Lys Ala Gly Val Arg Ile Ser
                130                 135                 140

Val Met Ser Tyr Lys His Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
                180                 185

<210> SEQ ID NO 59
<211> LENGTH: 189
<212> TYPE: PRT
<213> ORGANISM: Artificial Sequence
<220> FEATURE:
<223> OTHER INFORMATION: AID mutant Fugu4.2

<400> SEQUENCE: 59

Met Leu Leu Pro Arg Asn Lys Phe Ile Tyr His Tyr Lys Asn Val Arg
  1               5                  10                  15

Trp Ala Arg Gly Arg His Glu Thr Tyr Leu Cys Phe Val Val Lys Arg
                 20                  25                  30

Arg Val Gly Pro Asp Thr Leu Thr Phe Asp Phe Gly His Leu Arg Asn
                 35                  40                  45

Arg Ser Gly Cys His Val Glu Leu Leu Phe Leu Arg Tyr Leu Gly Ala
                 50                  55                  60

Leu Cys Pro Gly Leu Trp Gly Tyr Gly Ala Ala Gly Glu Lys Arg Leu
 65                  70                  75                  80

Ser Tyr Ser Val Thr Trp Tyr Cys Ser Trp Ser Pro Cys Val Asn Cys
                     85                  90                  95

Ser Ile Gln Leu Cys Gln Phe Leu Asn Asn Thr Pro Asn Leu Arg Leu
                100                 105                 110

Arg Ile Phe Val Ser Arg Leu Tyr Phe Cys Asp Leu Glu Asp Ser Leu
                115                 120                 125

Glu Arg Glu Gly Leu Arg Met Leu Thr Lys Ala Gly Val Arg Ile Ser
                130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
                180                 185

<210> SEQ ID NO 60
<211> LENGTH: 189
<212> TYPE: PRT
<213> ORGANISM: Artificial Sequence
<220> FEATURE:
<223> OTHER INFORMATION: AID mutant Fugu4.3
```

<400> SEQUENCE: 60

```
Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
        35                  40                  45

Arg Ser Gly Cys His Val Glu Leu Leu Phe Leu Arg Tyr Leu Gly Ala
    50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Leu Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asp Ser Leu
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
            180                 185
```

<210> SEQ ID NO 61
<211> LENGTH: 189
<212> TYPE: PRT
<213> ORGANISM: Artificial Sequence
<220> FEATURE:
<223> OTHER INFORMATION: AID mutant Fugu4.4

<400> SEQUENCE: 61

```
Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
        35                  40                  45

Arg Ser Gly Cys His Val Glu Leu Leu Phe Leu Arg Tyr Leu Gly Ala
    50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Tyr Cys Asp Leu Glu Asp Ser Leu
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160
```

Cys Lys Lys Ser Asn Phe Lys Ala Trp Glu Asp Leu His Gln Asn Ser
                165                 170                 175

Val Arg Leu Thr Arg Lys Leu Asn Arg Ile Leu Gln Ala
            180                 185

<210> SEQ ID NO 62
<211> LENGTH: 189
<212> TYPE: PRT
<213> ORGANISM: Artificial Sequence
<220> FEATURE:
<223> OTHER INFORMATION: AID mutant Fugu4.5

<400> SEQUENCE: 62

Met Leu Leu Pro Ser Lys Lys Phe Ile Tyr His Tyr Lys Asn Val Arg
1               5                   10                  15

Trp Ala Arg Gly Arg His Glu Thr Tyr Leu Cys Phe Val Val Lys Arg
                20                  25                  30

Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala
        50                  55                  60

Leu Cys Pro Gly Leu Trp Gly Asn Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
                100                 105                 110

Arg Ile Phe Val Ser Arg Leu Tyr Tyr Cys Asp Leu Glu Asp Ser Leu
            115                 120                 125

Glu Arg Glu Gly Leu Arg Met Leu Thr Lys Ala Gly Val Arg Ile Ser
        130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
            180                 185

<210> SEQ ID NO 63
<211> LENGTH: 189
<212> TYPE: PRT
<213> ORGANISM: Artificial Sequence
<220> FEATURE:
<223> OTHER INFORMATION: AID mutant Fugu4.6

<400> SEQUENCE: 63

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
                20                  25                  30

Arg Val Gly Pro Asp Thr Leu Thr Leu Asp Phe Gly His Leu Arg Asn
            35                  40                  45

Arg Ser Gly Cys His Val Glu Leu Leu Phe Leu Arg Tyr Leu Gly Ala
        50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Pro Glu Asp Ser Leu
            115                 120                 125

Glu Arg Glu Gly Leu Arg Met Leu Thr Lys Ala Gly Val Arg Ile Ser
130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
            165                 170                 175

Val Arg Leu Thr Arg Lys Leu Asn Arg Ile Leu Gln Ala
            180                 185

<210> SEQ ID NO 64
<211> LENGTH: 189
<212> TYPE: PRT
<213> ORGANISM: Artificial Sequence
<220> FEATURE:
<223> OTHER INFORMATION: AID mutant Fugu4.7

<400> SEQUENCE: 64

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala
50                  55                  60

Ile Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
            85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Gln Glu Asp Ser Leu
            115                 120                 125

Glu Arg Glu Gly Leu Arg Met Leu Thr Lys Ala Gly Val Arg Ile Ser
            130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
            165                 170                 175

Val Arg Leu Thr Arg Lys Leu Asn Arg Ile Leu Gln Ala
            180                 185

<210> SEQ ID NO 65
<211> LENGTH: 189
<212> TYPE: PRT
<213> ORGANISM: Artificial Sequence
<220> FEATURE:
<223> OTHER INFORMATION: AID mutant Fugu4.8

<400> SEQUENCE: 65

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg

```
            20                  25                  30
Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala
        50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Met Glu Asp Ser Leu
        115                 120                 125

Glu Arg Glu Gly Leu Arg Met Leu Thr Lys Ala Gly Val Arg Ile Ser
    130                 135                 140

Val Met Ser Tyr Lys Asp Tyr Val Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
            180                 185

<210> SEQ ID NO 66
<211> LENGTH: 189
<212> TYPE: PRT
<213> ORGANISM: Artificial Sequence
<220> FEATURE:
<223> OTHER INFORMATION: AID mutant Fugu4.9

<400> SEQUENCE: 66

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
            35                  40                  45

Arg Ser Gly Cys His Val Glu Leu Leu Phe Leu Arg Tyr Leu Gly Ala
        50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asp Ser Pro
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
            180                 185
```

-continued

```
<210> SEQ ID NO 67
<211> LENGTH: 189
<212> TYPE: PRT
<213> ORGANISM: Artificial Sequence
<220> FEATURE:
<223> OTHER INFORMATION: AID mutant Fugu4.10

<400> SEQUENCE: 67
```

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
        35                  40                  45

Arg Ser Gly Cys His Val Glu Leu Leu Phe Leu Arg Tyr Leu Gly Ala
    50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asp Ser Pro
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala
            180                 185

```
<210> SEQ ID NO 68
<211> LENGTH: 207
<212> TYPE: PRT
<213> ORGANISM: Artificial Sequence
<220> FEATURE:
<223> OTHER INFORMATION: AID mutant Fugu5

<400> SEQUENCE: 68
```

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Phe Asp Phe Gly His Leu Arg Asn
        35                  40                  45

Arg Arg Gly Cys His Val Glu Leu Leu Phe Leu Arg Tyr Leu Gly Ala
    50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asp Ser Leu
        115                 120                 125

Glu Arg Glu Gly Leu Arg Met Leu Thr Lys Ala Gly Val Arg Ile Ser
            130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Gly Leu His Gln Asn Ser
                165                 170                 175

Val Arg Leu Thr Arg Lys Leu Asn Arg Ile Leu Gln Ala Trp Asp Leu
            180                 185                 190

Glu Asp Leu Arg Asp Thr Leu Ser Pro Arg Ile Leu Arg Ile Leu
        195                 200                 205

<210> SEQ ID NO 69
<211> LENGTH: 191
<212> TYPE: PRT
<213> ORGANISM: Artificial Sequence
<220> FEATURE:
<223> OTHER INFORMATION: AID mutant Fugu6

<400> SEQUENCE: 69

Met Leu Leu Pro Arg Lys Lys Phe Ile Tyr His Tyr Lys Asn Val Arg
1               5                   10                  15

Trp Ala Arg Gly Arg His Glu Thr Tyr Leu Cys Phe Val Val Lys Arg
            20                  25                  30

Arg Val Gly Pro Asp Thr Leu Thr Ser Asp Phe Gly His Leu Arg Asn
        35                  40                  45

Arg Ser Gly Cys His Val Glu Leu Leu Phe Leu Arg Tyr Leu Gly Ala
    50                  55                  60

Leu Cys Pro Gly Leu Trp Gly Tyr Gly Ala Ala Gly Glu Lys Arg Leu
65                  70                  75                  80

Ser Tyr Ser Val Thr Trp Phe Cys Ser Trp Ser Pro Cys Val Asn Cys
                85                  90                  95

Ser Ile Gln Leu Cys Gln Phe Leu Asn Asn Thr Pro Asn Leu Arg Leu
            100                 105                 110

Arg Ile Phe Val Ser Arg Leu Tyr Phe Cys Asp Leu Glu Asn Ser Leu
        115                 120                 125

Glu Arg Glu Gly Leu Arg Met Leu Thr Lys Ala Gly Val Arg Ile Ser
    130                 135                 140

Val Met Ser Tyr Lys Asp Tyr Phe Tyr Cys Trp Gln Lys Phe Val Asp
145                 150                 155                 160

Cys Lys Lys Ser Asn Phe Lys Ala Trp Glu Glu Leu His Gln Asn Ser
                165                 170                 175

Val Arg Leu Thr Arg Lys Leu Asn Arg Ile Leu Gln Ala Trp Asp
            180                 185                 190

<210> SEQ ID NO 70
<211> LENGTH: 198
<212> TYPE: PRT
<213> ORGANISM: Artificial Sequence
<220> FEATURE:
<223> OTHER INFORMATION: AB350 w/o FLAG/NLS

<400> SEQUENCE: 70

Met Asp Ser Leu Leu Met Lys Gln Arg Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Ala Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Lys Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Ala
        195

<210> SEQ ID NO 71
<211> LENGTH: 198
<212> TYPE: PRT
<213> ORGANISM: Artificial Sequence
<220> FEATURE:
<223> OTHER INFORMATION: AB273 w/o FLAG/NLS

<400> SEQUENCE: 71

Met Asp Ser Leu Leu Met Lys Gln Arg Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Ala Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Lys Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Glu Glu Leu Arg Glu Ala
            180                 185                 190

Phe Arg Ile Leu Gly Ala
        195

<210> SEQ ID NO 72
<211> LENGTH: 214
<212> TYPE: PRT
<213> ORGANISM: Artificial Sequence
<220> FEATURE:
<223> OTHER INFORMATION: AB350

<400> SEQUENCE: 72

```
Met Asp Tyr Lys Asp Asp Asp Lys Gly Pro Lys Lys Arg Lys
1               5                   10                  15

Val Asp Ser Leu Leu Met Lys Gln Arg Lys Phe Leu Tyr His Phe Lys
            20                  25                  30

Asn Val Arg Trp Ala Lys Gly Arg His Glu Thr Tyr Leu Cys Tyr Val
            35                  40                  45

Val Lys Arg Arg Asp Ser Ala Thr Ser Phe Ser Leu Asp Phe Gly His
    50                  55                  60

Leu Arg Asn Lys Ser Gly Cys His Val Glu Leu Leu Phe Leu Arg Tyr
65                  70                  75                  80

Ile Ser Asp Trp Asp Leu Asp Pro Gly Arg Cys Tyr Arg Val Thr Trp
                85                  90                  95

Phe Thr Ser Trp Ser Pro Cys Tyr Asp Cys Ala Arg His Val Ala Asp
                100                 105                 110

Phe Leu Arg Gly Tyr Pro Asn Leu Ser Leu Arg Ile Phe Ala Ala Arg
            115                 120                 125

Leu Tyr Phe Cys Glu Asp Arg Lys Ala Glu Pro Glu Gly Leu Arg Arg
        130                 135                 140

Leu His Arg Ala Gly Val Gln Ile Ala Ile Met Thr Phe Lys Asp Tyr
145                 150                 155                 160

Phe Tyr Cys Trp Asn Thr Phe Val Glu Asn Arg Glu Lys Thr Phe Lys
                165                 170                 175

Ala Trp Glu Gly Leu His Glu Asn Ser Val Arg Leu Ser Arg Gln Leu
            180                 185                 190

Arg Arg Ile Leu Leu Pro Leu Tyr Glu Val Asp Asp Leu Arg Asp Ala
        195                 200                 205

Phe Arg Thr Leu Gly Ala
        210
```

<210> SEQ ID NO 73
<211> LENGTH: 214
<212> TYPE: PRT
<213> ORGANISM: Artificial Sequence
<220> FEATURE:
<223> OTHER INFORMATION: AB273

<400> SEQUENCE: 73

```
Met Asp Tyr Lys Asp Asp Asp Lys Gly Pro Lys Lys Arg Lys
1               5                   10                  15

Val Asp Ser Leu Leu Met Lys Gln Arg Lys Phe Leu Tyr His Phe Lys
            20                  25                  30

Asn Val Arg Trp Ala Lys Gly Arg His Glu Thr Tyr Leu Cys Tyr Val
            35                  40                  45

Val Lys Arg Arg Asp Ser Ala Thr Ser Phe Ser Leu Asp Phe Gly His
    50                  55                  60

Leu Arg Asn Lys Ser Gly Cys His Val Glu Leu Leu Phe Leu Arg Tyr
65                  70                  75                  80

Ile Ser Asp Trp Asp Leu Asp Pro Gly Arg Cys Tyr Arg Val Thr Trp
```

85                  90                  95
Phe Thr Ser Trp Ser Pro Cys Tyr Asp Cys Ala Arg His Val Ala Asp
                100                 105                 110

Phe Leu Arg Gly Tyr Pro Asn Leu Ser Leu Arg Ile Phe Ala Ala Arg
                115                 120                 125

Leu Tyr Phe Cys Glu Asp Arg Lys Ala Glu Pro Gly Leu Arg Arg
130                 135                 140

Leu His Arg Ala Gly Val Gln Ile Ala Ile Met Thr Phe Lys Asp Tyr
145                 150                 155                 160

Phe Tyr Cys Trp Asn Thr Phe Val Glu Asn Arg Glu Lys Thr Phe Lys
                165                 170                 175

Ala Trp Glu Gly Leu His Glu Asn Ser Val Arg Leu Ser Arg Gln Leu
                180                 185                 190

Arg Arg Ile Leu Leu Pro Leu Tyr Glu Val Glu Glu Leu Arg Glu Ala
                195                 200                 205

Phe Arg Ile Leu Gly Ala
        210

<210> SEQ ID NO 74
<211> LENGTH: 645
<212> TYPE: DNA
<213> ORGANISM: Artificial Sequence
<220> FEATURE:
<223> OTHER INFORMATION: AB350

<400> SEQUENCE: 74
atggactaca aagatgacga tgataaaggt ccaaagaaga agagaaaggt agactctctc    60
ctcatgaagc agagaaagtt tctctaccac ttcaagaacg tcagatgggc caaggggaga   120
catgagacct atctctgtta cgtcgtcaag aggagagact cagccacctc tttctccctc   180
gactttgggc atctccggaa caagtctggg tgtcatgtcg aactcctctt cctccgctat   240
atctcagact gggacctcga ccccgggaga tgctatagag tcacttggtt tacctcttgg   300 tcccctgtt atgactgcgc cagacatgtc gccgacttcc tcaggggta tcccaatctc   360 tccctccgca tattcgccgc ccgactctat ttttgtgagg acaggaaagc cgagcccgag   420
gggctcagga gactccaccg gccgggggtc cagatcgcca tcatgacatt taaggactat   480
ttctattgtt ggaatacatt tgtcgagaat cgggagaaga cttttcaaagc ctggaggggg   540 ctccatgaga actctgtcag actctctagg cagctcagga gaatcctcct ccccctctat   600
gaggtcgacg acctcagaga tgccttccgg accctcgggg cttga               645

<210> SEQ ID NO 75
<211> LENGTH: 645
<212> TYPE: DNA
<213> ORGANISM: Artificial Sequence
<220> FEATURE:
<223> OTHER INFORMATION: AB273

<400> SEQUENCE: 75
atggactaca aagatgacga tgataaaggt ccaaagaaga agagaaaggt agactctctc    60
ctcatgaagc agagaaagtt tctctaccac ttcaagaacg tcagatgggc caaggggaga   120
catgagacct atctctgtta cgtcgtcaag aggagagact cagccacctc tttctccctc   180
gactttgggc atctccggaa caagtctggg tgtcatgtcg aactcctctt cctccgctat   240
atctcagact gggacctcga ccccgggaga tgctatagag tcacttggtt tacctcttgg   300 tcccctgtt atgactgcgc cagacatgtc gccgacttcc tcaggggta tcccaatctc   360

```
tccctccgca tattcgccgc ccgactctat ttttgtgagg acaggaaagc cgagcccgag    420
gggctcagga gactccaccg ggccggggtc cagatcgcca tcatgacatt taaggactat    480
ttctattgtt ggaatacatt tgtcgagaat cgggagaaga ctttcaaagc ctgggagggg    540
ctccatgaga actctgtcag actctctagg cagctcagga gaatcctcct ccccctctat    600
gaggtcgaag aactcagaga agccttccgg atcctcgggg cttga                   645
```

```
<210> SEQ ID NO 76
<211> LENGTH: 7
<212> TYPE: PRT
<213> ORGANISM: Artificial Sequence
<220> FEATURE:
<223> OTHER INFORMATION: Consensus NLS

<400> SEQUENCE: 76

Pro Lys Lys Lys Arg Lys Val
1               5

<210> SEQ ID NO 77
<211> LENGTH: 16
<212> TYPE: PRT
<213> ORGANISM: Artificial Sequence
<220> FEATURE:
<223> OTHER INFORMATION: Bipartite NLS

<400> SEQUENCE: 77

Lys Arg Pro Ala Ala Thr Lys Lys Ala Gly Gln Ala Lys Lys Lys Lys
1               5                   10                  15

<210> SEQ ID NO 78
<211> LENGTH: 5
<212> TYPE: PRT
<213> ORGANISM: Artificial Sequence
<220> FEATURE:
<223> OTHER INFORMATION: NLS motif

<400> SEQUENCE: 78

Lys Ile Pro Ile Lys
1               5

<210> SEQ ID NO 79
<211> LENGTH: 22
<212> TYPE: DNA
<213> ORGANISM: Artificial Sequence
<220> FEATURE:
<223> OTHER INFORMATION: LacZ forward

<400> SEQUENCE: 79
agaattcctg aagttcagat gt                                             22

<210> SEQ ID NO 80
<211> LENGTH: 21
<212> TYPE: DNA
<213> ORGANISM: Artificial Sequence
<220> FEATURE:
<223> OTHER INFORMATION: LacZ reverse primer

<400> SEQUENCE: 80
ggaattcgaa accgccaaga c                                              21

<210> SEQ ID NO 81
<211> LENGTH: 24
<212> TYPE: DNA
<213> ORGANISM: Artificial Sequence
```

```
<220> FEATURE:
<223> OTHER INFORMATION: hAID forward primer

<400> SEQUENCE: 81
atggaattca tggacagcct cttg                                          24

<210> SEQ ID NO 82
<211> LENGTH: 25
<212> TYPE: DNA
<213> ORGANISM: Artificial Sequence
<220> FEATURE:
<223> OTHER INFORMATION: hAID reverse primer

<400> SEQUENCE: 82
ctgaagcttt caaagtccca aagta                                         25

<210> SEQ ID NO 83
<211> LENGTH: 21
<212> TYPE: DNA
<213> ORGANISM: Artificial Sequence
<220> FEATURE:
<223> OTHER INFORMATION: rpoB forward primer

<400> SEQUENCE: 83
ttggcgaaat ggcggaaaac c                                             21

<210> SEQ ID NO 84
<211> LENGTH: 22
<212> TYPE: DNA
<213> ORGANISM: Artificial Sequence
<220> FEATURE:
<223> OTHER INFORMATION: rpoB reverse primer

<400> SEQUENCE: 84
caccgacgga taccacctgc tg                                            22

<210> SEQ ID NO 85
<211> LENGTH: 44
<212> TYPE: DNA
<213> ORGANISM: Artificial Sequence
<220> FEATURE:
<223> OTHER INFORMATION: Deaminase substrate (5'-FITC; 3'-biotin)

<400> SEQUENCE: 85
atatgaatag aatagagggg tgagctgggg tgagctgggg tgag                    44

<210> SEQ ID NO 86
<211> LENGTH: 5
<212> TYPE: PRT
<213> ORGANISM: Artificial Sequence
<220> FEATURE:
<223> OTHER INFORMATION: Zinc-coordination motif

<400> SEQUENCE: 86

Pro Cys Tyr Asp Cys
1               5

<210> SEQ ID NO 87
<211> LENGTH: 7
<212> TYPE: PRT
<213> ORGANISM: Artificial Sequence
<220> FEATURE:
<223> OTHER INFORMATION: Zinc-coordination motif

<400> SEQUENCE: 87

Phe Cys Glu Asp Arg Lys Ala
```

<210> SEQ ID NO 88
<211> LENGTH: 645
<212> TYPE: DNA
<213> ORGANISM: Artificial Sequence
<220> FEATURE:
<223> OTHER INFORMATION: Canine AID mutant

<400> SEQUENCE: 88

| | | | | | | |
|---|---|---|---|---|---|---|
| atggactaca | aagatgacga | tgataaaggt | ccaaagaaga | agagaaaggt | agactctctc | 60 |
| ctcatgaagc | agagaaagtt | tctctaccac | ttcaagaacg | tcagatgggc | caaggggaga | 120 |
| catgagacct | atctctgtta | cgtcgtcaag | aggagagact | cagccacctc | tttctccctc | 180 |
| gactttgggc | atctccggaa | caagtctggg | tgtcatgtcg | aactcctctt | cctccgctat | 240 |
| atctcagact | gggacctcga | ccccgggaga | tgctatagag | tcacttggtt | tacctcttgg | 300 |
| tccccctgtt | atgactgcgc | cagacatgtc | gccgacttcc | tcaggggta | tcccaatctc | 360 |
| tccctccgca | tattcgccgc | ccgactctat | ttttgtgagg | acaggaaagc | cgagcccgag | 420 |
| gggctcagga | gactccaccg | ggccggggtc | cagatcgcca | tcatgacatt | taaggactat | 480 |
| ttctattgtt | ggaatacatt | tgtcgagaat | cgggagaaga | ctttcaaagc | ctgggagggg | 540 |
| ctccatgaga | actctgtcag | actctctagg | cagctcagga | gaatcctcct | cccctctat | 600 |
| gaggtcgaag | aactcagaga | agccttccgg | atcctcgggg | cttga | | 645 |

<210> SEQ ID NO 89
<211> LENGTH: 645
<212> TYPE: DNA
<213> ORGANISM: Artificial Sequence
<220> FEATURE:
<223> OTHER INFORMATION: Canine AID mutant

<400> SEQUENCE: 89

| | | | | | | |
|---|---|---|---|---|---|---|
| atggactaca | aagatgacga | tgataaaggt | ccaaagaaga | agagaaaggt | agactctctc | 60 |
| ctcatgaagc | agagagagtt | tctctaccac | ttcaagaacg | tcagatgggc | caaggggaga | 120 |
| catgagacct | atctctgtta | cgtcgtcaag | aggagagact | cagccacctc | tttctccctc | 180 |
| gactttgggc | atctccggaa | caagtctggg | tgtcatgtcg | aactcctctt | cctccgctat | 240 |
| atctcagact | gggacctcga | ccccgggaga | tgctatagag | tcacttggtt | tatctcttgg | 300 |
| tccccctgtt | atgactgcgc | cagacatgtc | gccgacttcc | tcaggggta | tcccaatctc | 360 |
| tccctccgca | tattcgccgc | ccgactctat | ttttgtgagg | acaggaaagc | cgagcccgag | 420 |
| gggctcagga | gactccaccg | ggccggggtc | cagatcgcca | tcatgacatt | taaggactat | 480 |
| ttctattgtt | ggaatacatt | tgtcgagaat | cggggaaga | ctttcaaagc | ctgggagggg | 540 |
| ctccatgaga | actctgtcag | actctctagg | cagctcagga | gaatcctcct | cccctctat | 600 |
| gaggtcgaag | aactcagaga | agccttccgg | atcctcgggg | cttga | | 645 |

<210> SEQ ID NO 90
<211> LENGTH: 597
<212> TYPE: DNA
<213> ORGANISM: Artificial Sequence
<220> FEATURE:
<223> OTHER INFORMATION: Human AID mutant

<400> SEQUENCE: 90

| | | | | | | |
|---|---|---|---|---|---|---|
| atggacagcc | tcttgatgaa | ccggaggag | tttctttacc | aattcaaaaa | tgtccgctgg | 60 |
| gctaagggtc | ggcgtgagac | ctacctgtgc | tacgtagtga | agaggcgtga | cagtgctaca | 120 |

-continued

```
tccttttcac tggactttgg ttatcttcgc aataagaacg gctgccacgt ggaattgctc    180
ttcctccgct acatctcgga ctgggaccta gaccctggcc gctgctaccg cgtcacctgg    240
ttcatctcct ggagccctg ctacgactgt gcccgacatg tggccgactt tctgcgaggg     300
aaccccaacc tcagtctgag gatcttcacc gcgcgcctct acttctgtga ggaccgcaag    360
gctgagcccg aggggctgcg gcggctgcac cgcgccgggg tgcaaatagc catcatgacc    420
ttcaaagatt atttttactg ctggaatact tttgtagaaa accacggaag aactttcaaa    480
gcctgggaag ggctgcatga aaattcagtt cgtctctcca gacagcttcg gcgcatcctt    540
ttgcccctgt atgaggttga tgacttacga gacgcatttc gtactttggg actttga      597
```

<210> SEQ ID NO 91
<211> LENGTH: 214
<212> TYPE: PRT
<213> ORGANISM: Artificial Sequence
<220> FEATURE:
<223> OTHER INFORMATION: Canine AID mutant

<400> SEQUENCE: 91

```
Met Asp Tyr Lys Asp Asp Asp Lys Gly Pro Lys Lys Lys Arg Lys
1               5                   10                  15

Val Asp Ser Leu Leu Met Lys Gln Arg Lys Phe Leu Tyr His Phe Lys
            20                  25                  30

Asn Val Arg Trp Ala Lys Gly Arg His Glu Thr Tyr Leu Cys Tyr Val
        35                  40                  45

Val Lys Arg Arg Asp Ser Ala Thr Ser Phe Ser Leu Asp Phe Gly His
    50                  55                  60

Leu Arg Asn Lys Ser Gly Cys His Val Glu Leu Leu Phe Leu Arg Tyr
65                  70                  75                  80

Ile Ser Asp Trp Asp Leu Asp Pro Gly Arg Cys Tyr Arg Val Thr Trp
                85                  90                  95

Phe Thr Ser Trp Ser Pro Cys Tyr Asp Cys Ala Arg His Val Ala Asp
            100                 105                 110

Phe Leu Arg Gly Tyr Pro Asn Leu Ser Leu Arg Ile Phe Ala Ala Arg
        115                 120                 125

Leu Tyr Phe Cys Glu Asp Arg Lys Ala Glu Pro Glu Gly Leu Arg Arg
    130                 135                 140

Leu His Arg Ala Gly Val Gln Ile Ala Ile Met Thr Phe Lys Asp Tyr
145                 150                 155                 160

Phe Tyr Cys Trp Asn Thr Phe Val Glu Asn Arg Glu Lys Thr Phe Lys
                165                 170                 175

Ala Trp Glu Gly Leu His Glu Asn Ser Val Arg Leu Ser Arg Gln Leu
            180                 185                 190

Arg Arg Ile Leu Leu Pro Leu Tyr Glu Val Glu Glu Leu Arg Glu Ala
        195                 200                 205

Phe Arg Ile Leu Gly Ala
    210
```

<210> SEQ ID NO 92
<211> LENGTH: 214
<212> TYPE: PRT
<213> ORGANISM: Artificial Sequence
<220> FEATURE:
<223> OTHER INFORMATION: Canine AID mutant

<400> SEQUENCE: 92

```
Met Asp Tyr Lys Asp Asp Asp Lys Gly Pro Lys Lys Lys Arg Lys
1               5                   10                  15

Val Asp Ser Leu Leu Met Lys Gln Arg Glu Phe Leu Tyr His Phe Lys
            20                  25                  30

Asn Val Arg Trp Ala Lys Gly Arg His Glu Thr Tyr Leu Cys Tyr Val
            35                  40                  45

Val Lys Arg Arg Asp Ser Ala Thr Ser Phe Ser Leu Asp Phe Gly His
50                  55                  60

Leu Arg Asn Lys Ser Gly Cys His Val Glu Leu Phe Leu Arg Tyr
65                  70                  75                  80

Ile Ser Asp Trp Asp Leu Asp Pro Gly Arg Cys Tyr Arg Val Thr Trp
                85                  90                  95

Phe Ile Ser Trp Ser Pro Cys Tyr Asp Cys Ala Arg His Val Ala Asp
            100                 105                 110

Phe Leu Arg Gly Tyr Pro Asn Leu Ser Leu Arg Ile Phe Ala Ala Arg
            115                 120                 125

Leu Tyr Phe Cys Glu Asp Arg Lys Ala Glu Pro Glu Gly Leu Arg Arg
        130                 135                 140

Leu His Arg Ala Gly Val Gln Ile Ala Ile Met Thr Phe Lys Asp Tyr
145                 150                 155                 160

Phe Tyr Cys Trp Asn Thr Phe Val Glu Asn Arg Gly Lys Thr Phe Lys
                165                 170                 175

Ala Trp Glu Gly Leu His Glu Asn Ser Val Arg Leu Ser Arg Gln Leu
            180                 185                 190

Arg Arg Ile Leu Leu Pro Leu Tyr Glu Val Glu Glu Leu Arg Glu Ala
            195                 200                 205

Phe Arg Ile Leu Gly Ala
        210

<210> SEQ ID NO 93
<211> LENGTH: 198
<212> TYPE: PRT
<213> ORGANISM: Artificial Sequence
<220> FEATURE:
<223> OTHER INFORMATION: Human AID mutant

<400> SEQUENCE: 93

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
50                  55                  60

Ile Ser Asp Trp Asp Leu Asp Pro Gly Arg Cys Tyr Arg Val Thr Trp
65                  70                  75                  80

Phe Ile Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140
```

-continued

```
Phe Tyr Cys Trp Asn Thr Phe Val Glu Asn His Gly Arg Thr Phe Lys
145             150             155             160

Ala Trp Glu Gly Leu His Glu Asn Ser Val Arg Leu Ser Arg Gln Leu
                165             170             175

Arg Arg Ile Leu Leu Pro Leu Tyr Glu Val Asp Asp Leu Arg Asp Ala
            180             185             190

Phe Arg Thr Leu Gly Leu
            195
```